US008951789B2

(12) United States Patent

Oshimura et al.

(10) Patent No.: US 8,951,789 B2
(45) Date of Patent: Feb. 10, 2015

(54) MAMMALIAN ARTIFICIAL CHROMOSOME VECTOR COMPRISING HUMAN CYTOCHROME P450 GENE (CLUSTER) AND NON-HUMAN MAMMALIAN ANIMAL RETAINING THE SAME

(75) Inventors: Mitsuo Oshimura, Tottori (JP); Yasuhiro Kazuki, Tottori (JP); Takashi Matsuoka, Tottori (JP); Kazuma Tomizuka, Gunma (JP); Takeshi Oshima, Gunma (JP)

(73) Assignees: National University Corporation Tottori University, Tottori-shi (JP); Chromocenter Inc., Yonago-shi (JP)

(*) Notice: Subject to any disclaimer, the term of this patent is extended or adjusted under 35 U.S.C. 154(b) by 219 days.

(21) Appl. No.: 12/743,065

(22) PCT Filed: Oct. 14, 2008

(86) PCT No.: PCT/JP2008/068928

§ 371 (c)(1), (2), (4) Date: May 14, 2010

(87) PCT Pub. No.: WO2009/063722

PCT Pub. Date: May 22, 2009

(65) Prior Publication Data

US 2011/0023138 A1 Jan. 27, 2011

(30) Foreign Application Priority Data

Nov. 14, 2007 (JP) ................................ 2007-295993

(51) Int. Cl.

| | |
|---|---|
| ***C12N 15/63*** | (2006.01) |
| ***C12N 5/06*** | (2006.01) |
| ***C12N 15/85*** | (2006.01) |
| ***A01K 67/027*** | (2006.01) |
| ***C12N 9/02*** | (2006.01) |
| ***G01N 33/50*** | (2006.01) |
| *A01K 67/00* | (2006.01) |

(52) U.S. Cl.

CPC ........ *C12N 15/8509* (2013.01); *A01K 67/0278* (2013.01); *C12N 9/0071* (2013.01); *C12N 9/0077* (2013.01); *G01N 33/5088* (2013.01); *A01K 2217/00* (2013.01); *A01K 2217/07* (2013.01); *A01K 2227/105* (2013.01); *C12N 2800/208* (2013.01)

USPC ......................... 435/320.1; 435/455; 435/349

(58) Field of Classification Search

USPC ...................................... 435/320.1, 349, 455

See application file for complete search history.

(56) References Cited

U.S. PATENT DOCUMENTS

| | | | | |
|---|---|---|---|---|
| 6,645,745 | B1 * | 11/2003 | Wojnowski et al. | .......... 435/183 |
| 7,402,729 | B2 | 7/2008 | Kuroiwa et al. | |
| 7,476,536 | B2 | 1/2009 | Kuroiwa et al. | |
| 2006/0015958 | A1 * | 1/2006 | Kuroiwa et al. | ................ 800/18 |
| 2007/0101443 | A1 | 5/2007 | Daly | |
| 2008/0148416 | A1 | 6/2008 | Wolf et al. | |
| 2008/0317743 | A1 | 12/2008 | Kuroiwa et al. | |

FOREIGN PATENT DOCUMENTS

| | | |
|---|---|---|
| WO | 01 11951 | 2/2001 |
| WO | 02 083897 | 10/2002 |
| WO | 02 092812 | 11/2002 |
| WO | 2006 064197 | 5/2006 |

OTHER PUBLICATIONS

William R. A. Brown, et al., "Artifical chromosomes: ideal vectors?", Trends in Biotechnology, vol. 18, No. 5, May 1, 2000, pp. 218-223.

Kuroiwa, Y. et al., "The Use of Chromosome-Based Vectors for Animal Transgenesis", Gene Therapy, vol. 9, pp. 708-712 (2002).

* cited by examiner

*Primary Examiner* — Quang Nguyen

(74) *Attorney, Agent, or Firm* — Oblon, Spivak, McClelland, Maier & Neustadt, L.L.P.

(57) ABSTRACT

This invention relates to a mammalian artificial chromosome vector, which retains a human chromosome 7 fragment comprising human cytochrome P450 genes and is transmittable to progeny, wherein the human chromosome 7 fragment retains a region of approximately 1 Mb±500 Kb in size comprising at least a human CYP3A gene cluster, which region is located between chromosome markers AC004922 and AC073842, and to a non-human mammalian animal retaining the vector.

1 Claim, 24 Drawing Sheets

MAMMALIAN ARTIFICIAL CHROMOSOME VECTOR COMPRISING HUMAN CYTOCHROME P450 GENE (CLUSTER) AND NON-HUMAN MAMMALIAN ANIMAL RETAINING THE SAME

CROSS-REFERENCE TO RELATED APPLICATIONS

The present application is a 35 U.S.C. §371 National Stage patent application of International patent application PCT/JP2008/068928, filed on Oct. 14, 2008, which claims priority to Japanese patent application JP 2007-295993, filed on Nov. 14, 2007.

TECHNICAL FIELD

The present invention relates to a mammalian artificial chromosome vector that retains a human chromosome 7 fragment comprising human cytochrome P450 genes and is transmittable to progeny.

The present invention also relates to a non-human mammalian animal retaining said vector, such as a mouse, and to a cell, organ, or tissue thereof.

The present invention further relates to a method for preparing human cytochrome P450 using said non-human mammalian animal or said cell, organ or tissue thereof, or to a method for testing a pharmacological effect and/or metabolism of drugs or food products using the same.

BACKGROUND ART

In vivo drug metabolism is performed by cytochrome P450 (which, hereafter, may be referred to as "P450"), which is mainly present in the liver. P450 constitutes a superfamily comprising many genes. P450 genes having amino acid sequence homology of higher than 40% are classified as belonging to the same family, and those exhibiting 55% or higher amino acid sequence homology within the same family are classified as belonging to its subfamily (Nelson et al., Pharmacogenetics, 6: 1, 1996). When human P450 and rat P450 genes that belong to the same subfamily are compared, differences are observed in properties, and differences are occasionally observed in substrates or metabolites. Thus, information regarding the metabolism of a certain drug in rats is not applicable to humans, and there are needs for development of a test system that can accurately predict drug metabolism in humans (Funae et al., Bioscience & industry, 55: 81, 1997).

Use of human hepatic microsomes is a means for investigating drug metabolism in humans; however, it is difficult to obtain human hepatic microsomes. Meanwhile, genetic engineering techniques have enabled preparation of human enzymes in a relatively easy manner. This enables a stable supply of human enzymes that satisfy the same spec, and use of such techniques is thus taken into consideration (Kamataki, Report from the Biosafety Research Center, Foods, Drugs and Pesticides (An-Pyo Center), 7: 27, 1997). And, in vitro systems for investigating an effect of drugs that have been metabolized by P450 and activated on the living body have been constructed. In such systems, hepatic microsomes and drugs are added to cell cultures to investigate the effect of the metabolites, which had been metabolized outside the cells, on the aforementioned cells. In such a case, activated substances adsorb to cell membranes and only some of such substances can enter into the cells. Accordingly, it is considered that the effect of metabolites on cells cannot be accurately understood by such systems. P450 is considered that, when cells express P450, drugs that had invaded into cells without adsorbing on cell membranes are activated in the cells and the effect of metabolites, including toxicity, is accurately reproduced. Thus, use of cells into which the human P450 gene has been introduced for evaluation of toxicity of metabolites is considered preferable (Kamataki et al., Toxicology Letters, 82-83: 879, 1995).

At present, however, methods involving the use of in vitro expression systems suffer from some drawbacks. The expression system involving the use of yeast cells into which human P450 had been introduced (e.g., Kovaleva et al., Biochem. Biophys. Res. Commun., 221: 129, 1996) is advantageous in that P450 is expressed to some extent without modification of P450 cDNA; however, this system disadvantageously contains P450 of yeast cells. The expression system involving the use of *E. coli* (e.g., Gillam et al., Arch. Biochem. Biophys., 305: 123, 1993) is easy to handle, and this system can produce a large quantity of enzymes. However, the N-terminal amino acid of P450 to be expressed is required to be modified, in order to stably express P450. This system has drawbacks such that, for example, modification as described above may influence enzyme activity and further addition of reducing enzymes is necessary since *E. coli* does not have reducing enzymes that are necessary for exhibiting P450 activity. Also, the system involving the use of insect cells and baculoviruses (e.g., Asseffa et al., Arch. Biochem. Biophys., 274: 481, 1989) can express P450 at high levels, and it does not necessitate modification of N-terminal amino acids, although manipulations for expression require some skill. Since the system involving the use of HepG2 cell derived from human hepatic cancer and vaccinia virus (e.g., Shou et al., Mol. Carcinog., 10: 159, 1994) or a system involving use of human B lymphocytes uses human cells, P450 may be expressed in a manner more similar to that in the in vivo environment. When vaccinia virus or HepG2 cell microsome is used, however, attention should be paid to safety (Funae et al., Bioscience & industry, 55: 81, 1997).

Biological roles and regulation of drug-metabolizing enzymes have not yet been fully elucidated. Experimental systems involving the use of animal cells, yeast cells, insect cells, and bacterial cells can function as model systems for investigating the roles of P450 in drug metabolism in vitro and chemical carcinogenesis. However, the fact that such systems do not fully reflect the in vivo conditions because of other factors such as pharmacokinetic parameters should be taken into consideration when using such systems (Wolf et al., J. Pharm. Pharmacol., 50: 567, 1998). If an experimental animal into which the human P450 gene has been introduced and in which the same metabolites as those produced by humans are produced in vivo is developed, toxicity as well as pharmacological effects of metabolites that are generated specifically in humans could be advantageously investigated with the use of animals (Kamataki et al., Yakubutsu Dotai (pharmacokinetics), 13: 280, 1998). To this end, transgenic mice into which the P450 gene had been introduced have been researched. For example, Ramsden et al. (Ramsden et al., J. Biol. Chem., 268: 21722, 1993) constructed transgenic mice into which the rat Cyp2B2 gene had been introduced. It is known that rat Cyp2B2 gene expression is regulated in a tissue-specific and development-specific manner and that such expression is induced by phenobarbital. When inducing expression of a transgene by phenobarbital in transgenic mice, use of an 800-bp promoter sequence alone is insufficient, and use of a gene sequence located upstream is necessary. Also, the control of the transgene expression requires a sequence located several tens of kb upstream of the transcription initiation site, and such sequence may be able to reproduce expression level and tissue specificity (Ramsden et al., J. Biol. Chem., 268: 21722, 1993).

Also, Loefgren et al. constructed transgenic mice comprising bacterial artificial chromosomes (BACs) retaining CYP2C18 or CYP2C19 and reported sexual differences in expression. In this system, the site of gene introduction is mouse chromosome 2 Cl and the copy number was 11-13. Since the copy number of human genes is generally 2, such transgenic mice were found to be insufficient as models for physiologically expressing human CYP2C (Loefgren et al., American Society for Pharmacology and Experimental Therapeutics, 36: 955-962, 2008).

Also, Yu et al. (Yu et al., Endocrinology, 146: 2911, 2005) constructed transgenic mice comprising the bacterial artificial chromosome (BAC) retaining CYP3A4 that is expressed specifically in adult humans. In this example, the introduced CYP3A4 gene was expressed only in 2-week-old and 4-week-old mice; however, gene expression was observed in 8-week-old mice when an expression inducer was administered. These transgenic mice exhibited poor development in the mammary glands, and the survival of progeny thereof was poor. Regarding this system, the site of introduction and the copy number of the introduced genes have not been tested. In order to verify that such poor development or survival is caused by the CYP3A4 gene, accordingly, it was considered to be necessary to investigate reproducibility in mouse lines different in copy numbers and insertion sites.

Further, Li et al. (Li et al., Archs. Biochem. Biophys., 329: 235, 1996) constructed transgenic mice having CYP3A7 which is expressed specifically in human embryos. In this example, a metallothionein promoter was used, and induction of tissue-specific expression of the P450 gene was not observed. Specifically, expression of the introduced CYP3A7 gene in the liver was observed only in one of six transgenic mouse lines, expression of the gene was observed in various organs in other strains, and the native tissue-specificity was not observed. Accordingly, use of the metallothionein promoter may not be sufficient to express a P450 gene in a liver-specific manner.

Regarding CYP3A, application thereof as a tool for research on toxicity during the fetal period has been studied (Kamataki et al., Toxicology Letters, 82-83: 879, 1995). Also, Campbell et al. (Campbell et al., J. Cell Sci., 109: 2619, 1996) constructed transgenic mice into which the gene prepared by linking a promoter sequence of rat Cyp1A1 gene and an upstream sequence thereof to a lacZ gene had been introduced, and analyzed regulation of gene expression by Cyp1A1 using the transgenic mice.

In addition to transgenic mice, P450 knockout mice have been developed, and use of such knockout mice as an important tool for elucidating the influence on development or homeostasis at the cellular level and the roles of P450 regarding in vivo toxicity of drugs or chemical substances is expected (McKinnon et al., Clin. Exp. Pharmacol. Physiol., 25: 783, 1998). For example, two research groups constructed knockout mice lacking endogenous Cyp1a2 (Pineau et al., Proc. Natl. Acad. Sci. U.S.A., 92: 5134, 1995). The Cyp1a2 knockout mice prepared by Pineau et al. (Pineau et al., Proc. Natl. Acad. Sci. U.S.A., 92: 5134, 1995) were normal when the resulting mice were heterozygous; however, they died immediately after birth when they were homozygous. Meanwhile, the Cyp1a2 knockout mice constructed by Liang et al. (Liang et al., Proc. Natl. Acad. Sci. U.S.A., 93: 1671, 1996) did not show any abnormalities in the phenotypes of homozygotes. Such difference is considered to result from different sequences of genes to be deleted. Also, the influence of lacked P450 gene and abnormality of metabolism found using the Cyp1a2 knockout mice have been reported (e.g., Genter et al., Biochem. Pharmacol., 55: 1819, 1998), and the role of Cyp1a2 in the metabolism system has been elucidated with the use of the knockout mice. Knockout mice lacking Cyp2e1, which is known as a major enzyme for metabolizing ethanol, were constructed (Lee et al., J. Biol. Chem., 271: 12063, 1996). Cyp2e1 is known to be involved with metabolism of acetaminophen, acetone, or arachidonic acid, in addition to ethanol. Homozygotes that completely lack Cyp2e1 were not different from wild-type mice in appearance; however, resistance to acetaminophen was improved, and the results of pathological observation suggested that Cyp2e1-mediated metabolism is significantly involved with acetaminophen-induced hepatic toxicity. All of these P450 gene knockout mice were created for the purpose of elucidating functions of such gene by knocking-out the gene of interest, and an increase in the expression level of the introduced foreign P450 gene is not intended.

Meanwhile, Herwaarden et al. produced knockout mice lacking the Cyp3a gene, they further produced mice comprising a human CYP3A4 gene expressed in the liver or small intestine, and they reported research regarding docetaxel metabolism. In these mice, however, the human CYP3A4 gene was ligated to a site downstream of a liver- or small-intestine-specific promoter and forced to express, and thus, such mice would not physiologically reproduce expression levels in humans (Herwaarden et al., J. Clin. Invest., 117: 3583-3592, 2007).

Under such circumstances, for example, WO 01/011951 discloses that a partial fragment of a human normal fibroblast-derived chromosome 7 is introduced into a mouse ES cell (embryonic stem cell) by means of a microcell method, and a chimeric mouse that harbors the human chromosome fragment in normal tissues and expresses a human CYP3A4 gene in the liver and small intestine by induction with a drug is obtained with the use of such ES cells. In this connection, WO 01/011951 discloses the #7-HAC vector obtained by translocating a human chromosome 7 fragment (approximately 5 Mb) comprising the CYP3A gene (hereafter such genes may be referred to as the “CYP3A gene cluster”) to the SC20-HAC vector (FERM BP-7583; JP Patent Publication (kokai) 2005-230020 A), although such vector is incapable of gene transmission to progeny. Further, WO 01/011951 discloses the creation of mice comprising human P450 gene (belonging to CYP3A family) and of mice with disrupted murine endogenous P450 gene (belonging to Cyp3a family).

As disclosed in WO 01/011951, a mouse retaining a partial human chromosome 7 fragment comprising human CYP3A gene or an approximately 5 Mb region of human chromosome 7 comprising human CYP3A gene was introduced into a human artificial chromosome vector (SC20), which is known to be stable in mice, to prepare a mouse retaining the human artificial chromosome vector, although stable transmission of the gene from a chimeric mouse to progeny was impossible. If a mouse that can transmit a gene to progeny cannot be obtained, then a mouse must be produced from a chimeric mouse, indicating that embryo manipulation is necessary each time and mice having homogeneous genetic background cannot be obtained. Further, this means that progeny mice into which a plurality of human P450 genes of interest have been introduced and in which endogenous drug-metabolizing enzymes have been disrupted cannot be obtained. As a cause that the human CYP3A genes are not transmitted from a chimeric mouse retaining the human CYP3A genes disclosed in WO 01/011951 to progeny, it has been reported that over-expression of genes involved in genomic imprinting or genes that are important for development and germ cell differentiation would lead to embryonic lethality (Okita et al., Genomics., 81 (6): 556, 2003; Sun F L, Dean W L, Kelsey G, Allen N D, Reik W.: Transactivation of Igf2 in a mouse model of Beckwith-Wiedemann syndrome, Nature, 1997 Oct. 23; 389 (6653): 785, 787; and Puech et al., Proc. Natl. Acad. Sci. U.S.A., 97: 10090, 2000).

In contrast, the human artificial chromosome vector (which, hereafter, may be referred to as the "HAC vector") is advantageous in that: for example, 1) it is independently maintained without being inserted into the host chromosome and it thus does not disrupt host genes; 2) it is stably retained at a given copy number, it is influenced by physiological expression control of a host cell, and neither overexpression of an introduced gene nor lost expression of the gene is caused; and 3) the size of a DNA that can be introduced is not restricted, and, thus, a gene containing an expression control region or a plurality of genes/isoforms can be introduced. As described above, because the human artificial chromosome vector has advantages that conventional vectors (i.e., virus, YAC, BAC, PAC, cosmid, and plasmid vectors) do not have, the human artificial chromosome vector is expected to function as a vector used for analyzing functions of novel genes or as a system for creating a human-type animal model (e.g., Kuroiwa et al., Nature Biotech., 18: 1086, 2000; and Tomizuka et al., Proc. Natl. Acad. Sci. U.S.A., 97: 722, 2000).

DISCLOSURE OF THE INVENTION

An object of the invention is to produce a transchromosomic animal that is capable of transmitting a gene of interest to progeny by removing a gene that is considered to be important for development and germ cell differentiation, from human chromosome 7, cloning a certain gene region comprising human P450 (CYP3A) genes into a human artificial chromosome vector, and introducing the gene region into a non-human mammalian animal. Thus, the human artificial chromosome vector that retains a human chromosome 7 fragment containing the human cytochrome P450 genes and is transmittable to progeny, as well as non-human mammalian animals (such as rodents and ungulates) retaining the vector, can be obtained.

Another object of the invention is to provide a method for testing a pharmacological effect or metabolism of a drug or food product using said non-human mammalian animal or said tissue, organ, or cell thereof.

The present inventors conducted intensive studies in order to achieve the above-described objects. As a result, the present inventors have now found that a transchromosomic mouse that is transmittable to progeny could be obtained by deleting human chromosome 7 at AC073842 located on the telomere side of a human CYP3A gene cluster, and inserting a loxP sequence into AC004922 located on the centromere side of the human CYP3A gene cluster, thereby cloning a given gene region (approximately 1 Mb±500 Kb) of human chromosome 7 containing human P450 (CYP3A) genes from which genes that are considered to be important for development and germ cell differentiation have been removed, into the human artificial chromosome vector, and introducing the human artificial chromosome vector into a mouse, which is a non-human mammalian animal. This has led to the completion of the invention.

SUMMARY OF THE INVENTION

Accordingly, the present invention is summarized as follows.

(1) A mammalian artificial chromosome vector that retains a human chromosome 7 fragment comprising human cytochrome P450 genes and is transmittable to progeny, wherein the human chromosome 7 fragment retains a region of approximately 1 Mb±500 Kb in size comprising at least a human CYP3A gene cluster, which region is located between chromosome markers AC004922 and AC073842.

(2) The mammalian artificial chromosome vector according to (1), which is a human artificial chromosome vector.

(3) The mammalian artificial chromosome vector according to (2), wherein the human artificial chromosome vector is obtained by translocating the human chromosome 7 fragment to the SC20 vector derived from human chromosome 14 (FERM BP-7583).

(4) The mammalian artificial chromosome vector according to (2), wherein the human artificial chromosome vector is CYP3A-HACΔ retained by a chicken DT40 cell line, DT40 (CYP3A-HACΔ) 214 (Accession Number: FERM BP-10928).

(5) A pluripotent cell derived from a non-human mammalian animal, which retains the mammalian artificial chromosome vector according to any of (1) to (4) and enables expression of the human cytochrome P450 genes.

(6) The pluripotent cell according to (5), which is a mouse ES cell.

(7) A non-human mammalian animal, which retains the mammalian artificial chromosome vector according to any of (1) to (4) and enables expression of human cytochrome P450 genes.

(8) The non-human mammalian animal according to (7), which is a chimeric animal or a progeny thereof.

(9) The non-human mammalian animal according to (8), wherein the progeny is obtained by crossing the chimeric animal with an allogeneic wild-type animal.

(10) The non-human mammalian animal according to any of (7) to (9), wherein the native cytochrome P450 genes of the non-human mammalian animal, which is a homolog of the human CYP3A gene cluster, is disrupted so that the expression of the native cytochrome P450 gene is reduced or lost.

(11) The non-human mammalian animal according to any of (7) to (10), which is a mouse.

(12) The non-human mammalian animal according to (11), wherein the mouse is a progeny mouse.

(13) A mouse or progeny thereof, which is produced by crossing the mouse or progeny thereof according to (11) or (12) with a mouse lacking a mouse Cyp3a gene cluster, characterized in that it retains the mammalian artificial chromosome vector according to any of (1) to (4), that it lacks the mouse Cyp3a gene cluster, and that it enables expression of human cytochrome P450 genes.

(14) A cell or an organ or tissue containing the cell, characterized in that it is derived from the non-human mammalian animal according to any of (7) to (12) or the mouse or progeny thereof according to (13) and that it enables expression of human cytochrome P450 genes.

(15) A method for preparing biologically active human cytochrome P450 comprising expressing human cytochrome P450 genes in the non-human mammalian animal according to any of (7) to (12), the mouse or progeny thereof according to (13), or the cell, organ, or tissue according to (14) to produce the biologically active human cytochrome P450, and recovering the produced human cytochrome P450.

(16) A method for testing pharmacological effects and/or metabolism of drug or food products comprising administering drugs or food products to the non-human mammalian animal according to any of (7) to (12), the mouse or progeny thereof according to (13), or the cell, organ, or tissue according to (14) and measuring pharmacological effects and/or metabolism of the drugs or food products.

(17) A pluripotent cell derived from a non-human mammalian animal retaining the mammalian artificial chromosome vector according to any one of (1) to (4), characterized in that the native cytochrome P450 genes of the non-human mammalian animal, which is a homolog of the human CYP3A gene cluster, are disrupted so that the expression of the native cytochrome P450 genes are reduced or lost.

(18) The pluripotent cell according to (17), which is an ntES cell.

(19) The pluripotent cell according to (17) or (18), which is a mouse-derived ntES cell.

DEFINITION

The terms used herein are defined as follows.

The term "mammalian artificial chromosome vector" used herein refers to an artificial chromosome prepared based on a mammalian animal chromosome. For example, an artificial chromosome prepared based on a human chromosome is referred to as a "human artificial chromosome."

The term "human CYP3A gene cluster" used herein refers to CYP3A genes located on human chromosome 7. Examples of CYP3A genes include CYP3A4, CYP3A7, CYP3A5, and CYP3A43.

The term "human cytochrome P450 gene(s)" used herein is a generic term for human CYP genes. Examples thereof include CYP3A4, CYP2E1, and CYP2D6.

The term "mouse Cyp3a gene cluster" used herein refers to Cyp3a genes located on mouse chromosome 5. Examples of Cyp3a genes include Cyp3a11, Cyp3a25, and Cyp3a13.

The term "homolog" used herein refers to a homologous gene of other animal species corresponding to any gene. For example, a mouse homolog of the human CYP3A4 gene is Cyp3a11. Regarding the CYP genes, numbers following alphabetic letters often differ among different animal species.

The term "ntES cell" used herein refers to a nuclear transfer ES cell prepared via nuclear transplantation from the donor cell nucleus to the enucleated recipient egg.

The term "non-human mammalian animal" used herein refers to primates such as a monkey or chimpanzee, rodents such as mice, rats, hamsters, or guinea pigs, and ungulates such as cattle, pigs, sheep, or goats, although examples of non-human mammalian animals are not limited thereto.

This description includes all or part of the contents as disclosed in the description and/or drawings of Japanese Patent Application No. 2007-295993, which is a priority document of the present application.

BRIEF DESCRIPTION OF THE DRAWINGS

FIG. 3*a* shows a DT40 (#7) clone, FIG. 3*b* shows a DT40 (DF141) clone, FIG. 3*c* shows a DT40 (NP25) clone, FIG. 3*d* shows an R clone, FIG. 3*e* shows an RP13 clone, FIG. 3*f* shows an RPC13F2 clone, FIG. 3*g* shows a CHO clone, and FIG. 3*h* shows a TT2F clone.

FIG. 23A shows the results of measurement in a human, FIG. 23B shows the results of measurement in a mouse (wild-type), FIG. 23C shows the results of measurement in the Δcyp mouse, and FIG. 23D shows the results of measurement in the TC(CYP3A-HACΔ)/Δcyp mouse.

BEST MODE FOR CARRYING OUT THE INVENTION

Figure 1:
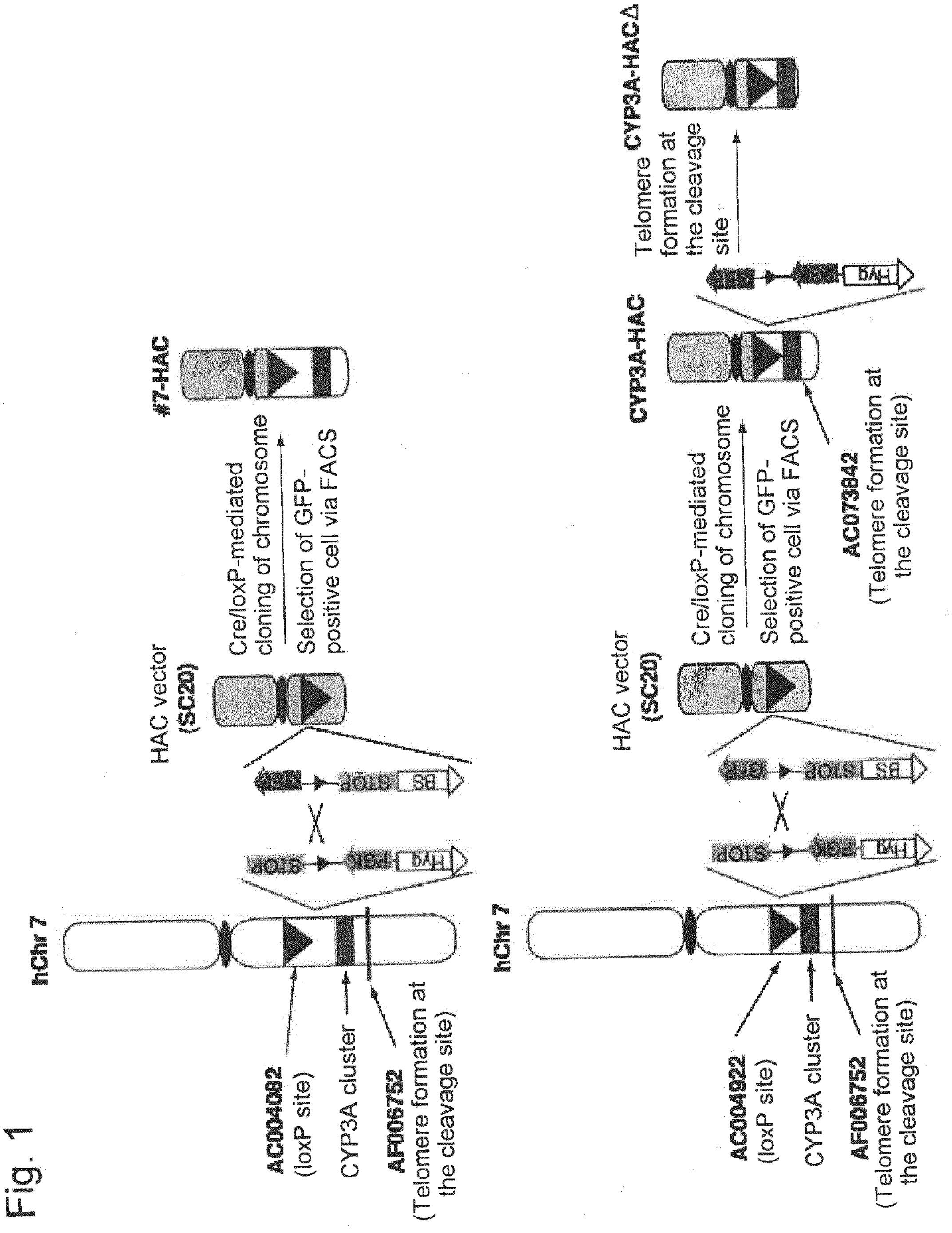
FIG. 1 schematically shows a method for preparing #7-HAC, CYP3A-HAC, and CYP3A-HACΔ.

The present invention is described in greater detail.

An aspect of the present invention provides a mammalian artificial chromosome vector that retains a human chromosome 7 fragment comprising human cytochrome P450 genes and is transmittable to progeny, wherein the human chromosome 7 fragment retains a region (approximately 1 Mb±500 Kb) at least comprising the human CYP3A gene cluster located between chromosome marker AC004922 and chromosome marker AC073842.

The term "cytochrome P450" used herein is a generic term for the hydroxylase family, the members of which are enzymes having effects of hydroxylating various substrates (i.e., biological activity). Cytochrome P450 is present mainly in the livers of animals and it is involved in, for example, detoxication of substances, metabolism of fatty acids, and biosynthesis of steroidal hormones. In this description, "cytochrome P450" may be simply referred to as "P450."

The genes of the CYP3A molecular species of the human cytochrome P450 gene are present in the CYP3A gene cluster in 7q21 to q22 on the long arm of human chromosome 7 (e.g., B. A. Brooks et al., Am. J. Hum. Genet., 43: 280, 1988). When preparing the mammalian artificial chromosome vector that is transmittable to progeny of the present invention, a particularly useful region comprising the CYP3A gene cluster is a human chromosome 7 fragment composed of a region of approximately 1 Mb±500 Kb, preferably approximately 1 Mb±300 Kb, and more preferably approximately 1 Mb±200 Kb, which comprises at least the human CYP3A gene cluster located between chromosome marker AC004922 and chromosome marker AC073842 on the long arm of human chromosome 7. In particular, the region from AC004922 to AC073842 (e.g., J. E. Sulston et al., Genome Res., 8: 1097, 1998) has a size of approximately 1 Mb, and a region in the vicinity thereof containing said region does not contain a genome-imprinting gene cluster that may cause embryonic lethality, developmental anomaly, or malformation, and such region does not contain a gene(s) that may be important for germ cell differentiation causing infertility.

When the mammalian artificial chromosome vector of the present invention is introduced into a non-human mammalian animal, such vector can be present independently from a chromosome inherent to, or native for, the animal. Since the resulting transchromosomic animal retains the human P450 genes, such heterozygous gene can be expressed, and the above vector is transmittable to progeny via crossing. In this regard, the mammalian artificial chromosome vector of the present invention is superior to the human artificial chromosome vector (#7-HAC) disclosed in WO 01/011951 in terms of percentages of chimerism and chromosome retention. Further, the vector of the present invention is transmittable to progeny. In contrast, the known #7-HAC vector could not be transmitted to progeny.

The mammalian artificial chromosome vector of the present invention can comprise centromere, telomere, and subtelomere regions derived from an arbitrary chromosome of a mammalian animal, in addition to a given region comprising the human CYP3A gene cluster. Examples of mammalian animals include, but are not limited to, primates such as human, monkey, or chimpanzee, rodents such as mice, rats, hamsters, or guinea pigs, and ungulates such as cattle, pigs, sheep, or goats. The aforementioned centromere is derived from a mammalian animal chromosome, preferably from any of human chromosomes, and more preferably from human chromosome 14. The aforementioned telomere and subtelomere regions are derived from a mammalian animal chromosome, preferably from a human chromosome, more preferably from human chromosome 7 or 14, and further preferably from an artificially synthesized repeat sequence of the TTAGGG sequence. Further, the vector of the present invention can comprise the MDR1 gene cluster derived from a mammalian animal chromosome, preferably from a human chromosome, and more preferably from human chromosome 7. A preferable example of the mammalian artificial chromosome vector of the present invention is a human artificial chromosome vector.

According to an embodiment of the present invention, the human artificial chromosome vector was obtained by translocating the human chromosome 7 fragment into the SC20 vector derived from human chromosome 14 (Accession Number of international deposition: FERM BP-7583; JP Patent Publication (kokai) No. 2005-230020 A). The term "translocation" refers to the transfer of a part of a given chromosome to another chromosome.

According to another embodiment of the present invention, the human artificial chromosome vector is CYP3A-HACΔ retained within a chicken DT40 cell line, DT40 (CYP3A-HACΔ)214 (Accession Number: FERM BP-10928). This cell line has been internationally deposited at the International Patent Organism Depositary of the National Institute of Advanced Industrial Science and Technology (Tsukuba Central 6, 1-1-1 Higashi, Tsukuba, Ibaraki, 305-8566, Japan) as of Oct. 30, 2007, under the accession number: FERM BP-10928.

Hereafter, examples of construction of the mammalian artificial chromosome vector of the present invention and a non-human mammalian animal retaining the same and examples of use thereof are described.

Specifically, a human artificial chromosome retaining a human chromosome 7 fragment (hereafter it is referred to as "CYP3A-HAC" or "CYP3A-HACΔ") that is constructed in order to stably and efficiently express the CYP3A genes on human chromosome 7 in a non-human mammalian animal, such as a mouse, is disclosed. Construction and structure of CYP3A-HAC or CYP3A-HACΔ are described in the examples below, FIG. 1, and FIG. 2.

(i) Modification of Human Chromosome 7

The human CYP3A gene cluster is located in 7q21.3-q22.1 on chromosome 7 (B. A. Brooks et al., as above). The human CYP3A family includes at least CYP3A4, CYP3A5, CYP3A7, and CYP3A43, and the genomic sequence of CYP3A is registered under GenBank Accession No. NG_000004. Human P450 of the present invention includes P450 enzymes of the CYP3A family, such as CYP3A4, CYP3A5, CYP3A7, and CYP3A43 enzymes.

A fragment containing the CYP3A gene cluster on human chromosome 7 can be used for constructing a novel human artificial chromosome by translocating and cloning such fragment into a chromosome fragment (SC20-HAC vector) derived from human chromosome 14, for transmitting such human artificial chromosome to mouse progeny, and for producing transchromosomic, non-human mammalian animals (e.g., mammalian animals such as rodents and ungulates) retaining such human artificial chromosome.

The term "mammalian artificial chromosome" used herein refers to an artificial chromosome that is prepared by translocating a given region on a mammalian animal chromosome into a stable chromosome fragment (a chromosome vector) derived from a mammalian animal of the same or different species. The term "transchromosomic, non-human mammalian animal" refers to a mammalian animal other than a human, which is obtained via transmission of a heterozygous chromosome fragment through a germ line.

The present inventors have considered that, when preparing a mammalian artificial chromosome, it is preferable that a chromosome region, which is deduced to adversely affect the development of an animal such as a mouse into which the chromosome has been introduced, be removed from the chromosome insert to as great an extent as possible, so as to avoid such adverse influence. In the past, however, there was no or insufficient information regarding relevant structures, such as a detailed sequence of human chromosomes. Thus, it was sometimes difficult to insert, for example, the loxP sequence and a human telomeric sequence in the vicinity of the target gene. In such a case, a region sandwiched by these sequences contains many other genes in addition to the target gene. When such excessive genes are introduced into a non-human mammalian animal, such as a mouse, accordingly, such genes may adversely affect the development of individuals or germ cell differentiation. Further, the correlation between the size of a chromosome insert containing a target gene and the percentage of chimerism of an animal into which the chromosome has been introduced, the percentage of retention of the introduced chromosome, or the percentage of gene transmission was not clear.

Based on information regarding the structure of human chromosome 7 in which the CYP3A gene cluster is present, the present inventors discovered that the percentage of chimerism of an animal into which the chromosome has been introduced, the percentage of retention of the introduced chromosome, and the percentage of gene transmission would be significantly enhanced for a chromosome insert containing a CYP3A gene cluster of a given size. By removing excessive genes from the human artificial chromosome, a novel human artificial chromosome retaining a region in the vicinity of the given CYP3A gene cluster region as an insert was constructed. In this description, the term “excessive genes” refers to toxic genes that adversely affect the development of an animal into which the chromosome has been introduced or germ cell differentiation. Examples thereof include the causal region of a genetic disease that is dependent on imprinting genes or gene expression levels, and genes expressed in germ cells.

It is known that overexpression of genes involved in genomic imprinting leads to embryonic lethality, developmental anomaly, and malformation, for example. Since the genome imprinting gene cluster is present in 7q22 (which is closer to the centromere than the CYP3A gene cluster) on human chromosome 7, in which the CYP3A gene cluster is present, deletion thereof is considered preferable. Also, overexpression of genes expressed in germ cells, such as spermaries or ovaries, is known to adversely affect germ cell differentiation. Since a plurality of genes expressed in germ cells are present in 7q22 (i.e., a site closer to the telomere than the CYP3A gene cluster) on human chromosome 7 in which the CYP3A gene cluster is present, deletion thereof is considered preferable. As a result, a size of the entire CYP3A gene cluster region can be reduced, and this can produce a high percentage of gene transmission.

When the human chromosome 7 fragment comprising the CYP3A gene cluster is translocated to the SC20-HAC vector in (ii) below, the size of the chromosome insert to be translocated (including the CYP3A gene cluster region on human chromosome 7) is smaller than 5 Mb, which is the size in the case of #7-HAC (WO 01/011951). Such size may generally be approximately 4 Mb to approximately 0.5 Mb, preferably approximately 3 Mb to approximately 0.5 Mb, further preferably approximately 2 Mb to approximately 0.5 Mb, and most preferably approximately 1 Mb to approximately 0.5 Mb. The results of an experiment for deleting excessive genes demonstrate that the centromere side end of the chromosome insert to be translocated is preferably the AC004922 locus and the telomere side end of the chromosome insert is preferably the AC073842 locus. That is, the 7q22 genomic imprinting gene cluster is removed, and a loxP sequence, which is a recognition sequence for the Cre recombinase, is inserted via homologous recombination into a site of the chromosome (e.g., AC004922; see the NCBI database) located at the centromere side of the CYP3A gene cluster; and a gene expressed in a germ cell located in 7q22 is removed, and a human telomeric sequence is inserted via homologous recombination into a site of the chromosome (e.g., AC073842; see the NCBI database) located at the extreme telomere side of the CYP3A gene cluster, and the resultant is cleaved in a manner that is more specific for the site of interest (i.e., telomere truncation) (Kuroiwa et al., Nucleic Acid Research, 26: 3447, 1998). Thus, the AC004922-CYP3A gene cluster (i.e., the AC073842 fragment) can be prepared, and the resultant can be used for constructing the artificial chromosome vector of the present invention.

(ii) Translocation of a Human Chromosome 7 Fragment Containing the CYP3A Gene Cluster to the SC20-HAC Vector by the Cre-loxP System For example, a loxP sequence and a human telomeric sequence are inserted via homologous recombination into sites in the vicinity of the target gene region on the human chromosome, and only a region in the vicinity of the target gene region sandwiched by such sequences is translocated specifically into a corresponding loxP sequence insertion site on another chromosome fragment, which is preferably stable and transmittable to progeny, such as the human chromosome 14-derived SC20 chromosome vector (SC20-HAC vector). Thus, a human artificial chromosome (HAC) retaining only a region in the vicinity of the target gene region as an insert (i.e., a chromosome insert) can be prepared (Kuroiwa et al., Nature Biotech., 18: 1086, 2000).

In such a case, the size of a chromosome insert to be translocated (containing a CYP3A gene cluster region on human chromosome 7) is smaller than 5 Mb, which is the size in the case of #7-HAC (WO 01/011951), as described above. Such size may generally be approximately 4 Mb to approximately 0.5 Mb, preferably approximately 3 Mb to approximately 0.5 Mb, further preferably approximately 2 Mb to approximately 0.5 Mb, and most preferably approximately 1 Mb to approximately 0.5 Mb. The centromere side end of the chromosome insert to be translocated is preferably the AC004922 locus, and the telomere side end the chromosome insert is preferably the AC073842 locus (J. E. Sulston et al., as above).

Methods for constructing the human artificial chromosome of the present invention are described in greater detail.

Human chromosome 7 comprising the human CYP3A gene cluster or a fragment thereof can be obtained by well-known techniques. Specifically, a human chromosome or a fragment thereof can be prepared to result in a library of mouse A9 cells by the microcell method (Koi et al., Jpn. J. cancer Res., 80: 413-418, 1989). A sequence specific for the human CYP3A gene cluster can be detected from said library via PCR or other means, so that clones having human chromosome 7 or fragments thereof can be selected. Human chromosome 7 or fragments thereof can be more preferably introduced into a chicken DT-40 cell (RIKEN Cell Bank, Japan: RCB 1464; ATCC CRL-2111) by the microcell method, for the convenience of later modification.

Figure 2:
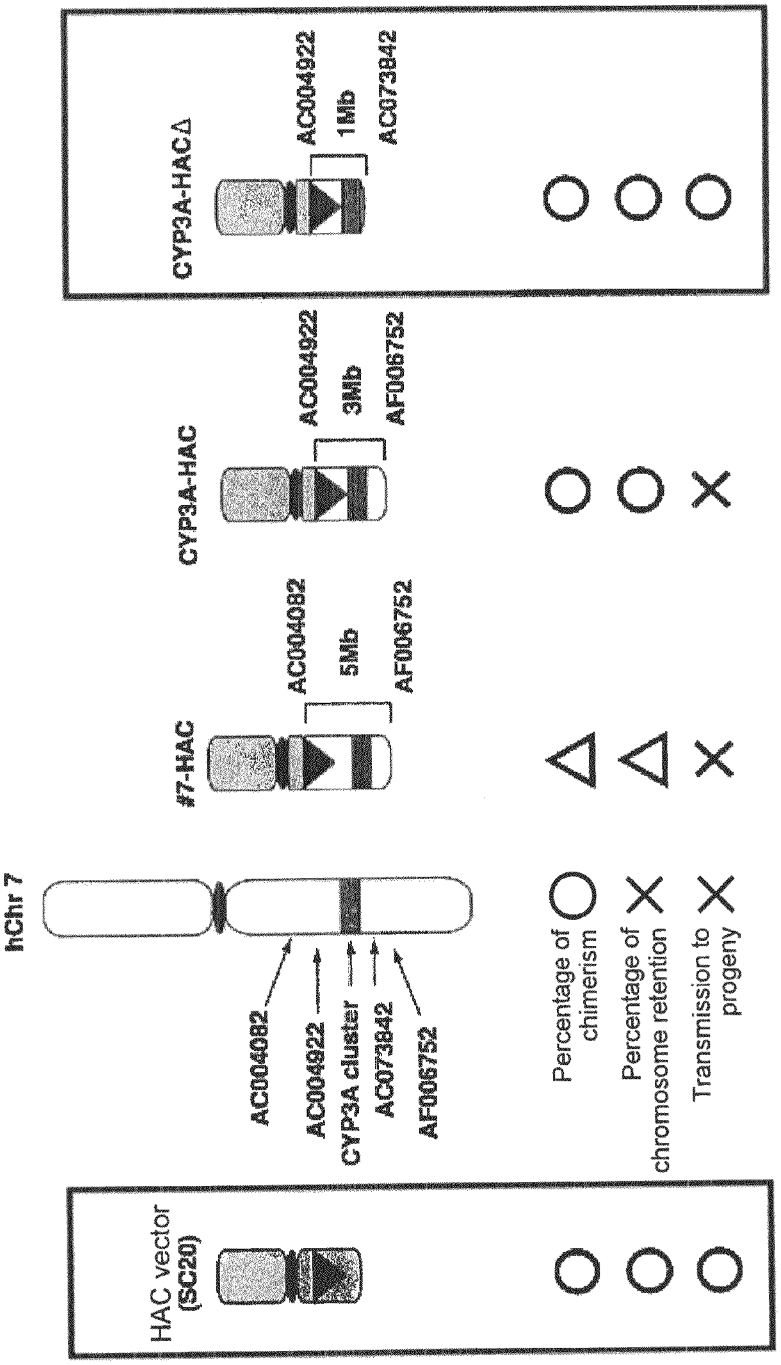
FIG. 2 shows a summary of #7-HAC-, CYP3A-HAC-, and CYP3A-HACΔ-retaining regions, percentages of chimerism thereof, percentages of retention, and percentages of gene transmission to progeny.

The human CYP3A gene cluster is present in 7q22 on human chromosome 7 (B. A. Brooks et al., as above). A 5-Mb region from the AC004082 locus to the AF006752 locus of the #7-HAC vector was translocated and cloned as the chromosome insert. This 5-Mb insert comprises an extra 2-Mb chromosome region in a region at the telomere side of the CYP3A gene cluster region and an extra 2-Mb chromosome region in a region at the centromere side thereof. This insert further comprises an imprinting gene cluster in the 2-Mb region at the centromere side. Furthermore, a plurality of genes expressed in germ cells are present in the 2-Mb region at the telomere side. In order to first remove the 2-Mb region at the centromere side, a chromosome 7 fragment (which is telomeretruncated at the AF006752 locus) is inserted into the AC004922 locus (J. E. Sulston et al., as above), which is very close to the CYP3A gene cluster region and is at approximately 300 Kb from the CYP3A gene cluster region toward the centromere, i.e., at a loxP sequence, by means of homologous recombination. By such modification, the AC004922-CYP3A gene cluster-AF006752 fragment (approximately 3 Mb) can be selectively translocated and cloned into the SC20-HAC vector as the chromosome insert. The resulting artificial chromosome vector is CYP3A-HAC (FIG. 1 and FIG. 2).

Subsequently, this chromosome vector is cleaved via telomere truncation (e.g., Kuroiwa et al. (1998), ibid) at the AC073842 region (J. E. Sulston et al., ibid), which is very close to the CYP3A gene cluster region and is at approximately 200 Kb from the CYP3A gene cluster region toward the telomere, so that the fragment of AC004922-CYP3A gene cluster-AC073842 (approximately 1 Mb) can be selectively translocated and cloned into the SC20-HAC vector as the chromosome insert. The resulting human chromosome vector is CYP3A-HACΔ (FIG. 1 and FIG. 2). More specifically, CYP3A-HACΔ is cleaved at 124455 in AC073842, and thus, the genomic region is located in a region from 124456 to 132764 of AC073842, and the region from 1 to 124455 is not present. Also, since it is translocated at 32340 of AC004922, the genomic region is present in a region from 1 to 32340 of AC004922, and a region from 32341 to 82359 is not present.

The present invention, however, is not limited to a human chromosome 7 fragment composed of a given region as described above, provided that such fragment does not comprise toxic regions, such as the genomic imprinting gene cluster or a gene(s) deduced to be important for germ cell differentiation, and provided that it comprises the human CYP3A gene cluster.

When preparing CYP3A-HAC and CYP3A-HACΔ, telomere truncation in a chicken DT40 cell and interchromosomal translocation using Cre-loxP system can be performed.

At the outset, DT40 cells retaining a modified human chromosome 7 fragment and the modified SC20-HAC vector (Kuroiwa et al., as above, 2000) obtained in the manner described above are constructed. In order to translocate the human chromosome 7 fragment comprising CYP3A gene cluster to the SC20-HAC vector using the Cre-loxP system, DT40 cells retaining modified human chromosome fragments are then fused to each other to construct a DT40 cell hybrid retaining two modified human chromosome fragments. Subsequently, the Cre recombinase is expressed in the DT40 cell hybrid for translocation. However, it has been reported that the frequency of recombination (or translocation) between two non-homologous chromosomes is very low (e.g., A. J. Smith et al., Nature Genet., 9: 376, 1995). According to the present invention, further, translocation takes place between exogenous human chromosomes instead of between endogenous chromosomes. This may further lower the recombination efficiency. Thus, a positive selection system that can select cells in which recombination has taken place between loxPs as expected is preferably used. In cells in which chromosome translocation has taken place between loxP sequences, accordingly, a system for cloning a target cell via GFP gene expression and sorting via FACS is employed. In order to enhance recombination frequency, further, Cre recombinase is expressed stably instead of transiently. Since translocation between two chromosomes takes place mutually, stable expression of Cre recombinase may cause the translocated chromosomes to undergo recombination (or translocation) again and return to the original state, although the frequency of recombination is low. In such experiment, in general, Cre recombinase is expressed transiently, or expression of Cre recombinase is strictly controlled. In the present invention, however, the target translocated human artificial chromosome is transferred to the Chinese hamster ovary (CHO) cells by the microcell fusion method immediately after translocation in the DT40 hybrid. Accordingly, CHO cells would not be influenced by Cre recombinase. This simply enables stable expression of Cre recombinase.

A human chromosome fragment having any size (exceeding the YAC vector cloning size) can be cloned into the loxP site on the stable SC20-HAC vector by the above-described techniques.

CYP3A-HAC or CYP3A-HAC4 constructed by the above system for human artificial chromosome construction should be introduced into a Chinese hamster ovary (CHO) cell before it is introduced into a mouse ES cell. Dieken et al. (Nature Genet., 12: 174, 1996) transferred a modified human chromosome from a chicken DT40 cell to a mouse MEL cell (a type of cancer cell), and most of the chromosome was transferred in the form of fragments. In order to avoid such fragmentation, a human chromosome may be transferred into a Chinese hamster ovary (CHO) cell, so that it can be transferred undamaged. The CHO cell is known to efficiently form microcells, as with mouse A9 cell (Kuroiwa et al. (2000), ibid). Thus, a modified human chromosome can be transferred from CHO cells to pluripotent cells of a non-human mammalian animal (e.g., ES cells), and a chimeric animal retaining CYP3A-HAC or CYP3A-HACΔ can be constructed.

(iii) Transfer of Artificial Chromosome Comprising Human P450 Gene (i.e., CYP3A Gene Cluster) into Pluripotent Cell The present invention further provides a pluripotent cell derived from a non-human mammalian animal retaining the above-described mammalian artificial chromosome vector and capable of expressing the human cytochrome P450 gene.

Herein, examples of pluripotent cells include undifferentiated cells that are differentiated into or altered (or differentiated) to somatic cells having various forms or functions via injection into early embryos of non-human mammalian animals, such as embryonic carcinoma cells (EC cells, Hanaoka et al., Differentiation, 48: 83, 1991), embryonic stem cells (ES cells, Evans et al., Nature, 292: 154, 1981), embryonic germ cells (EG cells, Matsui et al., Cell, 70: 841, 1992), nuclear transplantation-derived embryonic stem cells (ntES cells, Wakayama et al., Science, 292: 740, 2001), spermary-derived pluripotent stem cells (mGS cells, Kanatsu-Shinohara et al., Cell, 119: 1001, 2004), or induced pluripotent stem cells (iPS cells, Takahashi et al., Cell, 126: 663, 2006), or alternatively by culture with the early embryo. For example, the capacity of ES cells, ntES cells, or iPS cells for differentiation is particularly high, such capacity often contributes to germ cells, and progeny can be obtained from such cells. The EC cells are obtained mainly from germ cell cance. The ES cells are obtained from embryoblasts of blastocysts. The EG cells are obtained from primordial germ cells that appear at the initial stage of development. The ntES cells are obtained from embryoblasts of blastocysts resulting from nuclear transplantation of donor nuclei to enucleated unfertilized eggs. The mGS cells are obtained from spermary-derived stem cells. The iPS cells are obtained by introducing DNAs encoding 2, 3, or 4 given factors (e.g., klf4, oct4; klf-4, oct4 and sox2; klf-4, oct4, c-myc and sox2; etc.) into somatic cells such as fibroblasts derived from a mammalian animal such as a mouse.

Among pluripotent cells, in particular, mouse ES cells are well known, and thus, mouse ES cells are preferably used in the present invention. EStablishment of ES cells or pluripotent cells in animal species other than a mouse has been reported for a rat (Iannaccone et al., Dev. Biol., 163: 288, 1994) and for a pig (Wheeler et al., Reprod. Fertil. Dev., 6: 563, 1994). Also, use of iPS cells, which are known as ES-like cells, is preferable. Accordingly, a human artificial chromosome may be transferred to recipient cells, such as ES, iPS, or pluripotent cells, so that non-human animals retaining a human artificial chromosome or a fragment thereof and expressing a gene on the human artificial chromosome can be constructed, as in the case of a mouse. Further, such non-human mammalian animal may be used to express the human CYP3A gene cluster. When the human artificial chromosome cannot be transmitted to progeny of such non-human animals, a gene corresponding to a homologous gene of the human P450 gene in a non-human-animal-derived pluripotent cell may be disrupted, and the aforementioned human artificial chromosome may be introduced. Thus, a pluripotent cell that lacks the endogenous P450 gene derived from a non-human animal and can express the human CYP3A gene cluster, can be obtained.

In the present invention, the pluripotent cell lines described above can be used as recipient cells into which a chromosome fragment comprising the human P450 gene is to be transferred.

As a chromosome donor cell retaining a labeled chromosome fragment comprising the human P450 gene, a cell 1) retaining a human chromosome labeled with a marker that can be selected with a recipient cell, 2) containing no other human chromosome, and 3) having a high capacity for microcell formation, is preferable.

Regarding human chromosome donor materials, any cell lines, cancer cells, or primary cultured human cells can be used. Normal fibroblasts are preferable from the viewpoint of a low risk of abnormalities, such as chromosome deletion or amplification and ease of culture. Regarding 1) above, a human cell can be transformed with a vector expressing a marker gene for resistance to a drug (e.g., G418, puromycin, hygromycin, or blasticidin), for example. A promoter used for regulating marker expression that can efficiently function in a recipient cell, such as a mouse ES cell, as well as in a human cell, is preferable. To this end, a ligation of SV40 enhancer and herpes simplex virus thymidine kinase promoter (Katoh et al., Cell Struct. Funct., 12: 575, 1987), mouse PGK-1 promoter (Soriano et al., Cell, 64: 693, 1991), or the like, can be used. With the use of a DNA fragment comprising said marker gene and a marker gene comprising a promoter ligated thereto where needed, a cell that transforms a human cell and expresses a marker gene is selected via electroporation (Ishida et al., *Saibo Kogaku Jikken Sousa Nyumon* (Introduction to Cell Engineering Experimental Protocols), Kodansha (Japan), 1992) or other means. Thus, a library of human cell transformants comprising the introduced marker genes randomly inserted onto 23 of the 46 human chromosomes can be obtained. Regarding 3) above, many normal human cells have a very low capacity for microcell formation. Thus, the aforementioned transformants may be subjected to complete cell fusion with cells having the high capacity for microcell formation, such as mouse A9 cell (Koi et al., Jpn. J. Cancer Res., 80: 413-418, 1989), to impart the capacity for microcell formation.

As materials for transferring a human chromosome fragment into a recipient cell, microcells prepared from a human chromosome 7 donor cell comprising the human P450 gene or microcells irradiated with gamma rays can be used. A human chromosome fragment is transferred into a recipient cell via fusion between a recipient cell and a microcell by the method described in *Saibo-Kogaku Handbook* (Cell Engineering Handbook), Motoyuki Shimizu, Yodosha (Japan), 1992, for example. A microcell donor cell retains a marker that can select a chromosome comprising the human P450 gene or a fragment thereof in a recipient cell. A cell line retaining the human P450 gene or a chromosome fragment comprising the human P450 gene may be selected therefrom by PCR, Southern blot analysis, FISH analysis, or other means using primers based on specific gene markers or polymorphism markers or fluorescence-labeled probes, so that a chromosome fragment comprising the human P450 gene can be introduced. Also, a plurality of chromosome fragments comprising the P450 gene retaining different selection markers may be successively introduced, and recipient cells retaining all such fragments can be obtained. The fact that a recipient cell selected by a marker (e.g., G418-resistance) on the chromosome comprising the human P450 gene retains a chromosome fragment comprising the human P450 gene of the donor cell can be confirmed by various means. Examples include chromosome analysis, such as fluorescence in situ hybridization (FISH) using genomic DNA extracted from a selected recipient cell, a human-specific repeat sequence as a probe (L1, Alu et al., Korenberg et al., Cell, 53: 391, 1988), and a human chromosome-specific probe (Lichter et al., Human Genetics, 80: 224, 1988), PCR using a human P450 gene sequence-specific primer, or Southern blot analysis using a human P450 gene-specific probe.

In this regard, the green fluorescent protein (GFP) gene from *Aequorea victoria* is known as a reporter gene used for introduction of genes into animal cells (e.g., Prasher, D. C. et al., Gene, 111: 229, 1992). Light emission from GFP can be detected with fluorescence without the use of a substrate. Thus, living cells can be monitored within a short period of time. The GFP gene can be used as a positive selection marker for the loxP recombinant. Specifically, the GFP gene containing no promoter is inserted at one end of the SC20-HAC vector, and a promoter that is necessary for GFP expression is inserted at the centromer side end of the CYP3A gene cluster on chromosome 7. Upon Cre-induced recombination between loxP sequences, a promoter is ligated to the GFP gene, and GFP is then expressed. This recombinant DT40 cell emits fluorescence, which enables selection for cloning of the CYP3A gene cluster into the SC20-HAC vector and selection of the HAC vector in a recipient cell.

(iv) Construction of Chimeric Animal from ES or Pluripotent Cell Derived from Non-Human Mammalian Animal into which Artificial Chromosome Containing Human P450 Gene (CYP3A Gene Cluster) Had been Introduced The present invention further provides a non-human mammalian animal that retains the above-described human artificial chromosome vector and enables expression of the human cytochrome P450 gene.

A chimeric animal can be produced from an ES or pluripotent cell derived from a non-human mammalian animal, such as a mouse ES cell or ntES cell, by the method described in, for example, Bio-Manual Series 8, Gene targeting, Shinichi Aizawa, Yodosha (Japan), 1995. The developmental stage, the strain, and other host embryo conditions used for efficient production of a chimeric animal are preferably selected in accordance with the established ES cell conditions. Regarding TT2 cells (wild-type color, Yagi et al., Analytical Biochemistry, 214: 70, 1993) derived from the mouse ES cell line (CBA×C57BL/6 F1), for example, it is preferable that a 8-cell stage embryo derived from Balb/c (white, CLEA Japan, Inc.) or ICR (CLEA Japan, Inc.) be used as a host embryo.

Specifically, microcells are purified from CHO cells retaining the artificial chromosome vector of the present invention constructed in the manner described above, and the microcell is fused with an ES or ntES cell in the presence of polyethylene glycol (e.g., PEG 1000) in DMEM medium. The resulting ES or ntES cell clone was injected into an 8-cell-stage embryo (described above) obtained via sexual crossing, and the injected embryo was transplanted into a foster mother to produce chimeric animals. A preferable pluripotent cell is an ES or ntES cell derived from a non-human mammalian animal. A more preferable ES or ntES cell is a mouse ES cell or a mouse ntES cell.

According to a preferable embodiment, the endogenous CYP3A gene of a non-human mammalian animal can be disrupted in order to efficiently express the human P450 gene and to make drug metabolism by the CYP3A gene on human chromosome 7 more similar to that of a human. Specifically, an animal into which the human gene had been introduced may be subjected to disruption of the endogenous CYP3A gene. Alternatively, a human gene can be introduced into an animal in which the endogenous CYP3A gene had been disrupted.

In the present invention, the thus-obtained non-human mammalian animal is a chimeric animal retaining the artificial chromosome vector of the present invention and enabling expression of the human P450 gene or progeny thereof. Also, a progeny animal may be obtained by crossing the above chimeric animal with the wild-type, or it may be obtained by crossing the above chimeric animal with an allogeneic animal in which a relevant gene had been disrupted.

According to a preferable embodiment, the cytochrome P450 gene inherent to or native for a non-human mammalian animal, which is a homolog of the human CYP3A gene cluster, is previously disrupted, after which the expression level of the native gene is lowered or expression ceases in the non-human mammalian animal of the present invention.

According to a more preferable embodiment, the non-human mammalian animal of the present invention is a mouse, and a chimeric mouse and a progeny mouse thereof are within the scope of the present invention. Such mouse or progeny thereof retains the artificial chromosome vector of the present invention, it lacks the mouse Cyp3a gene cluster, and it enables expression of the human cytochrome P450 gene.

According to the present invention, chimeric non-human mammalian animals are constructed from ES cells (heterozygously lacking the Cyp3a gene cluster), and the resulting chimeric animals are subjected to crossing with wild-type animals to obtain F1 animals that heterozygously lack the Cyp3a gene cluster. The resulting F1 animals are subjected to crossing to obtain F2 animals that homozygously lack the Cyp3a gene cluster. Separately, a chimeric non-human animal retaining a human artificial chromosome comprising the human CYP3A gene cluster is subjected to crossing with a wild-type animal to obtain an F1 animal retaining such human artificial chromosome. The resulting F1 animal is subjected to crossing with the above F2 animal that homozygously lacks the Cyp3a gene cluster to obtain an F2 animal that heterozygously lacks the Cyp3a gene cluster and retains such human artificial chromosome. By subjecting this F2 animal to crossing with an F2 animal that heterozygously lacks the Cyp3a gene cluster, a target non-human mammalian animal (i.e., a non-human mammalian animal that homozygously lacks the mouse Cyp3a gene cluster and retains the human artificial chromosome) can be obtained at the end.

(v) Confirmation of Whether a Chimeric Non-Human Mammalian Animal or a Progeny Thereof Retains an Artificial Chromosome Comprising the Human P450 Gene (the CYP3A Gene Cluster) and Human Gene Expression Therein The contribution ratio of an ES cell to a non-human mammalian animal generated from an embryo into which such ES cell has been introduced can be roughly determined based on hair color. Even if no contribution of an ES cell is observed based on hair color, however, it cannot be determined that an ES cell did not contribute to other tissue. Retention of a human chromosome in each tissue of a chimeric animal can be more precisely confirmed by means of Southern blot analysis, PCR, FISH, or other means using genomic DNA extracted from the relevant tissue. Expression of the human P450 gene on the introduced chromosome can be confirmed in the following manner. Expression of mRNA derived from a chromosome comprising the human P450 gene is detected by RT-PCR (Kawasaki et al., Proc. Natl. Acad. Sci. U.S.A., 85: 5698, 1988) or Northern blot analysis (Ausubel et al., Current Protocols in Molecular Biology, Johen Willy & Sons, 1994) using RNA derived from relevant tissue. Levels of protein expression are detected by Western blot analysis (Ausubel et al, ibid), assy of testosterone 6β hydroxylation activity using hepatic microsomes of a chimeric animal, or other means. Further, retention of a chromosome comprising the human P450 genes and gene expression on such chromosome in chimeric animal cells can be confirmed based on appearance of resistant genes via expression of marker genes for drug resistance or reporter genes in primary cultured cells derived from a chimeric animal.

When ES cells that retain the artificial chromosome comprising the human P450 genes are differentiated into germ cells of the chimeric animal of the non-human mammalian animal of the present invention, introduction of chromosome fragments comprising the human P450 genes is observed in progeny thereof, and genes on such chromosome fragments are expressed.

Further, whether or not the human chromosome comprising human P450 gene(s) was transmitted to progeny by crossing the chimeric animal with a normal animal can also be confirmed by means of Southern blot analysis, PCR, FISH, or other means using genomic DNA extracted from the tissue, organ, or cells of the progeny animal. Also, stage-specific or tissue-specific gene expression, such as at the ontogenetic stage of progeny animals, can be confirmed in the above-described manner.

(vi) Confirmation of Induction of Gene Expression in Progeny-Transmitted Non-Human Mammalian Animal Gene expression is confirmed in the manner employed in (v) above. For example, induction of gene expression is induced with rifampicin or PCN (see Example 6).

(vii) Production of Knockout Animal Lacking Endogenous P450 Genes of Non-Human Mammalian Animal Knockout vectors and knockout ES cells can be produced by the method described in, for example, Example 7 below, P. Hasty et al., Nature, 1991, 350: 243-246, or M. Zijlstra et al., Nature, 1989, 342: 435-438, and knockout animals can be produced in the same manner as in (iv) above.

Briefly, an example of a method that is usually employed for inactivating functions of a target endogenous gene is the gene targeting method. For example, a foreign gene, such as the $neo^r$ gene, is inserted into an exon of genomic DNA having a size of approximately several kb containing a plurality of exons of the gene to prepare recombinant DNA, the resulting recombinant DNA is inserted into an adequate vector, and a knockout vector can then be constructed. Vector DNA is introduced into an ES cell, G418-resistant cells are selected, cells that have undergone homologous recombination are selected via, for example, Southern blot analysis, the selected cells are injected into blastocysts, and the resulting embryos are transplanted into a uterus of a foster parent non-human mammalian animal of the same species to produce chimeric animals. A homozygous knockout animal can be obtained via crossing between chimeric animals or between a chimeric animal and a wild-type animal.

Cyp3a gene cluster comprising the endogenous (or "inherent") P450 gene of a mouse includes the P450 genes, such as Cyp3a11, Cyp3a13, Cyp3a25, and Cyp3a41, and such cluster is present on mouse chromosome 5 (e.g., Cyp3a11 is present on Chr5.78.0cM, and Cyp3a13 is present on Chr5.73.7cM).

(viii) Confirmation of Endogenous P450 Gene Defect in Knockout Non-Human Mammalian Animal The contribution rate of ES cells to the constructed knockout animals can be roughly determined based on hair color, as in the case of chimeric animals into which the human chromosome had been introduced. Further, it is preferable that endogenous gene defects be confirmed by Southern blot analysis, PCR, or other means using genomic DNA extracted from knockout animals. When GFP is inserted into a targeting site, expression is observed in individual animals. Thus, knockout animals can be easily selected with the use of fluorescence, as in the case of selection in ES cells.

(ix) Production of Non-Human Mammalian Animal in which Endogenous P450 Genes Had been Deleted and into which Human P450 Genes Had been Introduced Human P450-retaining animals that retain the human chromosome comprising the human P450 genes and lack the endogenous P450 genes of a non-human mammalian animal are obtained by subjecting a chimeric animal retaining the human chromosome comprising the human P450 genes constructed by the method described above or progeny thereof to crossing with a chimeric animal that lacks the entire endogenous P450 gene cluster or progeny thereof. The properties of animals "retaining the human chromosome" and "lacking the endogenous P450 gene" are considered to basically result from transmission of such genetic factors in accordance with the Mendel's law.

Animals can be crossed in various ways. Specifically, the crossing between animals can be performed in the following manner. At the outset, chimeric animals that heterozygously lack the Cyp3a gene cluster are subjected to crossing with wild-type animals to obtain F1 animals that heterozygously lack the Cyp3a gene cluster (F1 animals A). F1 animals A are subjected to crossing with each other to obtain F2 animals that homozygously lack the Cyp3a genes (F2 animals B). Separately, chimeric animals that retain the human artificial chromosome comprising the human CYP3A gene cluster are subjected to crossing with wild-type animals to obtain F1 animals that retain such human artificial chromosome (F1 animals C). F2 animals B are subjected to crossing with F1 animals C to obtain F2 animals that heterozygously lack the Cyp3a gene cluster and retain the human artificial chromosome (F2 animals D). The resulting F2 animals D are subjected to crossing with F2 animals B, and the animals of interest (which homozygously lack the Cyp3a gene cluster and retain the human artificial chromosome) can be obtained.

According to the present invention, a pluripotent cell derived from a non-human mammalian animal retaining the aforementioned human artificial chromosome vector can be further prepared from a non-human mammalian animal in which the endogenous P450 genes have been deleted and into which the human P450 gene(s) has been introduced. In such pluripotent cell derived from a non-human mammalian animal, a homolog of the human CYP3A gene cluster; i.e., the cytochrome P450 gene inherent to the non-human mammalian animal, has been disrupted, and the expression level thereof is reduced or the expression is lost. Examples of pluripotent cells include embryonic carcinoma cells (EC cells, Hanaoka et al., Differentiation, 48: 83, 1991), embryonic stem cells (ES cells, Evans et al., Nature, 292: 154, 1981), embryonic germ cells (EG cells, Matsui et al., Cell, 70: 841, 1992), and induced pluripotent stem cells (iPS cells, Takahashi et al., Cell, 126: 663, 2006), as described above. Specific examples include nuclear transplantation-derived embryonic stem cells (ntES cells, Wakayama et al., Science, 292: 740, 2001), such as mouse-derived ntES cells. Examples 13 to 16 below more specifically describe such cells.

(x) Method for Preparing Human P450 Protein

The present invention further provides cells that are derived from a non-human mammalian animal, a mouse, or progeny thereof and that can express the human cytochrome P450 gene or organs or tissue comprising such cells.

The present invention also provides a method for preparing biologically active human cytochrome P450 comprising expressing the human cytochrome P450 gene in a non-human mammalian animal, a mouse, or progeny thereof, or cells, organs, or tissues to produce biologically active human cytochrome P450, and recovering the human cytochrome P450.

The nucleotide sequences and the amino acid sequences of human P450 are registered under GenBank Accession Nos. NM_017460 (the CYP3A4 gene), NM_000777 (the CYP3A5 gene), NM_000765 (the CYP3A7 gene), and NM_0022820 (the CYP3A43 gene), for example.

Biologically active human P450 proteins can be obtained from the organs, tissues, or cells of the chimeric animals obtained in the above-described manner. For example, fractions containing human P450 are extracted and purified from hepatic microsomes of chimeric animals or progeny thereof, and human P450 proteins can be thus extracted. Alternatively, cell lines are established from tissue of chimeric animals retaining chromosomes containing the human P450 gene or progeny thereof, the established cell lines are cultured, and human P450 proteins can be recovered from the culture products.

Protein purification can be carried out via a combination of known techniques. Examples of purification techniques include chromatography techniques, such as gel filtration chromatography, ion-exchange chromatography, affinity chromatography, HPLC, and FPLC, electrophoresis, isoelectric point electrophoresis, ultrafiltration, ammonium sulfate fractionation, and dialysis.

Human P450 can be identified using commercially available assay kits. Examples of assay kits include P450-Glo™ CYP3A4 Assay (Promega) and P450-Glo™ CYP3A7 Assay (Promega). The assay technique involves conversion of a luciferin derivate, which is a P450 substrate, into luciferin with the aid of P450 enzyme and assaying P450 enzyme activity based on the emission level generated via luciferase reaction.

(xi) Method for Testing Pharmacological Effects and/or Metabolism of Drugs or Food Products The present invention further provides a method for testing pharmacological effects and/or metabolism of drugs or food products comprising administering drugs or food products to a non-human mammalian animal, a mouse, or progeny thereof, or cells, organs, or tissues and assaying pharmacological effects and/or metabolism of the drug or food products The chimeric animal of the present invention or a progeny thereof or animals into which human P450 has been introduced resulting from crossing of such chimeric animals with knockout animals lacking endogenous P450 genes are considered to express human P450 in the same manner as in cases in which human P450 is expressed in human bodies. By administering a given drug, accordingly, such animals become useful as experimental animals used for researching pharmacological effects, toxicity, carcinogenicity, teratogenicity, or pharmacodynamics, at the individual level. Further, a mechanism of drug metabolism in humans or drug toxicity in tissue can be studied without administration of drugs to humans. By performing metabolic analysis using animals, metabolic activity of drugs that can be metabolized by human CYP3A can be detected via, for example, assay of triazolam hydroxylation activity or assay of testosterone 6β hydroxylation activity using hepatic microsomes. Specific examples of such test methods are described in Example 12, FIG. 22, and FIG. 23.

(xii) Percentages of Chimerism and Retention

In the present invention, a region of approximately 3 Mb and a region of approximately 1 Mb comprising the CYP3A gene cluster region on human chromosome 7 were translocated and cloned into the SC20-HAC vector to obtain human artificial chromosomes (i.e., CYP3A-HAC and CYP3A-HACΔ) as described above. CYP3A-HAC and CYP3A-HAC4 were introduced into mouse individuals, the percentage of chimerism in a chimeric mouse was compared with that of #7-HAC (Kuroiwa et al., Gene Ther., 9: 708, 2002), and improvement in the percentages of chimerism and chromosome retention and efficient transmission of the human artificial chromosomes to progeny were examined.

The percentage of chimerism represents the contribution rate of ES cells to tissue (body hair) of a chimeric animal, and it is generally determined by visually evaluating the proportion of the color of body hair derived from ES cells on the body surface of the chimeric animal. The percentage of retention indicates the rate of contribution of the introduced chromosome to tissue. When a factor that is stable as a human chromosome and that adversely affects development is present on the chromosome, a mouse exhibiting a high percentage of chimerism undergoes developmental disorders and dies (i.e., such chimeric mouse would not be born). Even if a factor that adversely affects development is present on the chromosome, however, a chimeric mouse exhibiting a high percentage of chimerism may be born if such factor is unstable. In such a case, the human chromosome would not be retained at high frequency.

The "stable" condition described herein could be affected by functions of the centromere of each chromosome or a gene(s) on each chromosome (e.g., a factor that suppresses cell growth).

In order to obtain a stably transmissible individual, accordingly, it is necessary for a chimeric mouse with a high percentage of chimerism (i.e., a chimeric mouse individual exhibiting a high rate of contribution of ES cells to somatic cells) to retain foreign chromosomes at a high percentage of retention.

Chimeric mice retaining a human chromosome 7 fragment or #7-HAC with a high percentage of chimerism have been prepared in the past, although such chimeric mice did not stably transmit a human chromosome 7 fragment or #7-HAC to progeny (WO 01/011951; Kuroiwa et al., Gene Ther., 9: 708, 2002). The fact that foreign chromosomes were not transmitted to progeny in chimeric mice retaining a human chromosome 7 fragment or #7-HAC with a high percentage of chimerism indicates that condition contribution ratio of the introduced chromosomes to tissue was low.

According to the present invention, a transchromosomic, non-human animal (e.g., a mammalian animal such as a mouse) that retains the CYP3A gene cluster can be efficiently constructed with the aid of CYP3A-HAC or CYP3A-HACΔ. Such non-human animal is considered to be useful for toxicity screening of a candidate drug for a pharmaceutical product or testing for functions or safety of food products. Since CYP3A-HAC or CYP3A-HACΔ transchromosomic mice can transmit heterogeneous chromosome fragments to progeny, crossing would enable mass-production of transchromosomic mice having homogeneous traits. According to the report by Yu et al. (Endocology 146: 2911-2919), transgenic mice into which a bacterial artificial chromosome (BAC) comprising a part (CYP3A4) of the human CYP3A gene cluster had been introduced were constructed. However, the CYP3A4 gene expressed in such mouse strain is a gene that is expressed at the adult stage, and it does not include CYP3A7 expressed at the embryo stage or other CYP3A gene clusters, such as CYP3A5 or CYP3A43. Thus, the CYP3A expressed in such mouse strain is deduced to be limited to CYP3A4. Also, the copy number of the introduced BAC or the site of introduction thereof has not yet been identified, and it is unlikely that expression is physiologically controlled in the same manner as in humans. According to the report by Herwaarden et al. (Herwaarden et al., J. Clin. Invest., 117: 3583-3592, 2007), Cyp3a knockout mice were created, and mice in which the human CYP3A4 gene was expressed in the liver or small intestine were created. In such mice, however, the human CYP3A4 gene was ligated to a site downstream of a liver- or small-intestine-specific promoter and forced to express. Thus, it is unlikely that expression is physiologically controlled in the same manner as in humans.

In the mouse strain that expresses the human CYP3A gene cluster of the present invention, stage-specific expression, tissue-specific expression, the capacity for expression induction, and other conditions of the CYP3A gene cluster are accurately reproduced as in the case of humans. Since such mice comprise CYP3A4 or CYP3A7, for example, CYP3A expression at the adult and embryo stages can be detected as in the case of humans. Examples of inducers include rifampicin and pregnenolone 16α-carbonitrile (PCN).

By inducing expression of transchromosomic mice that express the human CYP3A gene cluster with the use of an adequate inducer, highly active microsome S9 can be obtained from the liver thereof. S9 can be used for research on the metabolism of drugs, chemical products, or food products.

With the use of the transchromosomic, non-human animal cells or animals obtained in the above-described manner, further, genes on the foreign chromosomes or fragments thereof are expressed, and expression products are recovered. Thus, biologically active substances can be produced. Specifically, transchromosomic, non-human animals are grown under conditions in which genes on the foreign chromosomes or fragments thereof can then be expressed, and expression products can be recovered from the livers, small intestines, or other organs of the animals.

Also, tissue, cells, or immortalized tissue or cells (e.g., liver-derived stem cells) of transchromosomic, non-human animals are cultured under conditions in which genes on the foreign chromosomes or fragments thereof can be expressed, and expression products can then be recovered from the culture products.

Alternatively, a foreign chromosome extracted from the tissue, cells, or immortalized tissue or cells of transchromosomic, non-human animals or a fragment thereof, DNA constituting such foreign chromosome or a fragment thereof, or cDNA derived from a foreign chromosome retained by the tissue, cells, or immortalized tissue or cells of transchromosomic, non-human animals or a fragment thereof is introduced into an animal cell, yeast cell, or insect cell (e.g., CHO cells, BHK cells, hepatic cancer cells, myeloma cells, bread yeast cells, SF9 cells, or HEPG2 cells). Such cells are cultured under conditions in which genes on the foreign chromosomes or fragments thereof can be expressed, and expression products can then be recovered from the culture products. Examples of biologically active substances include any substances encoded on foreign chromosomes. Specific examples include P450, such as human CYP3A4, CYP3A5, CYP3A7, and CYP3A43.

Hereafter, the present invention is described in detail with reference to the examples, although the technical scope of the present invention is not limited thereto.

EXAMPLES

In Example 1 to Example 16 below, construction of human artificial chromosome CYP3A-HAC or CYP3A-HACΔ via translocation and cloning of a 3 Mb or 1 Mb region in the vicinity of the human CYP3A gene cluster on human chromosome 7 into the SC20-HAC vector is described (FIG. 1). Further, introduction of the constructed HAC chromosomes into mouse individuals and transmission thereof to chimeric mouse progeny are described.

Example 1

Construction of Human Artificial Chromosome CYP3A-HAC Via Translocation and Cloning of 3 Mb Region in the Vicinity of Human CYP3A Gene Cluster (AC004922-Human CYP3A Gene Cluster-AF006752) into SC20-HAC Vector (A) Site-Specific Insertion of loxP Sequence into AC004922 on Human Chromosome 7

(A.1) Construction of Targeting Vector, pNPloxPHyg

A targeting vector (pNPloxPHyg) was prepared in the following manner, which was used for inserting a Cre recombinase recognition sequence (loxP) into the AC004922 region, which is located in the extreme vicinity of the CYP3A gene locus on human chromosome 7 and at a site of approximately 300 Kb from the CYP3A gene locus toward the centromere At the outset, the AC004922 genomic region was amplified by PCR using the following primers.

```
p450loxP7L:
5'-ggcctagagcctggactcattcattcaa-3' (SEQ ID NO: 1)

p450loxP7R:
5'-gacagatgtcatgccccaggtaggtatg-3' (SEQ ID NO: 2)
```

V901 (Lexicon genetics) was used as a fundamental plasmid for inserting a loxP sequence. PCR was carried out using the GeneAmp 9600 Thermal Cycler (Perkin-Elmer), LA Taq polymerase (Takara Shuzo Co., Ltd.), and buffer or dNTPs (dATP, dCTP, dGTP, and dTTP) included in the kit in accordance with the recommended conditions. A cycle of thermal denaturation at 94° C. for 1 minute, followed by 98° C. for 20 seconds and 68° C. for 7 minutes was repeated 35 times. The PCT product was treated with Proteinase K (Gibco) and then subjected to gel filtration with the use of CHROMA SPIN-TE 400 (Clontech). Thereafter, the product was cleaved with restriction enzymes; i.e., BamHI (Boehringer), EcoRI (Nippon Gene Co., Ltd.), and BglII (Nippon Gene Co., Ltd.), followed by gel filtration with CHROMASPIN-TE1000 (Clontech). The PCR fragments (3.7 kb and 3.0 kb) were cloned into the EcoRI and BamHIH or BglII sites of the V901 plasmid (V901-NP21). Subsequently, V901-NP21 was cleaved with the AscI restriction enzyme (NEB) and dephosphorylated. Thereafter, DNA fragments containing loxP were cleaved from the cassette vector, ploxPhyg (Kuroiwa et al., Nature Biotech. 18: 1086, 2000), with the aid of the AscI restriction enzyme, followed by ligation. The fragment in which the direction of the loxP sequence was the same as that of the cloned AC004922 genomic fragment was designated as the targeting vector, pNPloxPHyg. The size of the final loxP-inserted construct was 14.1 kb. FIG. 4*a* shows the targeting vector, the target sequence, and the chromosome allele resulting from homologous recombination.

(A.2) Transfection and Isolation of Hygromycin-Resistant Clone

The targeting vector, pNPloxPHyg, constructed in (A.1) above was transfected into the chicken DT-40 cell (clone DF141) retaining a human chromosome 7 fragment (cleaved at the AF006752 locus in site-specific manner), which was prepared by the method disclosed in WO 01/011951, to insert a loxP sequence into the AC004922 genomic region.

Chicken DT-40 cells were cultured in RPMI 1640 medium (Gibco) comprising 10% fetal bovine serum (Gibco, hereafter abbreviated as "FBS"), 1% avian blood serum (Gibco), and $10^{-4}$M 2-mercaptoethanol (Sigma). Cells (about $10^7$ cells) were washed once in nonsupplemented RPMI 1640 medium, the washed cells were suspended in 0.5 ml of nonsupplemented RPMI 1640 medium, 25 to 30 μg of the targeting vector, pNPloxPHyg, linearized with the NotII restriction enzyme (Takara Shuzo Co., Ltd.) was added thereto, the resultant was transferred into a cuvette for electroporation (Bio-Rad), and the cuvette was allowed to stand at room temperature for 10 minutes. The cuvette was mounted on the Gene Pulser (Bio-Rad), which was set at a voltage of 550 V and a capacitance of 25 μF. After the cuvette was allowed to stand at room temperature for 10 minutes, culture was conducted for 24 hours. Thereafter, the medium was exchanged with a medium containing hygromycin B (1.5 mg/ml), the culture product was fractionated into three 96-well culture plates, and selective culture was conducted for about 2 weeks. A total of 96 resistant colonies resulting from 5 transfection operations were isolated, grown, and then subjected to analyses described below (clone name: DT40 (NP)).

(A.3) Selection of Homologous Recombinant (A.3.1) PCR Analysis

Genomic DNA was extracted from hygromycin B-resistant clones using the Puregene DNA Isolation Kit (Gentra System), and homologous recombinants were identified via PCR using the two pair of primers shown below.

Homologous recombinants were identified via PCR using the two pair of primers shown below.

```
p450loxP14L:
5'-agttcttttgagggcctagagcctggac-3' (SEQ ID NO: 3)

p450loxP14R:
5'-aaaggacagaaggagggagcaacaggat-3' (SEQ ID NO: 4)

p450loxP16L:
5'-tctgggcatcagtgtcctctccagtaaa-3' (SEQ ID NO: 5)

p450loxP16R:
5'-ttggcgacatccaatgctagtgctattc-3' (SEQ ID NO: 6)
```

PCR was carried out using the GeneAmp 9600 Thermal Cycler (Perkin-Elmer), LA Taq polymerase (Takara Shuzo Co., Ltd.), and buffer or dNTPs (dATP, dCTP, dGTP, and dTTP) included in the kit in accordance with the recommended conditions. A cycle of thermal denaturation at 94° C. for 1 minute, followed by 98° C. for 10 seconds and 68° C. for 4 minutes was repeated 35 times. As a result of screening of 96 clones, 36 clones were identified as homologous recombinants (recombination frequency: 37.5%).

(A.3.2) Southern Blot Analysis

Figure 4:
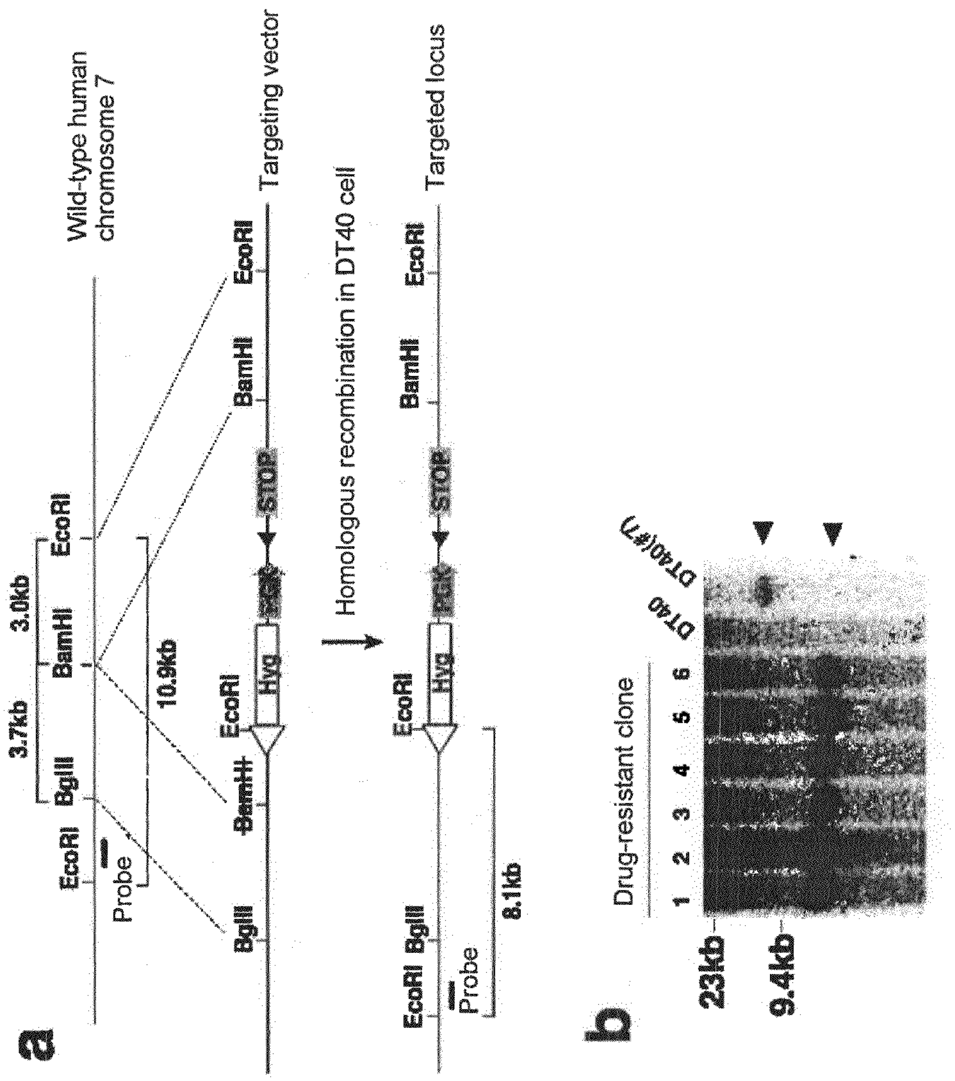
FIG. 4(*a*) schematically shows introduction of loxP into AC004922 on human chromosome 7, and FIG. 4(*b*) shows the results of Southern blot analysis demonstrating the results of introduction.

The 6 clones that were confirmed to have undergone recombination via PCR were subjected to Southern blot analysis in the following manner. The genomic DNA was treated with the EcoRI restriction enzyme (Takara Shuzo Co., Ltd.), electrophoresed on 0.8% agarose gel, and alkali-blotted on the GeneScreen Plus™ hybridization transfer membrane (NEN™ Life Science Products, Inc.). The filter was subjected to Southern hybridization using the NPp promoter obtained via amplification of the gene sequence in AC004922 via PCR, and homologous recombinants were identified (FIG. 4). The NPp probe was prepared via PCR using the primers shown below and genomic DNA of DF141 as a template, and random priming was carried out using the PCR product as a template to prepare the $^{32}$P-labeled DNA probe (Amersham, in accordance with the attached protocol).

Primers for preparing NPp probe:

```
NPp6L:
5'-tggagacgttgtttagcctctcctcctc-3' (SEQ ID NO: 7)

NPp6R:
5'-cacagcttagaggccattcccatagtcc-3' (SEQ ID NO: 8)
```

PCR was carried out using the GeneAmp 9600 Thermal Cycler (Perkin-Elmer), EX Tag polymerase (Takara Shuzo Co., Ltd.), and buffer or dNTPs (dATP, dCTP, dGTP, and dTTP) included in the kit in accordance with the recommended conditions. A cycle of thermal denaturation at 93° C. for 5 minutes, followed by 93° C. for 1 minute, 54° C. for 1 minute, and 72° C. for 1 minute was repeated 35 times. It was deduced that a band of approximately 10.9 kb would be detected in non-homologous recombinants and that of approximately 8.1 kb would be detected in homologous recombinants via Southern hybridization (FIG. 4*b*). As a result of Southern hybridization, all of the 6 clones were found to be target homologous recombinants (these clones are referred to as "NP clones").

(A.3.3) Fluorescent In Situ Hybridization (FISH) Analysis

Figure 3:
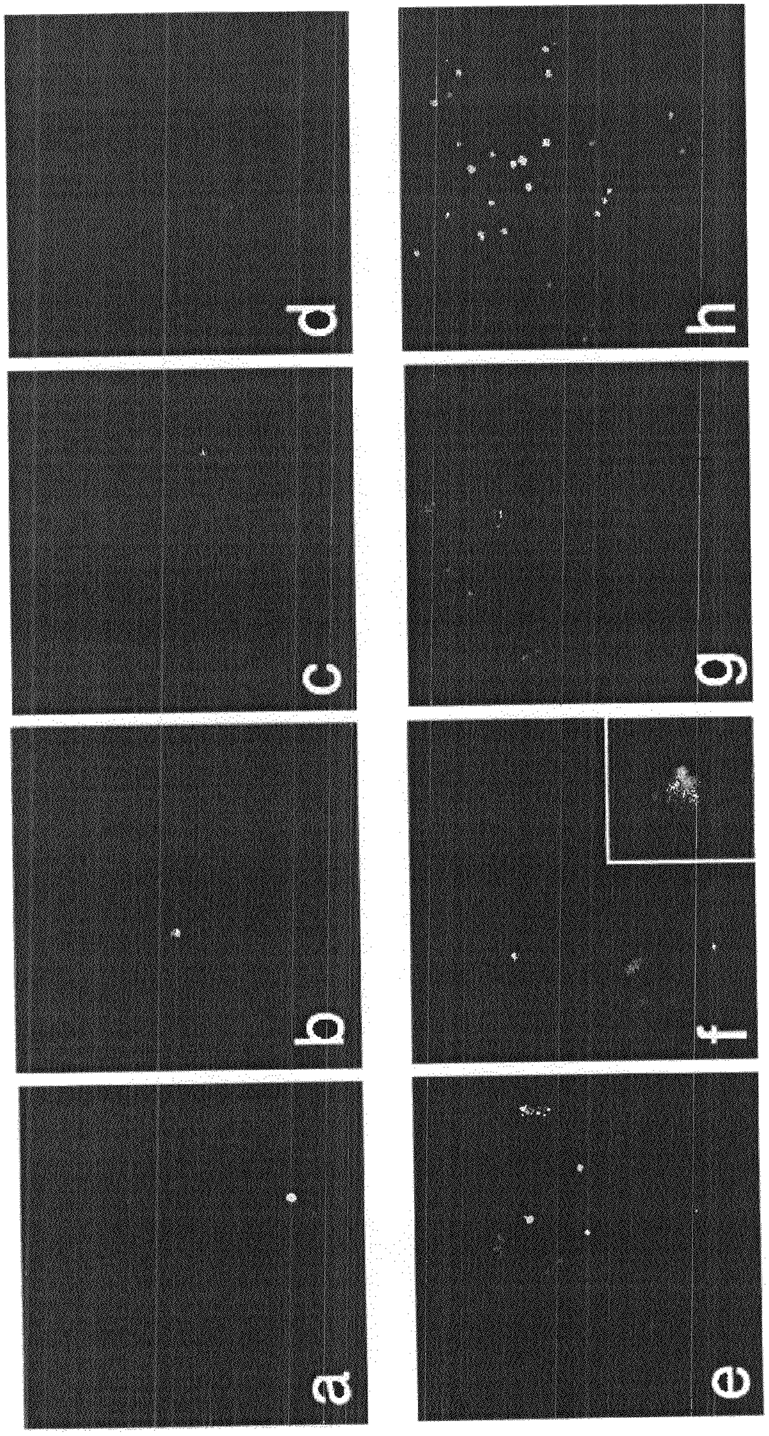
FIG. 3 is a photograph showing the results of FISH analysis demonstrating that recombination, cell fusion, and chromosome introduction have been carried out in each step.

FISH analysis was carried out in accordance with the procedure of Matsubara et al. (FISH Jikken (Experiment) Protocol, Shujunsha (Japan), 1994). Among the clones that were confirmed to have undergone recombination in A.3.2 above, 6 clones were subjected to FISH analysis using human cot-1 DNA and hygromycin as the probe. As a result, hygromycin-derived signals were detected at around 7q22 without translocation of human chromosome 7 into the chromosome of the host in all clones. Thus, it was confirmed that recombination took place in a site-directed manner. The results are shown in FIG. 3*a* to FIG. 3*c*. FIG. 3*a* shows DT40 (#7), FIG. 3*b* shows DT40 (DF141), and FIG. 3*c* shows DT40 (NP25) clones.

(B) Construction of DT-40 Hybrid Retaining Human Chromosome 7 Fragment and SC20-HAC Vector At the outset, NP25 clones obtained in A.3.2 above were subjected to cell fusion with R clones of the DT-40 cells retaining the SC20-HAC vector (Kuroiwa et al., Nature Biotech. 18: 1086, 2000) to construct a DT-40 hybrid retaining a human chromosome 7 fragment and a fragment of human chromosome 14 (SC20).

(B.1) Cell Fusion and Isolation of Double Drug Resistant Clones

R clones were cultured in RPMI 1640 medium containing blasticidin S (10 μg/ml), and NP25 clones were cultured in RPMI 1640 medium containing hygromycin B (1.5 mg/ml). The R clones (1 to 2×10$^7$ clones) were mixed with the same amount of the NP25 clones, the mixture was centrifuged, and the resultant was washed twice with serum-free RPMI 1640 medium. After the remaining medium was completely removed, 0.5 ml of 50% PEG1500 (Boehringer), which had been heated at 37° C. in advance, was added gently, and the mixture was vigorously agitated to mix with the use of a pipette for about 2 minutes. Thereafter, 1 ml of serum-free RPMI 1640 medium was slowly added over the period of 1 minute, 9 ml of serum-free RPMI 1640 medium was then added over the period of 3 minutes, and the mixture was allowed to stand at 37° C. for 10 minutes. Thereafter, the resultant was centrifuged at 1,200 rpm for 5 minutes and cultured in RPMI 1640 medium containing serum for 24 to 48 hours. Thereafter, the medium was exchanged with a RPMI 1640 medium containing blasticidin S (10 μg/ml) and hygromycin B (1.5 mg/ml), the resultant was fractionated into five 24-well culture plates, and culture was conducted for 3 to 4 weeks. A total of 8 resistant colonies obtained via 5 cell fusion operations were isolated, grown, and then subjected to the analyses described below (clone name: DT40 (RP)).

(B.2) Selection of Homologous Recombinant (B.2.1) PCR Analysis

Genomic DNA was extracted from double drug resistant clones, and PCR was carried out using the following primers to confirm that the genomic DNA retains a fragment of human chromosome 14 (SC20-HAC vector) and a human chromosome 7 fragment. Primers for detecting human chromosome 14 (SC20 chromosome vector):

```
AL157858-F:
5'CCTTCATTACGTCCTTTCGC3'          (SEQ ID NO: 9)

AL157858-R:
5'AGTCATCACTGCATCCTGGG3'          (SEQ ID NO: 10)

AL121612-F:
5'TAGGTCCTTTAGGCCATGGG3'          (SEQ ID NO: 11)

AL121612-R:
5'GCATTTTGGCCTCAAGTAGC3'          (SEQ ID NO: 12)

AL137299-F:
5'TGCTTGTTCATCTGTCAGTGG3'         (SEQ ID NO: 13)

AL137299-R:
5'ATCACAAGGTCAAGCGATCG3'          (SEQ ID NO: 14)

D14S577-F:
5'ATTTTGGGACTTCCTGGC3'            (SEQ ID NO: 15)

D14S577-R:
5'AATCTGTTTGCAGTCTTCACC3'         (SEQ ID NO: 16)

D14S272-F:
5'GAGTTCAAGGTTACAGTAAGTNATG3'     (SEQ ID NO: 17)

D14S272-R:
5'CTCTTGTCTCATAGTGCAAAGG3'        (SEQ ID NO: 18)

D14S293-F:
5'GAAACTCTAGCATGTAACACTCCAA3'     (SEQ ID NO: 19)

D14S293-R:
5'GAGCCACTGCACCTGG3'              (SEQ ID NO: 20)

D14S1227-F:
5'GCACTACATTAAAGATGTGCAACC3'      (SEQ ID NO: 21)

D14S1227-R:
5'ACTCTCACACCCACCCAGAC3'          (SEQ ID NO: 22)

D14S543-F:
5'ATGTGGGAAACAGACTCAG3'           (SEQ ID NO: 23)

D14S543-R:
5'ATTTGGATTATTTAGAATTCCC3'        (SEQ ID NO: 24)
```

-continued

```
IGHMC-F:
5'GCATCCTGACCGTGTCCGAA3'          (SEQ ID NO: 25)

IGHMC-R:
5'GGGTCAGTAGCAGGTGCCAG3'          (SEQ ID NO: 26)

D14S1007-F:
5'AGCTCCTATATGTCTTCACACAG3'       (SEQ ID NO: 27)

D14S1007-R:
5'CTCCATTCCCATACGTCC3'            (SEQ ID NO: 28)

D14S1419-F:
5'TAGGGACAGGCAGTTGATTA3'          (SEQ ID NO: 29)

D14S1419-R:
5'CAATTAATGTAAAAATTAGCCA3'        (SEQ ID NO: 30)

D14S1420-F:
5'TGTTTGAAGAAGGGAGTCGT3'          (SEQ ID NO: 31)

D14S1420-R:
5'CCCACTCCATGTCTTCTGTT3'          (SEQ ID NO: 32)

IGHV3-F:
5'AGTGAGATAAGCAGTGGATG3'          (SEQ ID NO: 33)

IGHV3-R:
5'CTTGTGCTACTCCCATCACT3'          (SEQ ID NO: 34)
```

Primers for detecting human chromosome 7 (CYP3A gene cluster):

```
CYP3A4F7: 5'GCAAGACTGTGAGCCAGTGA3'   (SEQ ID NO: 35)

CYP3A4R7: 5'GGCTGCATCAGCATCATCTA3'   (SEQ ID NO: 36)

CYP3A7F:  5'ACCCTGAAATGAAGACGGGC3'   (SEQ ID NO: 37)

CYP3A7R:  5'GAGTTAATGGTGCTAACTGGGG3' (SEQ ID NO: 38)

CYP3A5F:  5'ATAGAAGGGTCTGTCTGGCTGG3' (SEQ ID NO: 39)

CYP3A5R:  5'TCAGCTGTGTGCTGTTGTTTGC3' (SEQ ID NO: 40)
```

PCR was carried out using the GeneAmp 9600 Thermal Cycler (Perkin-Elmer), EX Taq polymerase (Takara Shuzo Co., Ltd.), and buffer or dNTPs (dATP, dCTP, dGTP, and dTTP) included in the kit in accordance with the recommended conditions. A cycle of thermal denaturation at 94° C. for 1 minute, followed by 98° C. for 10 seconds, 56° C. for 30 seconds, and 72° C. for 30 seconds was repeated 35 times. As a result of PCR, 6 of the 8 clones were found to be positive for all primers.

(B.2.2) Fluorescent In Situ Hybridization (FISH) Analysis

FISH analysis was carried out in accordance with the procedure of Kuroiwa et al. (Nature Biotech. 18: 1086, 2000). Among the clones that were confirmed to have undergone recombination in B.2.1, 6 clones were subjected to FISH analysis using a human chromosome 14-specific probe (rhodamine label) and a human chromosome 7-specific probe (FITC label). As a result, the SC20-HAC vector and the human chromosome 7 fragment were not translocated to the host chromosomes in all clones, and signals thereof were independently detected. Thus, occurrence of cell fusion was confirmed. FIG. 3*d* and FIG. 3*e* show the results. FIG. 3*d* shows the results of R clones, and FIG. 3*e* shows the results of RP13 clones.

These results demonstrate that such 6 hybrid clones each retain a fragment of human chromosome 14 (SC20-HAC vector) and a human chromosome 7 fragment.

(C) Site-Specific Translocation of 3-Mb Human Chromosome 7 Region (AC004922-CYP3A Gene Cluster-AF006752) to SC20-HAC Vector in DT-40 Hybrid Clone (RP13)

In accordance with the method of Kuroiwa et al. (as above, 2000), site-specific translocation between human chromosomes was carried out with the use of the Cre-loxP system.

The pBS185hisD vector (Kuroiwa et al., Nature Biotech. 18: 1086, 2000) that stably expresses the Cre recombinase linearized by the KpnI restriction enzyme (Boehringer) was transfected into the RP13 hybrid clones in the manner described above, the resultant was fractionated into a 24-well plate, and selective culture was conducted in the presence of histidinol (1 mg/ml) for about 2 weeks. Genomes were extracted from the wells, nested PCR was carried out using the two pairs of primers shown below, and whether or not translocation had taken place between the SC20-HAC vector and the human chromosome 7 fragment was examined.

```
PGK-1:  5'-ATAGCAGCTTTGCTCCTTCG-3'   (SEQ ID NO: 41)

GFP-1:  5'-TTCTCTCCTGCACATAGCCC-3'   (SEQ ID NO: 42)

PGK-2:  5'-TGTTCTCCTCTTCCTCATCTCC-3' (SEQ ID NO: 43)

GFP-2:  5'-TGAAGGTAGTGACCAGTGTTGG-3' (SEQ ID NO: 44)
```

PCR was carried out using the GeneAmp 9600 Thermal Cycler (Perkin-Elmer), EX Taq polymerase (Takara Shuzo Co., Ltd.), and buffer or dNTPs (dATP, dCTP, dGTP, and dTTP) included in the kit in accordance with the recommended conditions. The first PCR procedure was composed of 35 repetitions of a cycle of thermal denaturation at 94° C. for 1 minute, followed by 98° C. for 10 seconds, 61° C. for 30 seconds, and 72° C. for 1 minute with the use of PGK-1 and GFP-1 primers. Part of the reaction solution was used as a template, a PCR cycle of 98° C. for 10 seconds, 59° C. for 30 seconds, and 72° C. for 0 seconds with the use of PGK-2 and GFP-2 primers was repeated 35 times. A pool of cells in the wells that were found PCR-positive and had undergone translocation was grown to $10^7$ cells, the pool was suspended in 4 ml of PBS (phosphate buffer) comprising 5% FBS and 1 μg/ml of propidium iodide (PI), and the resulting suspension was analyzed with the FACSVantage (Becton Dickinson). As reported by Kuroiwa et al. (above), the GFP gene is reconstructed and expressed upon recombination and translocation between loxP sequences. Thus, cells in which translocation has taken place can be detected via FACS. Cell fractions deduced to be GFP-positive were subjected to sorting twice. Culture following sorting was carried out in RPMI 1640 medium containing hygromycin B (1.5 mg/ml). As a result, GFP-positive cells were concentrated with purity of 98% to 99%.

Subsequently, GFP-positive clones (RPC13F2) that were analyzed via FACS were subjected to PCR using the PGK-2 and GFP-2 primers in order to confirm that recombination had taken place between loxP sequences as anticipated. Further, RPC13F2 clones were subjected to FISH analysis (Kuroiwa et al., as above) using a human chromosome 14-specific probe (rhodamine label) and a human chromosome 7-specific probe (FITC label). As a result, the presence of the artificial chromosome in which the human chromosome 7 region had translocated to the SC20-HAC vector (a fragment of human chromosome 14) was observed (FIG. 3*f*).

Thus, it was concluded that a human artificial chromosome (CYP3A-HAC) was constructed in which a 3-Mb region in the vicinity of the CYP3A gene cluster region (AC004922-CYP3A gene cluster-AF006752) had translocated and cloned into the SC20-HAC vector in the RPC13F2 clones.

(D) Introduction of CYP3A-HAC into CHO Cell of DT-40 Hybrid Cell Containing CYP3A-HAC As reported by Kuroiwa et al. (as above), the constructed HAC was first introduced into CHO cells in order to introduce the same into the mouse ES cells.

DT-40 hybrid clones (RPC13F2) were cultured in 8 T225 flasks (Sumilon), the medium was exchanged with a RPMI 1640 medium containing 20% FBS, 1% avian blood serum, $10^{-4}$M 2-mercaptoethanol, and 0.05 μg/ml colcemid when the culture reached confluence, and culture was carried out for an additional 24 hours to form microcells. The cells were suspended in 24 ml of serum RPMI 1640 medium, the suspension was fractionated into twelve 25 $cm^2$ centrifuge flasks (Corning), which had been coated with 100 μg/ml poly-L-lysine in advance, in amounts of 2 ml each, and culture was conducted at 37° C. for 1 hour to have the cells to adhere to the bottoms of the flasks. The culture solution was removed, the centrifuge flasks were filled with a cytochalasin B solution (10 μg/ml, Sigma), which had been heated at 37° C. in advance, and centrifugation was carried out at 34° C. and 8,000 rpm for 1 hour. Microcells were suspended in serum-free DMEM medium and purified through 8 μm-, 5 μm-, and 3 μm-filters. Thereafter, the resultant was centrifuged at 1,700 rpm for 10 minutes and suspended in 5 ml of serum-free DMEM medium. Separately, about 10' CHO cells were peeled via trypsin treatment, washed twice with serum-free DMEM medium, and suspended in 5 ml of serum-free DMEM medium. The microcells were centrifuged again at 1,700 rpm for 10 minutes, and 5 ml of the CHO suspension obtained above was gently superposed thereon without removing the supernatant. After centrifugation, the culture solution was removed, 0.5 ml of PEG 1500 solution (Boehringer) was added, and the mixture was vigorously agitated using a pipette for about 2 minutes. Thereafter, 10 ml of serum-free DMEM medium was slowly added over the period of about 3 minutes, and the resultant was allowed to stand at 37° C. for 10 minutes. After centrifugation, cells were suspended in F12 medium containing 10% FBS (Gibco), the suspension was fractionated into 5 or 6 24-well culture plates, and culture was conducted at 37° C. for 24 hours. Thereafter, the medium was exchanged with F12 medium containing G418 at 800 μg/ml and selective culture was conducted for 3 to 4 weeks.

Genomic DNA was extracted from G418-resistant clones, PCR was carried out under the conditions described above with the use of a primer for detecting the CYP3A gene cluster, a primer for detecting human chromosome 14, the PGK-2 primer, and the GFP-2 primer to identify CHO clones retaining CYP3A-HAC (e.g., CHO/CYP3A-HAC4,25). Further, the clones that were found positive via PCR were subjected to FISH analysis using human COT1 DNA as a probe, and the presence of CYP3A-HAC was visually observed. It was thus concluded that CHO cell clones retaining CYP3A-HAC were obtained (FIG. 3*g*).

(E) Transfer of CYP3A-HAC from CHO Cell to Mouse ES Cell

In order to construct a chimeric mouse retaining CYP3A-HAC, CYP3A-HAC obtained in (D) above were transferred from the CHO cells retaining the same to mouse ES cells (wild-type TT2F) by the microcell method.

In accordance with the method of Tomizuka et al. (Nature Genet. 16: 133, 1997), microcells were purified from about $10^8$ CHO cells retaining CYP3A-HAC (e.g., CHO/CYP3A-HAC4, 25, 32, or 33) and suspended in 5 ml of DMEM. Mouse ES cells (TT2F, about $10^7$ cells) were peeled via trypsin treatment, washed three times with DMEM, suspended in 5 ml of DMEM, added to the centrifuged microcells, and centrifuged at 1,250 rpm for 10 minutes to completely remove the supernatant. The precipitate was thoroughly loosened via tapping, 0.5 ml of 1:1.4 PEG solution (a solution of 5 g of PEG1000 (Wako Pure Chemical Industries, Ltd.) and 1 ml of DMSO (Sigma) in 6 ml of DMEM) was added, and the mixture was thoroughly agitated for about 1 minute and 30 seconds. Thereafter, 10 ml of DMEM was slowly added, the mixture was centrifuged at 1,250 rpm for 10 minutes, the resultant was suspended in 30 ml of ES medium, the suspension was fractionated into three petri dishes having a diameter of 100 mm (Corning) seeded with feeder cells, and culture was conducted. The medium was exchanged with a medium containing G418 at 300 μg/ml 24 hours thereafter, and selective culture was carried out for about 1 week. As a result, 25 clones resulting from CHO/CYP3A-HAC4, 13 clones resulting from CHO/CYP3A-HAC25, and 28 clones resulting from CHO/CYP3A-HAC32 were found positive via PCR using the primer for detecting the CYP3A gene cluster and the primer for detecting human chromosome 14. As a result of FISH analysis using the human COT1 DNA probe (Tomizuka et al., Nature Genet. 16: 133, 1997), the presence of CYP3A-HAC detected specifically by the COT1 probe was observed in 52 of the 66 clones. Among such clones, 28 clones exhibited normal mouse karyotypes. It was thus concluded that 28 clones of TT2F cells retaining CYP3A-HAC were obtained (FIG. 3*h*).

(F) Production of Chimeric Mouse Retaining Human Artificial Chromosome, CYP3A-HAC Chimeric mice were produced by the method of Tomizuka et al. (Nature Genet. 16: 133, 1997) using the ES cell clones obtained in (E). As the host cells, 8-cell stage embryos obtained via male and female crossing of MCH (ICR) mice (white, purchased from CLEA Japan, Inc.) were used. Whether or not progeny mice resulting from transplantation of the injected embryos into foster mothers are chimeric mice can be determined based on hair color. Wild-type TT2F/CYP3A-HAC clones (e.g., F8/CYP3A-HAC-1 and 18, obtained in (E) above) were injected into 9,410 embryos, and such embryos were transplanted into foster mothers. As a result, 484 chimeric mice were born (dark brown color was observed in hair). Among them, 29 individuals had percentages of chimerism of about 100% in which substantially no white portion was observed. Specifically, ES cell lines (TT2F) retaining the human artificial chromosome (CYP3A-HAC) have the capacity for chimera formation; i.e., the capacity for differentiating into mouse normal tissue.

(G) Retention of Artificial Chromosome in Somatic Cells of Chimeric Mouse Constructed from ES Cell Retaining Human Artificial Chromosome (CYP3A-HAC)

Genomic DNA was prepared from tails of chimeric mice (percentage of chimerism=about 80%) constructed from TT2F/CYP3A clones (F8/CYP3A-HAC-1 and 18) in (F) by the method of Tomizuka et al. (Nature Genet. 16: 133, 1997), and PCR was carried out in the same manner as described above with the use of the primer for detecting the CYP3A gene cluster and the primer for detecting human chromosome 14 to investigate CYP3A-HAC retention. As a result, the genomic DNA of interest was found to be positive for two types of primers and CYP3A-HAC retention was observed in somatic cells of the chimeric mice. As a result of FISH analysis using the liver tissue of two chimeric mice exhibiting the percentage of chimerism of about 80% by the method of Shinohara et al. (Human Molecular Genetics: 10, 1163-1175, 2001) using the human COT1 DNA probe, the presence of CYP3A-HAC was visually observed, and the percentage of CYP3A-HAC retention was 70% in both chimeric mice, which was substantially consistent with the percentage of chimerism. The percentage of chimerism indicates a contribution rate of ES cells to tissue (body hair) and the percentage of retention indicates a contribution rate of the introduced chromosome to tissue. Use of a chimeric mouse exhibiting a high percentage of chimerism and a high percentage of retention is considered to result in more efficient differentiation of ES cells retaining the introduced chromosome into germ cells and transmission of the introduced chromosome to progeny. Specifically, use of CYP3A-HAC can enhance the efficiency for transmission of a human chromosome fragment containing the CYP3A gene to mouse progeny.

The 4 female chimeric mice prepared in (F) above (percentage of chimerism=about 100%) were subjected to crossing with male MCH (ICR) mice (white, purchased from CLEA Japan, Inc.). Among the 40 progeny mice born from chimeric mice, 29 progeny mice showed dark brown color, indicating an ES-cell-derived dominant genotype. That is, ES cell lines retaining CYP3A-HAC were found to have been differentiated into functional egg cells in female chimeric mice. Tails of the 29 dark brown progeny mice were partially cut, and genomic DNA was prepared from the samples. The DNA was subjected to PCR in the manner described above with the use of the primer for detecting the CYP3A gene cluster and the primer for detecting human chromosome 14, and retention of CYP3A-HAC was examined. As a result, all DNA samples were found to be negative for two types of primers, and retention of CYP3A-HAC in progeny chimeric mice was not observed. The fact that gene transmission was not observed in chimeric individuals showing a high percentage of chimerism and a high percentage of retention indicates the presence of a human gene that adversely affect the development or germ cell differentiation on CYP3A-HAC.

Example 2

Construction of Human Artificial Chromosome (CYP3A-HACΔ) Via Translocation and Cloning of 1-Mb region in the vicinity of human CYP3A gene cluster region (AC004922-human CYP3A gene cluster-AC073842) into SC20-HAC vector An excessive region of approximately 2 Mb still remains between the CYP3A gene cluster and AF006752 in CYP3A-HAC. In order to completely remove an excessive chromosome region and selectively translocate and clone the CYP3A gene cluster region, construction of a human artificial chromosome (CYP3A-HACΔ) via translocation and cloning of an AC00492-human CYP3A gene cluster-AC073842 region of approximately 1 Mb into the SC20-HAC vector was attempted.

(A) Transfer of CYP3A-HAC into DT40

In order to efficiently modify chromosomes, CYP3A-HAC was transferred from CHO cells to DT40 cells exhibiting a high frequency of homologous recombination. In accordance with the method of Tomizuka et al. (Nature Genet., 16: 133-143, 1997), microcells were purified from about $10^8$ CHO cells retaining CYP3A-HAC(CHO/CYP3A-HAC32, Example 1) and suspended in 5 ml of DMEM. Chicken DT40 cells ($1-2\times10^7$ cells) were washed twice with DMEM, suspended in 5 ml of DMEM, added to the centrifuged microcells, and centrifuged at 1,500 rpm for 10 minutes to completely remove the supernatant. The precipitate was thoroughly loosened via tapping, 0.5 ml of 1:1.4 PEG 1500 solution (Boehringer) was added, and the mixture was thoroughly agitated for about 2 minutes. Thereafter, 10 ml of DMEM was slowly added, the mixture was centrifuged at 1,500 rpm for 10 minutes, and the resultant was cultured in RPMI 1640 medium (Gibco) containing 10% fetal bovine serum (Gibco, hereafter referred to as "FBS"), 1% avian blood serum (Gibco), and $10^{-4}$M 2-mercaptoethanol (Sigma). The medium was exchanged with a medium containing G418 at 1 mg/ml 24 hours thereafter, and selective culture was carried out for about 3 weeks. Genomic DNA was extracted from drug-resistant colonies and PCR was carried out using the primer for detecting the CYP3A gene cluster and the primer for detecting human chromosome 14.

PCR was carried out using the GeneAmp 9600 Thermal Cycler (Perkin-Elmer), EX Taq polymerase (Takara Shuzo Co., Ltd.), and buffer or dNTPs (dATP, dCTP, dGTP, and dTTP) included in the kit in accordance with the recommended conditions. A PCR cycle of thermal denaturation at 94° C. for 1 minute, followed by 98° C. for 10 seconds, 56° C. for 30 seconds, and 72° C. for 30 seconds was repeated 35 times. As a result, 2 of about 5 clones were found to be positive for the primer for detecting the CYP3A gene cluster and the primer for detecting human chromosome 14. As a result of FISH using the human COT1 DNA probe, CYP3A-HAC was found to be independently present. Thus, cloning of chicken DT40 cells retaining CYP3A-HAC (hereafter abbreviated as "DT40 (CYP3A-HAC)") was confirmed.

(B) Site-Specific Cleavage at AC073842 in Human Chromosome 7 Region on CYP3A-HAC (B.1) Construction of Targeting Vector, pTELhisD-PT The targeting vector, pTELhisD-PT, used for inserting a human telomeric sequence into the AC073842 region, which is located in the extreme vicinity of the CYP3A locus and at approximately 150 Kb on the telomere side of the CYP3A locus on human chromosome 7, was constructed in the following manner. At the outset, the AC073842 genomic region was amplified via PCR using the following primers.

```
PT1L:
5'-tgcggtgaaggtccaaggagatagattt-3' (SEQ ID NO: 45)

PT2R:
5'-tctagcagagagatggtggcaggattca-3' (SEQ ID NO: 46)
```

Figure 5:
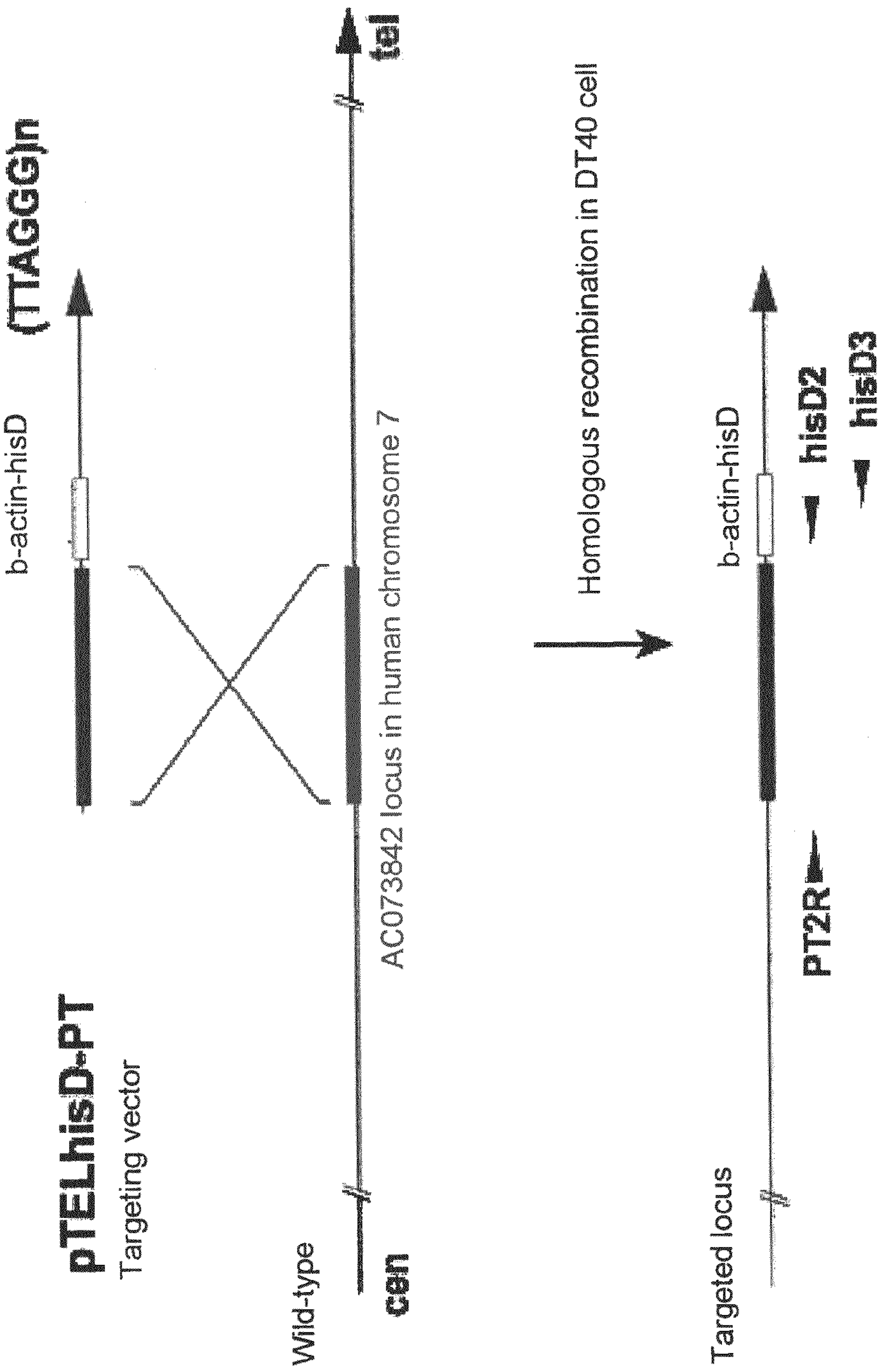
FIG. 5 schematically shows site-specific cleavage at AC073842 on human chromosome 7; "cen" indicates the centromere side and "tel" indicates the telomere side.

PCR was carried out using the GeneAmp 9600 Thermal Cycler (Perkin-Elmer), LA Taq polymerase (Takara Shuzo Co., Ltd.), and buffer or dNTPs (dATP, dCTP, dGTP, and dTTP) included in the kit in accordance with the recommended conditions. A cycle of thermal denaturation at 94° C. for 1 minute, followed by 98° C. for 20 seconds and 68° C. for 8 minutes was repeated 35 times. The PCR product was treated with Proteinase K (Gibco) and then subjected to gel filtration through CHROMA SPIN-TE 400 (Clontech). Thereafter, the resultant was cleaved with the BamHI (Boehringer) and BglII (Nippon Gene Co., Ltd.) restriction enzymes, followed by gel filtration through CHROMASPIN-TE 1000 (Clontech). The PCR fragment was cloned into the BamHI site of the pTELhisD plasmid (Kuroiwa et al., Nature Biotech., 20: 88, 2002). Since the AC073842 genomic sequence is oriented from the telomere to the centromere, the cloned AC073842 genomic fragment that was oriented in the same direction as the human telomeric sequence was designated as the targeting vector of interest, pTELhisD-PT (FIG. 5).

The size of the final construct used for proximal long arm-specific cleavage is 14.4 kb. The targeting vector, the target sequence, and the chromosome allele resulting from homologous recombination are shown in FIG. 5.

(B.2) Transfection and Isolation of Hygromycin-Resistant Clone

The targeting vector, pTELhisD-PT, constructed above was linearized with the SrfI restriction enzyme (Toyobo Co., Ltd.) in the same manner as above, the resultant was transfected into the DT40 (CYP3A-HAC)-4 clone constructed above, medium was exchanged with a medium containing histidinol (0.5 mg/ml), the resultant was fractionated into ten 96-well culture plates, and selective culture was carried out for about 2 weeks. A total of 433 resistant colonies resulting from 5 transfection operations were isolated, grown, and then analyzed as follows (clone name: DT40 (CYP3A-HACΔ)).

(B.3) Selection of Homologous Recombinant (B.3.1) PCR Analysis

In order to select recombinants using genomic DNA of a histidinol-resistant strain as a template, PCR was carried out using the primers shown below located at a site on the telomere side of the cleavage site as a primary screening, and whether or not site-specific cleavage had taken place was examined. The primer sequences are shown below.

```
AP4M1-1L: cctaacatcgtgtcccagctca   (SEQ ID NO: 47)
AP4M1-1R: tcctttcagaccccttcatcttag (SEQ ID NO: 48)
LRCH4-2L: ttcagccccaaccaaagacacta  (SEQ ID NO: 49)
LRCH4-1R: gccccgaacccctacaaatataga (SEQ ID NO: 50)
STAG3-1L: gggcctccaataagtgtcccata  (SEQ ID NO: 51)
STAG3-1R: ttgctgacttagttgcagcagga  (SEQ ID NO: 52)
PILRB-2L: cccattggcaagatacatggaga  (SEQ ID NO: 53)
PILRB-2R: agtgtggatgctcctggatgaag  (SEQ ID NO: 54)
```

PCR was carried out using the GeneAmp 9600 Thermal Cycler (Perkin-Elmer), EX Taq polymerase (Takara Shuzo Co., Ltd.), and buffer or dNTPs (dATP, dCTP, dGTP, and dTTP) included in the kit in accordance with the recommended conditions. A cycle of thermal denaturation at 93° C. for 5 minutes, followed by 93° C. for 1 minute, 56° C. for 1 minute, and 72° C. for 1 minute was repeated 35 times. Subsequently, 11 clones among the 433 clones that were not detected with the above primers were subjected to PCR with the use of the primers shown below to examine whether or not site-specific homologous recombination had taken place. The primer positions are shown in FIG. 5. The sequences are as follows.

```
hisD2: GTAAACGCCCTCAAGGAGCAAGCATGA (SEQ ID NO: 55)
hisD3: TGTGACCAAAGATTTAGCGCAGTGCGT (SEQ ID NO: 56)
```

PCR was carried out using the above primer and the primer of B. 1 above (PT2R-hisD2 and PT2R-hisD3) in combination, LATaq (Takara Shuzo Co., Ltd.), and buffer or dNTPs (dATP, dCTP, dGTP, and dTTP) included in the kit in accordance with the recommended conditions. A cycle of thermal denaturation at 94° C. for 1 minute, followed by 98° C. for 20 seconds and 68° C. for 8 minutes was repeated 35 times. Bands of approximately 8 kb were detected selectively in 9 clones among the 11 clones, which had undergone site-specific recombination. No band was detected in the negative controls DT40 or DT40 (CYP3A-HAC).

(B.3.2) Fluorescent in Situ Hybridization (FISH) Analysis

FISH analysis was carried out in accordance with the procedure of Matsubara et al. (FISH Jikken (Experiment) Protocol, Shujunsha, 1994). Among the clones that were confirmed to have undergone recombination in B.3.1 above, 7 clones were subjected to FISH analysis using human cot-1 DNA and histidinol as the probes. As a result, histidinol-derived signals were detected at the end of CYP3A-HACΔ without translocation of CYP3A-HACΔ to the host chromosomes in all clones. Thus, it was confirmed that recombination took place in a site-specific manner.

Thus, it was concluded that the human artificial chromosome CYP3A-HACΔ was constructed via translocation and cloning of a 1 Mb region of AC004922-human CYP3A gene cluster-AC073842 in the vicinity of the CYP3A gene cluster into the SC20-HAC vector in the DT40 clone (CYP3A-HACΔ)214.

A chicken DT40 cell line, DT40 (CYP3A-HACΔ)214 retaining CYP3A-HACΔ was internationally deposited at the International Patent Organism Depositary of the National Institute of Advanced Industrial Science and Technology (Tsukuba Central 6, 1-1-1 Higashi, Tsukuba, Ibaraki, 305-8566, Japan) as of Oct. 30, 2007 under the accession number: FERM BP-10928.

(C) Introduction of CYP3A-HACΔ into CHO Cells of DT-40 Hybrid Cells Containing CYP3A-HACΔ

As reported by Kuroiwa et al. (as above), the constructed HAC was first introduced into CHO cells in order to introduce the same into the mouse ES cells.

DT-40 hybrid clones DT40 (CYP3A-HACΔ)214 were cultured in 8 T225 flasks (Sumilon), the medium was exchanged with a RPMI 1640 medium containing 20% FBS, 1% avian blood serum, $10^{-4}$M 2-mercaptoethanol, and 0.05 μg/ml colcemid when the culture reached confluence, and culture was carried out for an additional 24 hours to form microcells. The cells were suspended in 24 ml of serum RPMI 1640 medium, the suspension was fractionated into twelve 25 $cm^2$ centrifuge flasks (Corning), which had been coated with 100 μg/ml poly-L-lysine in advance, in amounts of 2 ml each, and culture was conducted at 37° C. for 1 hour to have the cells to adhere to the bottoms of the flasks. The culture solution was removed, the centrifuge flasks were filled with a cytochalasin B solution (10 μg/ml, Sigma), which had been heated at 37° C. in advance, and centrifugation was carried out at 34° C. and 8,000 rpm for 1 hour. Microcells were suspended in serum-free DMEM medium and purified through 8 μm-, 5 μm-, and 3 μm-filters. Thereafter, the resultant was centrifuged at 1,700 rpm for 10 minutes and suspended in 5 ml of serum-free DMEM medium. Separately, about $10^7$ CHO cells were peeled via trypsin treatment, washed twice with serum-free DMEM medium, and suspended in 5 ml of serum-free DMEM medium. The microcells were centrifuged again at 1,700 rpm for 10 minutes, and 5 ml of the CHO suspension obtained above was gently superposed thereon without removing the supernatant. After centrifugation, the culture solution was removed, 0.5 ml of PEG 1500 solution (Boehringer) was added, and the mixture was vigorously agitated using a pipette for about 2 minutes. Thereafter, 10 ml of serum-free DMEM medium was slowly added over the period of about 3 minutes, and the resultant was allowed to stand at 37° C. for 10 minutes. After centrifugation, cells were suspended in F12 medium containing 10% FBS (Gibco), the suspension was fractionated into 5 or 6 24-well culture plates, and culture was conducted at 37° C. for 24 hours. Thereafter, the medium was exchanged with F12 medium containing G418 at 800 μg/ml and selective culture was conducted for 3 to 4 weeks.

Genomic DNA was extracted from G418-resistant clones, PCR was carried out under the conditions described above with the use of a primer for detecting the CYP3A gene cluster, a primer for detecting human chromosome 14, the PGK-2 primer, and the GFP-2 primer to identify CHO clones retaining CYP3A-HACΔ (e.g., CHO/CYP3A-HACΔ4 and 6). Further, the clones that were found positive via PCR were subjected to FISH analysis using human COT1 DNA as a probe, and the presence of CYP3A-HACΔ was visually observed. It was thus concluded that CHO cell clones retaining CYP3A-HACΔ were obtained.

(D) Transfer of CYP3A-HACΔ from CHO Cell to Mouse ES Cell

In order to construct a chimeric mouse retaining CYP3A-HACΔ, CYP3A-HACΔ obtained in (C) above were transferred from the CHO cells retaining the same to mouse ES cells (wild-type TT2F) by the microcell method. In accordance with the method of Tomizuka et al. (Nature Genet. 16: 133, 1997), microcells were purified from about $10^8$ of CHO cells retaining CYP3A-HACΔ (e.g., CHO/CYP3A-HACΔ4, 6, 7, and 10) and suspended in 5 ml of DMEM. Mouse ES cells (TT2F, about $10^7$ cells) were peeled via trypsin treatment, washed three times with DMEM, suspended in 5 ml of DMEM, added to the centrifuged microcells, and centrifuged at 1,250 rpm for 10 minutes to completely remove the supernatant. The precipitate was thoroughly loosened via tapping, 0.5 ml of 1:1.4 PEG solution (a solution of 5 g of PEG1000 (Wako Pure Chemical Industries, Ltd. (Japan)) and 1 ml of DMSO (Sigma) in 6 ml of DMEM) was added, and the mixture was thoroughly agitated for about 1 minute and 30 seconds. Thereafter, 10 ml of DMEM was slowly added, the mixture was centrifuged at 1,250 rpm for 10 minutes, the resultant was suspended in 30 ml of ES medium, the suspension was fractionated into three petri dishes having a diameter of 100 mm (Corning) seeded with feeder cells, and culture was conducted. The medium was exchanged with a medium containing G418 at 300 μg/ml 24 hours thereafter, and selective culture was carried out for about 1 week. As a result, 4 clones resulting from CHO/CYP3A-HACΔ4, 4 clones resulting from CHO/CYP3A-HACΔ6, 3 clones resulting from CHO/CYP3A-HACΔ7, and 4 clones resulting from CHO/CYP3A-HACΔ10 were found positive via PCR using the primer for detecting the CYP3A gene cluster and the primer for detecting human chromosome 14. As a result of FISH analysis using the human COT1 DNA probe (Tomizuka et al., Nature Genet. 16: 133, 1997), the presence of CYP3A-HACΔ detected specifically by the COT1 probe was observed in 15 of the 15 clones. Among such clones, 3 clones exhibited normal mouse karyotypes. It was thus concluded that 3 clones of TT2F cells retaining CYP3A-HACΔ were obtained (E) Production of Chimeric Mouse Retaining Human Artificial Chromosome, CYP3A-HACΔ

Chimeric mice were produced by the method of Tomizuka et al. (Nature Genet. 16: 133, 1997) using the ES cell clones obtained in (D). As the host cells, 8-cell stage embryos obtained via male and female crossing of MCH (ICR) mice (white, purchased from CLEA Japan, Inc.) were used. Whether or not progeny mice resulting from transplantation of the injected embryos into foster parents are chimeric mice can be determined based on hair color. Wild-type TT2F/CYP3A-HACΔ clones (e.g., F8/CYP3A-HACΔ-7 and 11, obtained in (D) above) were injected into 800 embryos, and such embryos were transplanted into foster mothers. As a result, 92 chimeric mice were born (dark brown color was observed in hair). Among them, 10 individuals had percentages of chimerism of about 100% in which substantially no white portion was observed. Specifically, ES cell lines (TT2F) retaining the human artificial chromosome (CYP3A-HACΔ) have the capacity for chimera formation; i.e., the capacity for differentiating into mouse normal tissue.

(F) Retention of Artificial Chromosome in Somatic Cells of Chimeric Mouse Constructed from ES Cell Retaining Human Artificial Chromosome (CYP3A-HACΔ)

(F.1) Genome PCR Analysis

Genomic DNA was prepared from tails of chimeric mice (percentage of chimerism=about 80%) constructed from TT2F/CYP3A-HACΔ clones (F8/CYP3A-HACΔ-7 and 11) in (E) by the method of Tomizuka et al. (Nature Genet. 16: 133, 1997), and PCR was carried out in the same manner as described above with the use of the primer for detecting the CYP3A gene cluster and the primer for detecting human chromosome 14 to examine CYP3A-HACΔ retention. As a result, the genomic DNA of interest was found to be positive for two types of primers and retention of CYP3A-HACΔ was observed in somatic cells of the chimeric mice.

(F.2) Fluorescent in Situ Hybridization (FISH) Analysis

As a result of FISH analysis using the liver tissue of two chimeric mice exhibiting the percentage of chimerism of about 80% by the method of Shinohara et al. (Human Molecular Genetics: 10, 1163-1175, 2001) using the human COT1 DNA probe, the presence of CYP3A-HACΔ was visually observed, and the percentage of CYP3A-HACΔ retention was 70% in both chimeric mice, which was substantially consistent with the percentage of chimerism. The percentage of chimerism indicates a contribution rate of ES cells to tissue (body hair) and the percentage of retention indicates a contribution rate of the introduced chromosome to tissue. Use of a chimeric mouse exhibiting a high percentage of chimerism and a high percentage of retention is considered to result in more efficient differentiation of ES cells retaining the introduced chromosome into germ cells and transmission of the introduced chromosome to progeny. Specifically, use of CYP3A-HACΔ can enhance the efficiency for transmission of a human chromosome fragment containing the CYP3A gene to mouse progeny.

(G) Transmission of Artificial Chromosome from Chimeric Mouse Retaining Human Artificial Chromosome, CYP3A-HACΔ, to Progeny The 4 female chimeric mice prepared in (E) above (percentage of chimerism=about 100%) were subjected to crossing with male MCH (ICR) mice (white, purchased from CLEA Japan, Inc.). Among the 80 progeny mice born from chimeric mice, 75 progeny mice showed dark brown color, indicating an ES-cell-derived dominant genotype. That is, ES cell lines retaining CYP3A-HACΔ were found to have been differentiated into functional egg cells in female chimeric mice. Tails of the 75 dark brown progeny mice were partially cut, and genomic DNA was prepared from the samples. The DNA was subjected to PCR in the manner described above with the use of the primer for detecting the CYP3A gene cluster and the primer for detecting human chromosome 14, and retention of CYP3A-HACΔ was examined. As a result, 24 mice were found to be positive for both primers and retention of CYP3A-HACΔ in progeny chimeric mice was confirmed. The mouse strain that had inherited CYP3A-HACΔ is designated as TC(CYP3A-HACΔ).

Example 3

Figure 6:
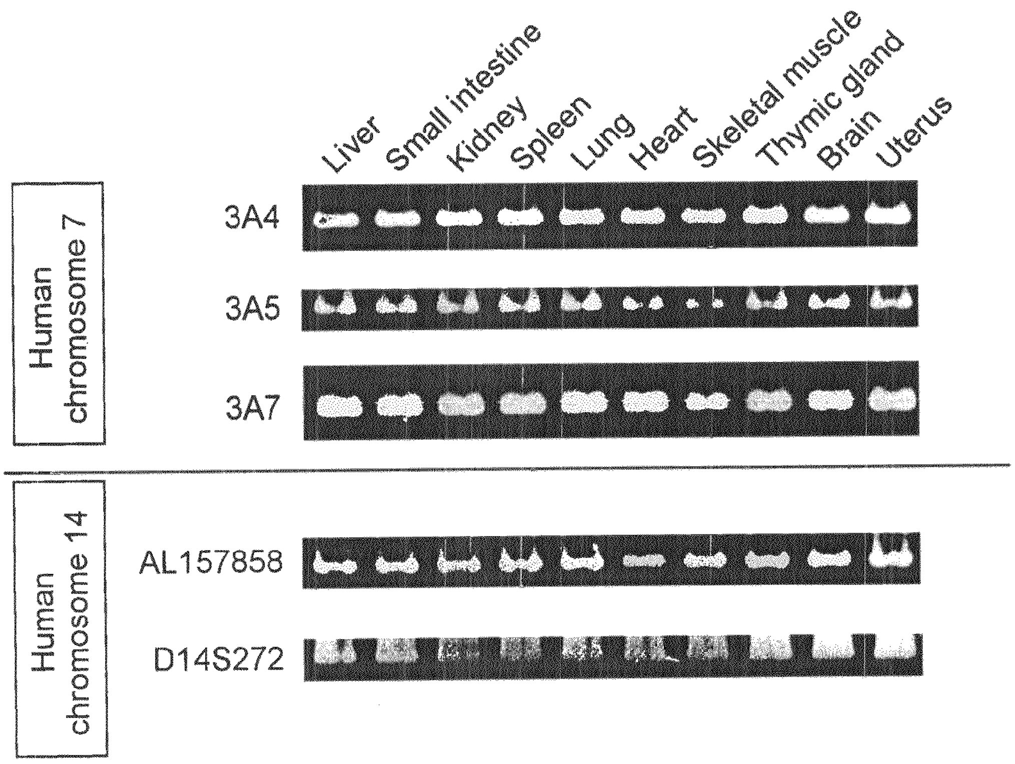
FIG. 6 shows the results of genomic analysis of the CYP3A gene cluster of the TC (CYP3A-HACΔ) mouse.

Retention of CYP3A-HACΔ in Somatic Cell of TC(CYP3A-HACΔ) Mouse Strain (3.1) Genome PCR Analysis A male mouse (165) and a female mouse (155) of the TC(CYP3A-HACΔ) mice obtained above were subjected to PCR under the above conditions using the genomes obtained from the brain, the thymic gland, the heart, the lung, the liver, the kidney, the spleen, the small intestine, the muscle, and the spermary (or uterus) as templates and the primer for detecting the CYP3A gene cluster and the primer for detecting human chromosome 14. CYP3A-HACΔ was detected in all organs. Representative results of the female (155) are shown in FIG. 6.

(3.2) Fluorescent in Situ Hybridization (FISH) Analysis

Figure 7:
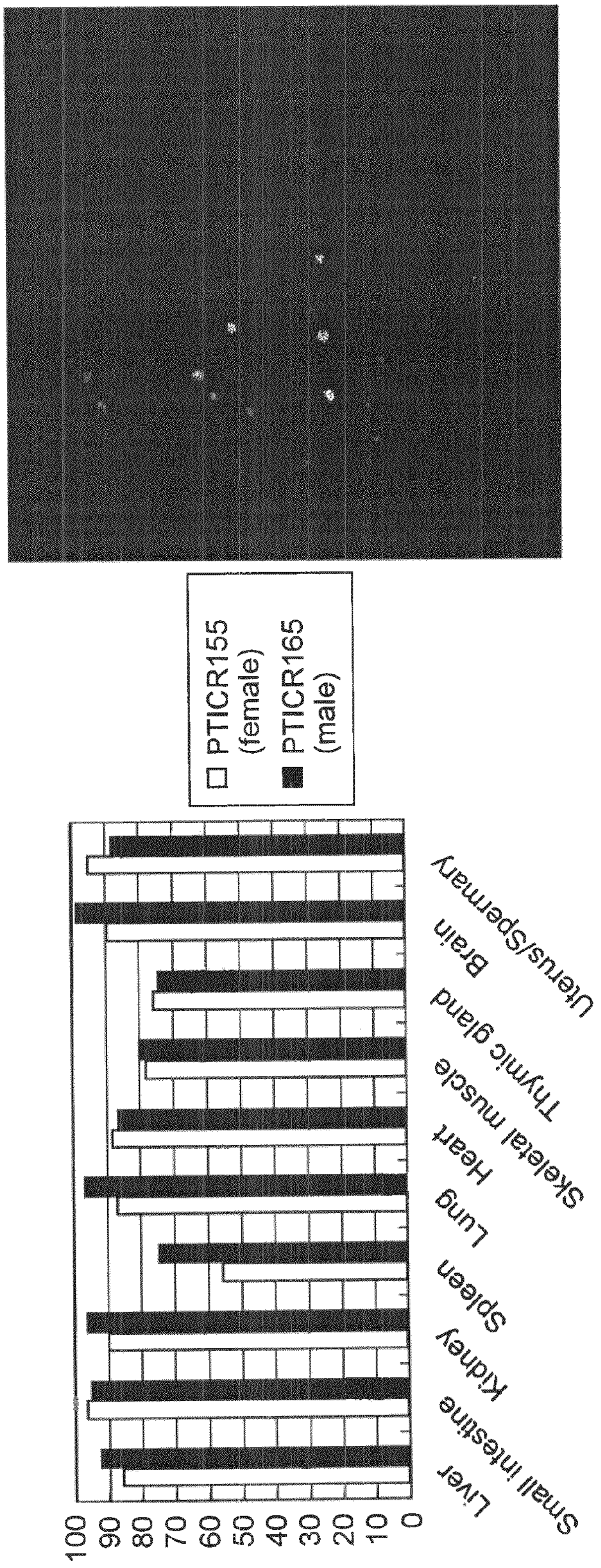
FIG. 7 shows FISH analysis of the TC(CYP3A-HACΔ) mouse. The left panel shows the percentage of CYP3A-HACΔ retention (the vertical axis) in each tissue (the horizontal axis) analyzed via FISH. The right panel is a photograph showing the results of FISH of tail fibroblasts of the TC(CYP3A-HACΔ) mouse.

As a result of FISH analysis using the individuals and tissues that were employed above by the method of Shinohara et al. (Human Molecular Genetics, 10, 1163-1175, 2001) using the human COT1 DNA probe, 55 to 95% of the individuals were found to retain CYP3A-HACΔ (FIG. 7). In the liver and the small intestine in which CYP3A is mainly expressed, in particular, the percentage of chromosome retention was as high as at least 85%. As a result of FISH analysis that was carried out in the same manner as described above with the use of tail fibroblasts prepared from TC(CYP3A-HACΔ), the presence of CYP3A-HACΔ was visually observed, and the presence thereof independent of a mouse chromosome was confirmed (FIG. 7).

Example 4

Tissue Specific Expression of CYP3A Gene Cluster in TC(CYP3A-HACΔ) Mouse Strain Total RNA was extracted from the brain, the thymic gland, the heart, the lung, the liver, the kidney, the spleen, the small intestine, the muscle, and the spermary (or uterus) of a male mouse (165) and a female mouse (155) of the TC(CYP3A-HACΔ) mice obtained above in accordance with a commercially available protocol (QIAGEN), cDNA was synthesized in accordance with a commercially available protocol (Invitrogen), and PCR was carried out using the synthesized cDNA as a template to detect expression of the human CYP3A gene cluster and of the mouse Cyp3a gene cluster. The primer sequences are shown below. Primers for detecting human CYP3A gene cluster expression:

```
3A4-1L:   gtatggaaaagtgtggggct  (SEQ ID NO: 57)
3A4-1R:   atacttcaagaattgggatg  (SEQ ID NO: 58)
3A4-2L:   ccaagctatgctcttcaccg  (SEQ ID NO: 59)
3A4-2R:   tgaagaagtcctcctaagct  (SEQ ID NO: 60)
3A5-1L:   ctctgtttccaaaagatacc  (SEQ ID NO: 61)
3A5-1R:   tcaacatctttcttgcaagt  (SEQ ID NO: 62)
3A7-1L:   agcttttaagatttaatcca  (SEQ ID NO: 63)
3A7-1R:   gagctttgtgggtctcagag  (SEQ ID NO: 64)
3A7-2L:   ctctcagaattcaaaagact  (SEQ ID NO: 65)
3A7-2R:   agaagaagtcctccaaagcg  (SEQ ID NO: 66)
3A43-2L:  tatgacacaactagcaccac  (SEQ ID NO: 67)
3A43-2R:  agtgtctagtgttctgggat  (SEQ ID NO: 68)
```

Primers for detecting mouse Cyp3a gene cluster expression:

```
3a11-1L: tcaaacgcctctccttgctg   (SEQ ID NO: 69)
3a11-1R: gcttgcctttctttgccttc   (SEQ ID NO: 70)
3a11-2L: ggtaaagtacttgaggcaga   (SEQ ID NO: 71)
```

-continued

```
3a11-2R: agaaagggctttatgagaga   (SEQ ID NO: 72)
3a13-1L: agaaacatgaggcagggatt   (SEQ ID NO: 73)
3a13-1R: acaaggagacatttagtgca   (SEQ ID NO: 74)
3a13-2L: taccccagtatttgatgcac   (SEQ ID NO: 75)
3a13-2R: agataactgactgagccaca   (SEQ ID NO: 76)
3a25-1L: cttctacatatatgggacct   (SEQ ID NO: 77)
3a25-1R: accgacggtttgtgaagact   (SEQ ID NO: 78)
3a25-2L: agaaagaacgccttgcttca   (SEQ ID NO: 79)
3a25-2R: ttgggcagagttctgtca     (SEQ ID NO: 80)
3a44-1L: cactggatacattggtcctg   (SEQ ID NO: 81)
3a44-1R: cgtgatgacaaggagaggtg   (SEQ ID NO: 82)
3a44-2L: agaggatccttttgtggagg   (SEQ ID NO: 83)
3a44-2R: ctttggaattattatgagaa   (SEQ ID NO: 84)
```

Primers for detecting control gene expression:

```
GAPDH-F:
5'-CCATCTTCCAGGAGCGAGA-3'    (SEQ ID NO: 85)

GAPDH-R:
5'-TGTCATACCAGGAAATGAGC-3'   (SEQ ID NO: 86)
```

PCR was carried out using the GeneAmp 9600 Thermal Cycler (Perkin-Elmer), EX Tag polymerase (Takara Shuzo Co., Ltd.), and buffer or dNTPs (dATP, dCTP, dGTP, and dTTP) included in the kit in accordance with the recommended conditions. A cycle of thermal denaturation at 93° C. for 5 minutes, followed by 93° C. for 1 minute, 56° C. for 1 minute, and 72° C. for 1 minute was repeated 35 times.

Figure 8:
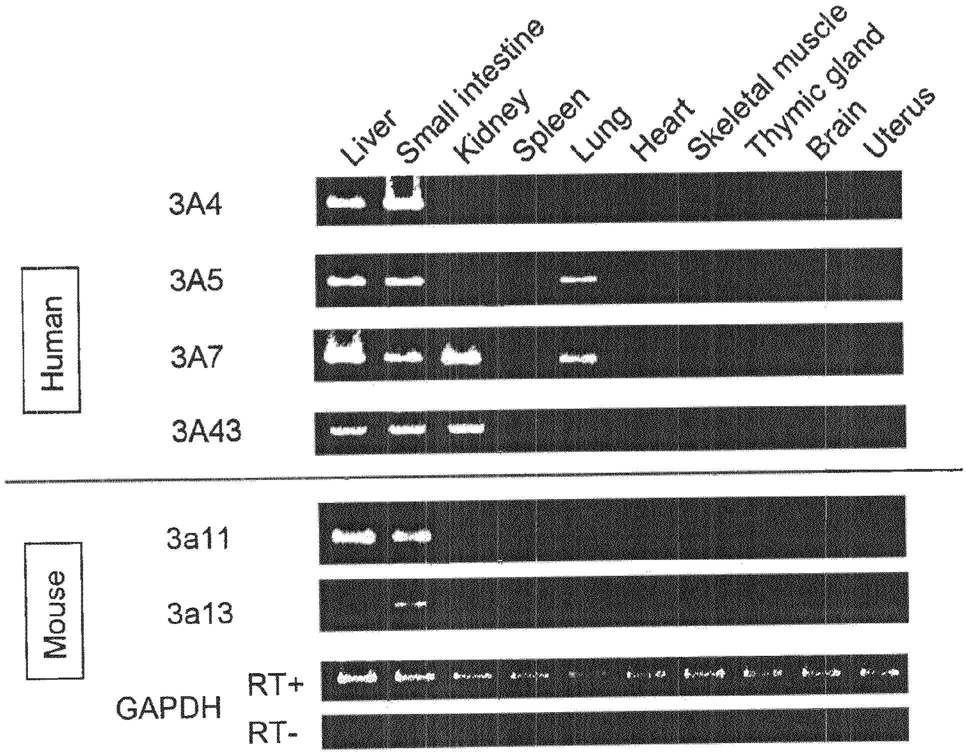
FIG. 8 shows the results of expression analysis of the CYP3A gene cluster of the TC (CYP3A-HACΔ) mouse, wherein "GAPDH" stands for glyceraldehyde 3-phosphate dehydrogenase.

As a result, CYP3A4 expression was observed only in the liver and the small intestine, CYP3A5 expression was observed only in the liver, the small intestine, and the lung, CYP3A7 expression was observed only in the liver, the small intestine, the kidney, and the lung, CYP3A43 expression was observed only in the liver, the small intestine, and the kidney, Cyp3a11 expression was observed only in the liver and the small intestine, Cyp3a13 expression was observed only in the liver and the small intestine, Cyp3a25 expression was observed only in the liver and the small intestine, and Cyp3a44 expression was observed only in the liver and the small intestine of a mouse retaining TC(CYP3A-HACΔ). Also, control GAPDH was detected in all tissues. Representative results of the female (155) are shown in FIG. 8. Thus, tissue-specific expression as observed in human was observed, which indicates humanization.

Example 5

Stage-Specific CYP3A Gene Cluster Expression in TC(CYP3A-HACΔ) Mouse Strain (5.1) Genome PCR Analysis PCR was carried out using the genomes obtained from the liver of the male and female TC(CYP3A-HACΔ) mice at the age of embryonic day 14.5, embryonic day 16.5, embryonic day 18.5, 0-day-old, 2-week-old, 4-week-old, 6-week-old, 8-week-old, and 24-week-old as templates and using the primer for detecting the CYP3A gene cluster and the primer for detecting human chromosome 14 under the conditions as above, and CYP3A-HACΔ was detected at all stages.

(5.2) RT-PCR Analysis

Total RNA was extracted from the liver of the individuals same as above in accordance with a commercially available protocol (QIAGEN), cDNA was synthesized in accordance with a commercially available protocol (Invitrogen), PCR was carried out using the synthesized cDNA as a template, and expression of the human CYP3A gene cluster and of the mouse Cyp3a gene cluster was detected with the use of the primers for detecting expression of the same.

Figure 9:
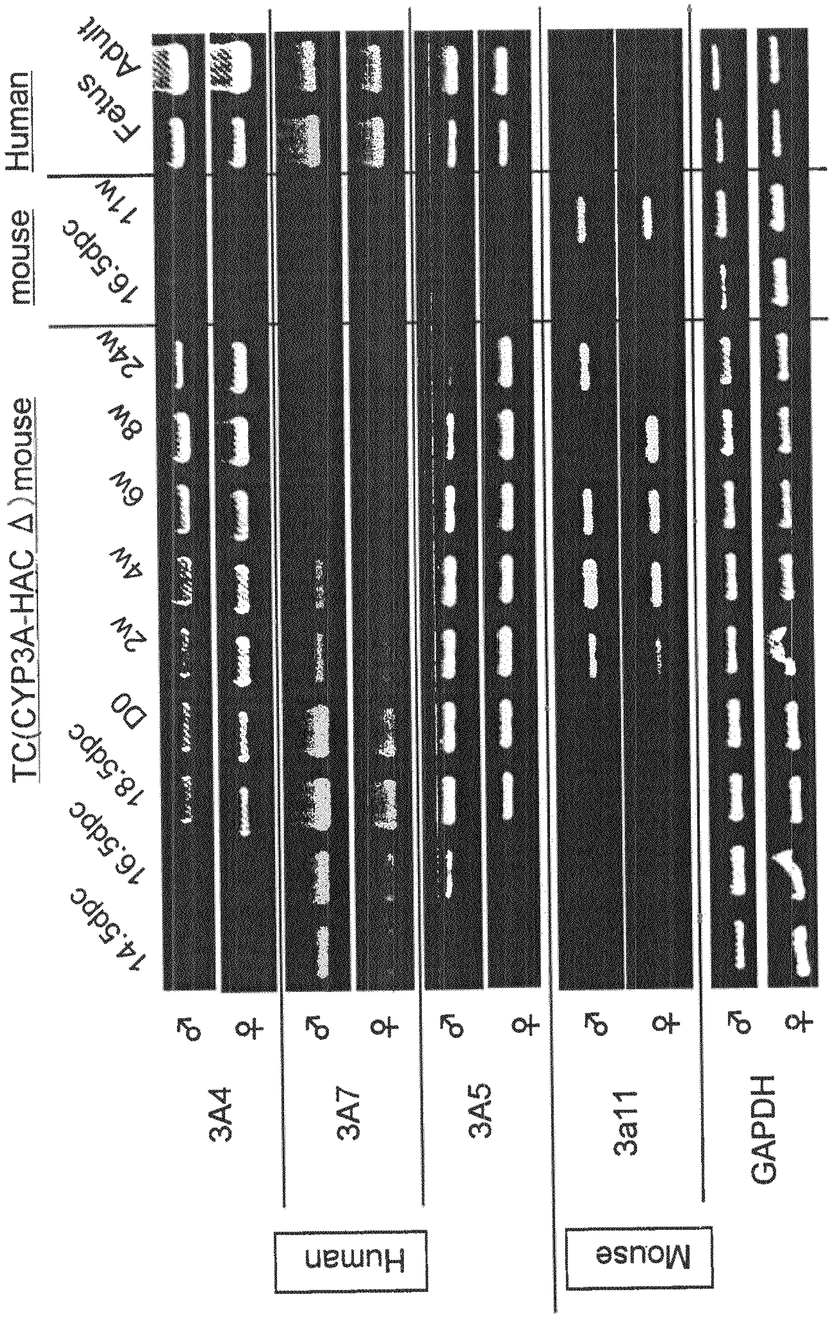
FIG. 9 shows the results of stage-specific gene expression analysis of the CYP3A gene cluster in the liver of the TC(CYP3A-HACΔ) mouse.

As a result, expression of adult-specific human CYP3A4, human CYP3A5, mouse cyp3a11, and mouse Cyp3a13 was found to be potent at the adult stage, and that of fetal-specific CYP3A7 was found to be potent at the embryonic stage. Expression levels of control GAPDH were substantially the same at all stages. Representative results thereof are shown in FIG. 9. Thus, stage-specific expression as observed in humans was observed, which indicates humanization.

Example 6

Induction of CYP3A Gene Cluster Expression in TC(CYP3A-HACΔ) Mouse Strain

Figure 10:
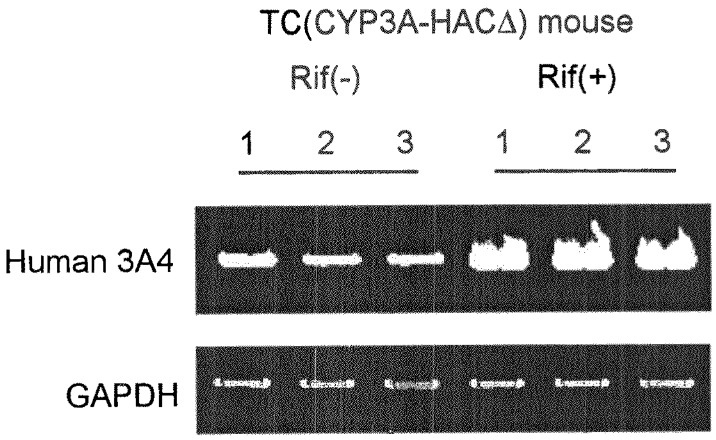
FIG. 10 shows the results of analysis of drug-induced gene expression in the liver of the TC(CYP3A-HACΔ) mouse, wherein "Rif" stands for rifampicin.

In order to investigate the influence of rifampicin (Sigma), which is known as a substance inducing human CYP3A4 expression, on CYP3A4 gene expression in TC (CYP3A-HACΔ) mice, rifampicin was administered intraperitoneally for 4 days in amounts of 100 mg/kg per dose. A suspension of rifampicin "Rif" in corn oil (Sigma) was prepared for administration. The liver was extracted from mice on day 5, total RNA was extracted in accordance with a commercially available protocol (QIAGEN), cDNA was synthesized in accordance with a commercially available protocol (Invitrogen), PCR was carried out using the synthesized cDNA as a template, and human CYP3A gene expression was detected using the primers detecting the same. As a result, expression of the human CYP3A4 gene was found to be more potent in the TC(CYP3A-HACΔ) group to which rifampicin had been administered, compared with a TC(CYP3A-HACΔ) group to which a solvent (i.e., corn oil) had been administered. Expression levels of control GAPDH were substantially the same in both groups. Representative results of 3 male mice (of the group to which rifampicin had been administered and of the group to which oil had been administered) are shown in FIG. 10.

Thus, induction of human CYP3A gene expression was found to be humanized in TC (CYP3A-HACΔ).

Example 7

Construction of Mouse Strain in which Both Alleles of Endogenous Cyp3a13 Gene Had been Disrupted (7.1) Cloning of DNA Fragment Containing Cyp3a13 Gene Exon 1 Region In order to add new restriction enzyme sites to pBluescript II SK (−) (Toyobo Co., Ltd., Japan), the following DNAs were synthesized.

```
LinkA1:
5'-TCGAGTCGCGACACCGGCGGGCGCGCCC-3'   (SEQ ID NO: 87)

LinkA2:
5'-TCGAGGGCGCGCCCGCCGGTGTCGCGAC-3'   (SEQ ID NO: 88)
```

-continued

```
LinkB1:
5'-GGCCGCTTAATTAAGGCCGGCCGTCGACG-3'  (SEQ ID NO: 89)

LinkB2:
5'-AATTCGTCGACGGCCGGCCTTAATTAAGC-3'  (SEQ ID NO: 90)
```

pBluescript II SK (−) was treated with the SalI and XhoI restriction enzymes, and the resulting reaction solution was separated on 0.8% gel to recover a gel containing a vector DNA fragment. The vector DNA fragment was purified from the recovered gel using the QIAquick Gel Extraction Kit (QIAGEN, Germany) in accordance with the attached instructions. Separately, in order to add new restriction enzyme sites; i.e., NruI, SgrAI, and AscI, to the plasmid, 100 μmol each of the two types of oligo DNAs (LinkA1 and LinkA2) were added to 20 μl of the reaction solution, the resultant was incubated for 45 minutes in total (i.e., 70° C. for 15 minutes→37° C. for 15 minutes→room temperature for 15 minutes), the resulting DNA fragment was inserted into the pBluescript II SK (−) plasmid, which had been treated with the restriction enzymes, and the resultant was introduced into *E. coli* DH5α. DNA was prepared from the resulting transformant, and the pBlueLA plasmid was obtained.

Figure 11:
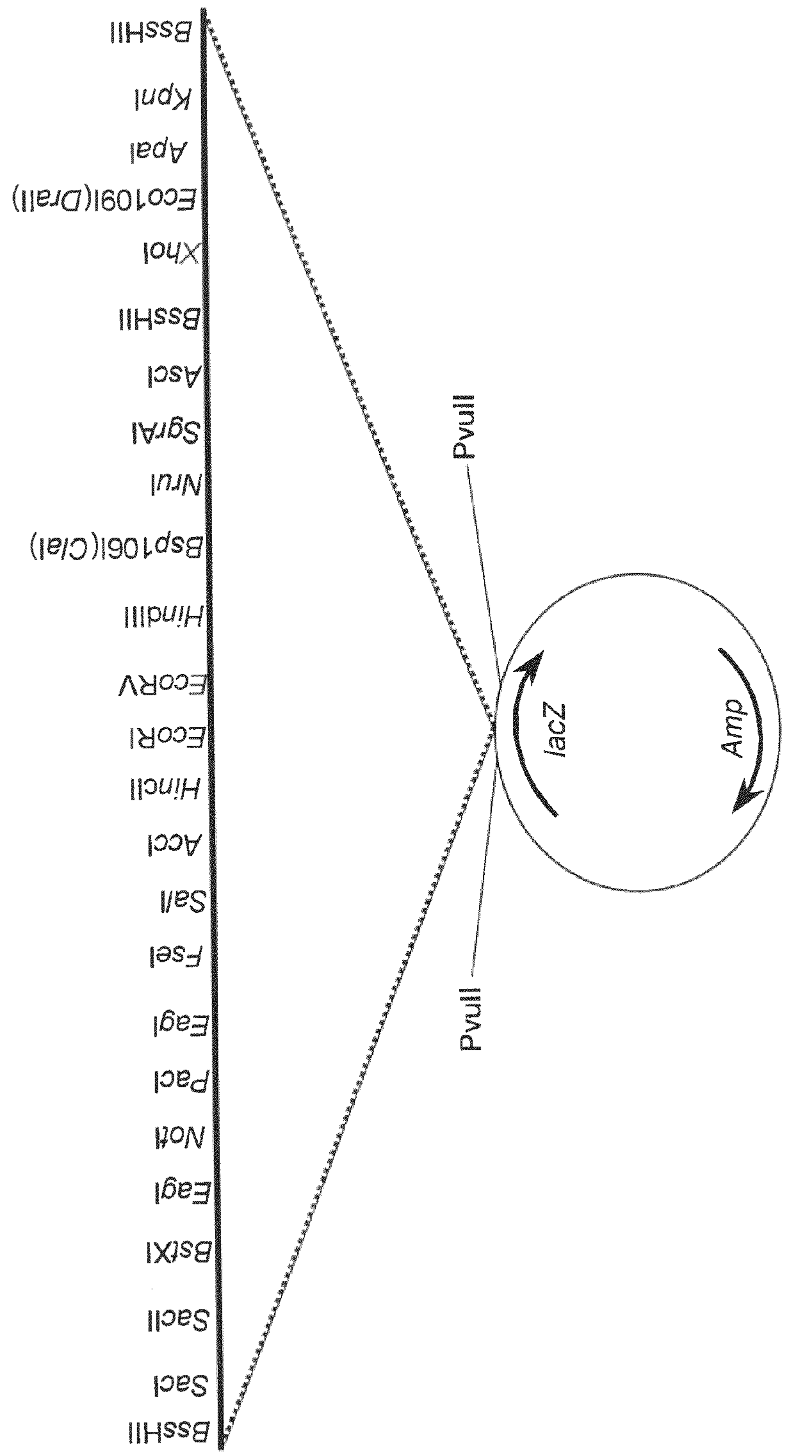
FIG. 11 shows the structure of the pBlueLAB (2975 bp) multicloning site.

Subsequently, pBlueLA was treated with the NotI and EcoRI restriction enzymes, and the resulting reaction solution was separated on 0.8% gel to recover a gel containing a vector DNA fragment. The vector DNA fragment was purified from the recovered gel using the QIAquick Gel Extraction Kit (QIAGEN, Germany) in accordance with the attached instructions. In order to add new restriction enzyme sites; i.e., PacI, FseI, and SalI, to the plasmid, 100 μmol each of the two types of oligo DNAs (LinkB1 and LinkB2) were added to 20 μl of the reaction solution, the resultant was incubated for 45 minutes in total (i.e., 70° C. for 15 minutes→37° C. for 15 minutes→room temperature for 15 minutes), the resulting DNA fragment was inserted into the pBlueLA plasmid, which had been treated with the restriction enzymes, and the resultant was introduced into *E. coli* DH5α. DNA was prepared from the resulting transformant, and the pBlueLAB plasmid was obtained (FIG. 11).

Figure 12:
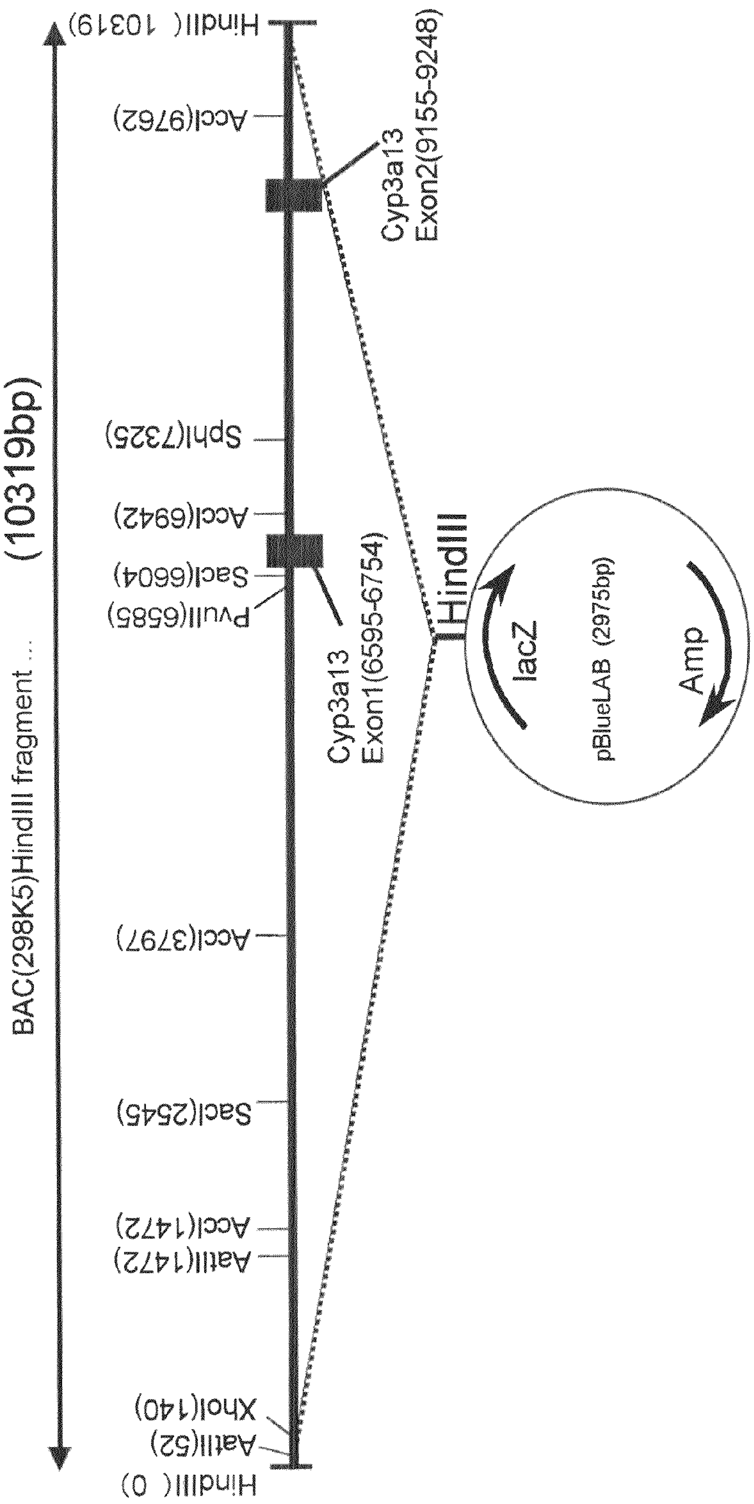
FIG. 12 shows the structure of pBACcyp3a13 (#39).

BAC clone, RP23-425N17 (purchased from Advanced GenoTechs Co.), was treated with HindIII, and the resulting reaction solution was separated on 0.8% gel to recover a gel containing a DNA fragment containing a DNA fragment (10,319 bp) including a region in the vicinity of the mouse Cyp3a13 gene. The DNA fragment was purified from the recovered gel using the QIAquick Gel Extraction Kit (QIAGEN, Germany) in accordance with the attached instructions. The obtained fragment was inserted into the HindIII site of pBlueLAB to obtain pBACcyp3a13 (#39) (FIG. 12).

(7.2) Construction of pBlueLAB (SAAX)

In order to modify the restriction enzyme sites of pBlueLAB prepared in 7.1 above, the following oligo DNAs were synthesized.

```
3'SacI-XhoI linker S:
5'-CGGCGCGCCGTATACC-3'          (SEQ ID NO: 91)

Figure 13:
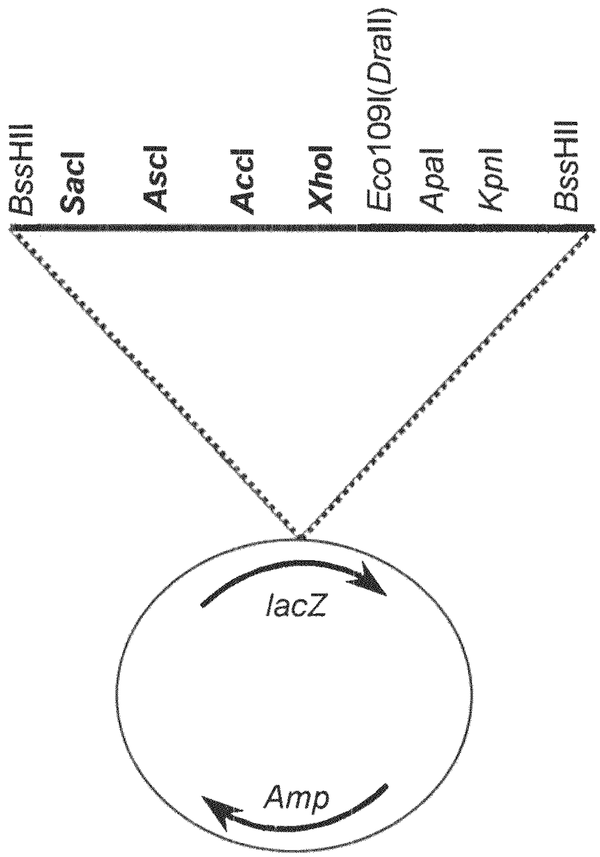
FIG. 13 shows the structure of the pBlueLAB (SAAX) multicloning site.

3'SacI-XhoI linker A:
5'-TCGAGGTATACGGCGCGCCGAGCT-3'  (SEQ ID NO: 92)
``` pBlueLAB was treated with the SacI and XhoI restriction enzymes, and the resulting reaction solution was separated on 0.8% gel to recover a gel containing a vector DNA fragment. The vector DNA fragment was purified from the recovered gel using the QIAquick Gel Extraction Kit (QIAGEN, Germany) in accordance with the attached instructions. Separately, 100 μmol each of the two types of oligo DNAs were added to 20 μl of the reaction solution, the resultant was incubated for 45 minutes in total (i.e., 70° C. for 15 minutes→37° C. for 15 minutes→room temperature for 15 minutes), the resulting DNA fragment was inserted into the vector, which had been treated with SacI and XhoI, and the resultant was introduced into *E. coli* DH5α. DNA was prepared from the resulting transformant, and the pBlueLAB (SAAX) plasmid was obtained (FIG. 13).

(7.3) Construction of pBlueLAB (NAPF)

In order to modify the restriction enzyme sites of pBlueLAB prepared in 7.1 above, the following oligo DNAs were synthesized.

```
5'NotIAscI linker36 S (5' phosphorylation):
                                    (SEQ ID NO: 93)
5'-GCGGCCGCGACGTCCAGCTGGGCCGGCCGGCGCGCC-3'

Figure 14:
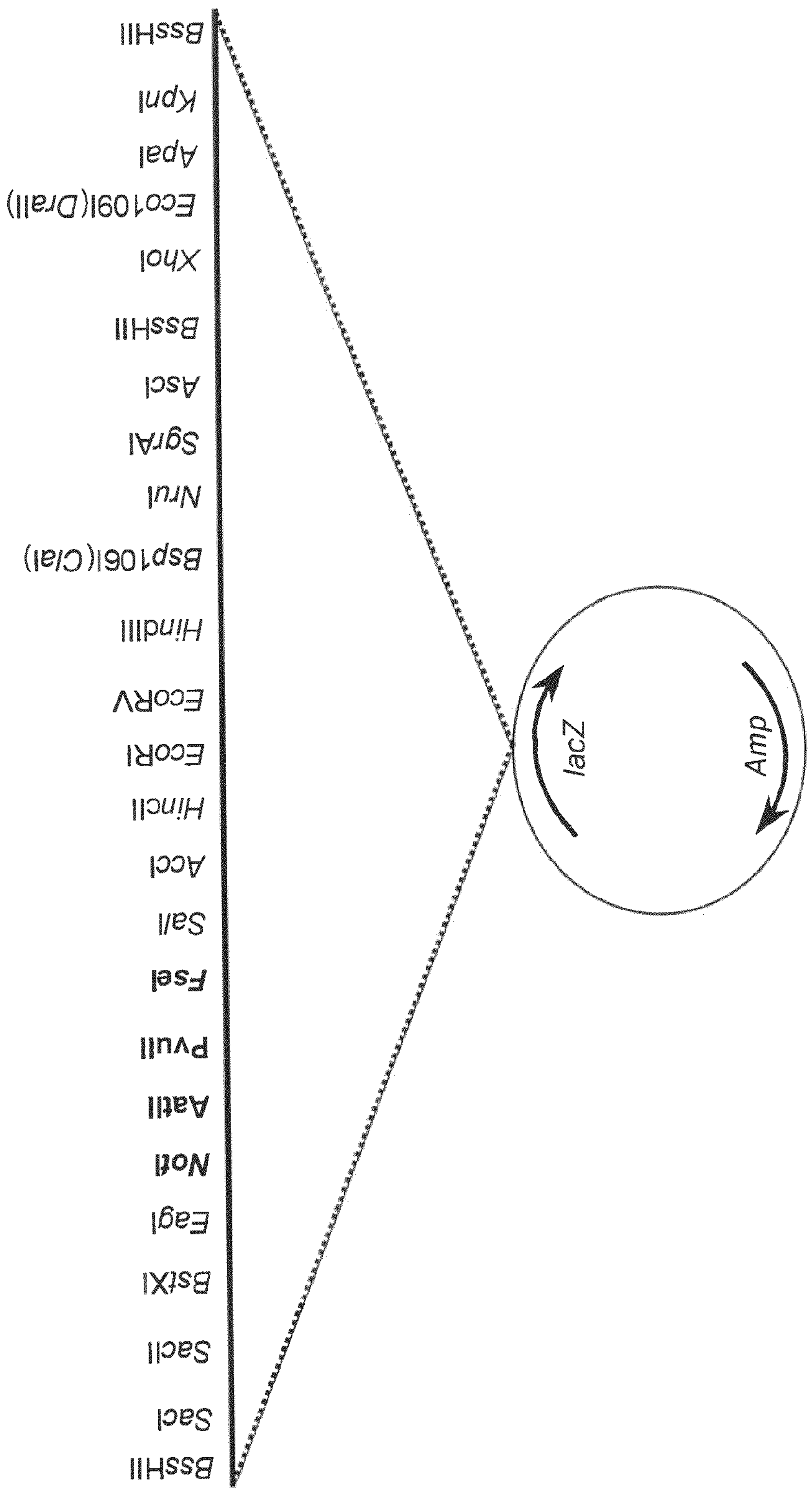
FIG. 14 shows the structure of the pBlueLAB (NAPF) multicloning site.

5'NotIAscI linker36 A (5' phosphorylation):
                                    (SEQ ID NO: 94)
5'-GGCGCGCCGGCCGGCCCAGCTGGACGTCGCGGCCGC-3'
``` pBlueLAB was treated with the PvuII restriction enzyme, and the resulting reaction solution was separated on 0.8% gel to recover a gel containing a vector DNA fragment. The vector DNA fragment was purified from the recovered gel using the QIAquick Gel Extraction Kit (QIAGEN, Germany) in accordance with the attached instructions. The purified vector DNA was treated with alkaline phosphatase (calf intestine-derived, Takara) and subjected to phenol/chloroform extraction and ethanol precipitation. Separately, 100 μmol each of the two types of oligo DNAs were added to 20 μl of the reaction solution, the resultant was incubated for 45 minutes in total (i.e., 70° C. for 15 minutes→37° C. for 15 minutes→room temperature for 15 minutes), the resulting DNA fragment was inserted into the plasmid, which had been treated with the PvuII restriction enzyme, and the resultant was introduced into *E. coli* DH5α. DNA was prepared from the resulting transformant, and the pBlueLAB (NAPF) plasmid was obtained (FIG. 14).

(7.4) Preparation of DNA Fragment of Cyp3a13 (Exon 1 to Intron 1) Region and Insertion Thereof into pBlueLAB (SAAX)

In order to prepare DNA containing part of the Cyp3a13 (exon 1 to intron 1) region, the following oligo DNAs were synthesized.

```
3a13 3' (AscI)Fw1:
                                    (SEQ ID NO: 95)
5'-GGCGCGCCCTCCTGGCTACCAGCCTGGTCCTTCTC-3'

3a13 3' (AccI)Rw1:
                                    (SEQ ID NO: 96)
5'-GTATACTTACTTACCCCATAGGAGGGATTTGCATAGGACC-3'
```

A reaction solution was prepared with the use of KOD-plus- (Toyobo Co., Ltd., Japan) in accordance with the attached instructions, 1.5 μl each of the above two types of primers (10 μmol) and pBACcyp3a13 (#39) prepared in 7.1 above as a template were added to 50 μl of the reaction solution, the mixture was heated at 94° C. for 2 minutes, an amplification cycle of 94° C. for 15 seconds, 60° C. for 1 minute, and 68° C. for 1 minute was repeated 30 times, and the resulting 209-bp amplified fragment was separated on 0.8% gel and then recovered. The amplified fragment was recovered from the gel using the QIAquick Gel Extraction Kit (QIAGEN, Germany) in accordance with the attached instructions. The recovered PCR-amplified fragment was digested with the AscI and AccI enzymes and separated on 0.8% agarose gel and then recovered. A DNA fragment was recovered from the gel using the QIAquick Gel Extraction Kit (QIAGEN, Germany) in accordance with the attached instructions.

pBlueLAB (SAAX) was treated with the AscI and AccI restriction enzymes, and the resulting reaction solution was separated on 0.8% gel to recover a gel containing a vector DNA fragment. The vector DNA fragment was purified from the recovered gel using the QIAquick Gel Extraction Kit (QIAGEN, Germany) in accordance with the attached instructions. The DNA fragment prepared above (including part of the Cyp3a13 exon 1 to intron 1 region) was inserted into the purified vector, and the resultant was introduced into *E. coli* DH5α. DNA was prepared from the resulting transformant to obtain the pBlueLAB plasmid (SAAX)cyp3a13 (209 bp).

(7.5) Insertion of DNA Fragment (110 bp) Containing Cyp3a13-5' Genomic Region into pBlueLAB (NAPF)

In order to prepare a DNA fragment (110 bp) containing the Cyp3a13-5' genomic region, the following oligo DNAs were prepared.

```
3a13 PvuII-ex1 S:
                                    (SEQ ID NO: 97)
5'-CTGGGCAGGGAAGGGAGCTCAGCAGGCTCAGCCCTGAAAGGTGCA

GCACACAAAATTGAGAGTACAACTTGGAGAGAGACTTGTTTAAAGAAA

ACAGCAGGCCGG-3'

3a13 PvuII-ex1 A:
                                    (SEQ ID NO: 98)
5'-CCTGCTGTTTTCTTTAAACAAGTCTCTCTCCAAGTTGTACTCTCA

ATTTTGTGTGCTGCACCTTTCAGGGCTGAGCCTGCTGAGCTCCCTTCC

CTGCCCAG-3'
```

pBlueLAB (NAPF) was treated with the PvuII and FseI restriction enzymes, and the resulting reaction solution was separated on 0.8% gel to recover a gel containing a vector DNA fragment. The vector DNA fragment was purified from the recovered gel using the QIAquick Gel Extraction Kit (QIAGEN, Germany) in accordance with the attached instructions. Separately, 100 μmol each of the two types of oligo DNAs were added to 20 μl of the reaction solution, the resultant was incubated for 45 minutes in total (i.e., 70° C. for 15 minutes→37° C. for 15 minutes→room temperature for 15 minutes), the resulting DNA fragment (110 bp) was inserted into the plasmid, which had been treated with PvuII and FseI, and the resultant was introduced into *E. coli* DH5α. DNA was prepared from the resulting transformant, and the pBlueLAB (NAPF) cyp3a13 plasmid (110 bp) was obtained.

(7.6) Insertion of 3' Genomic Fragment (Approximately 2.8 kb) Derived from pBACcyp3a13 (#39) into pBlueLAB (SAAX)Cyp3a13 (209 bp)

pBlueLAB (SAAX)cyp3a13 (209 bp) prepared in 7.4 above was treated with the AccI restriction enzyme, and the resulting reaction solution was separated on 0.8% gel to recover a gel containing a vector DNA fragment. The vector DNA fragment was purified from the recovered gel using the QIAquick Gel Extraction Kit (QIAGEN, Germany) in accordance with the attached instructions. The purified vector DNA was treated with alkaline phosphatase (calf intestine-derived, Takara) and subjected to phenol/chloroform extraction and ethanol precipitation. Separately, pBACcyp3a13 (#39) was treated with the AccI restriction enzyme, and the resulting reaction solution was separated on 0.8% gel to recover a gel containing a DNA fragment of approximately 2.8 kb containing part of exon 1 and exon 2 of the Cyp3a13 gene. The DNA fragment (2.8 kb) was purified from the recovered gel using the QIAquick Gel Extraction Kit (QIAGEN, Germany) in accordance with the attached instructions. The resulting DNA fragment (2.8 kb) was inserted into the AccI-treated plasmid and the resultant was introduced into *E. coli* DH5α. DNA was prepared from the resulting transformant, and the pBlueLAB (SAAX)cyp3a13 plasmid (2.8 kb) was obtained.

(7.7) Insertion of 5' Genomic Fragment (Approximately 5.1 kb) Derived from pBACcyp3a13 (#39) into pBlueLAB (NAPF)cyp3a13 (110 bp)

pBlueLAB (NAPF)cyp3a13 (110 bp) prepared in 7.5 above was treated with the AatII and PvuII restriction enzymes, and the resulting reaction solution was separated on 0.8% gel to recover a gel containing a vector DNA fragment. The vector DNA fragment was purified from the recovered gel using the QIAquick Gel Extraction Kit (QIAGEN, Germany) in accordance with the attached instructions. Separately, pBACcyp3a13 (#39) was treated with the AatII and PvuII restriction enzymes, and the resulting reaction solution was separated on 0.8% gel to recover a gel containing a DNA fragment of approximately 5.1 kb containing the 5' region and part of exon 1 of the Cyp3a13 gene. The DNA fragment (5.1 kb) was purified from the recovered gel using the QIAquick Gel Extraction Kit (QIAGEN, Germany) in accordance with the attached instructions. The resulting DNA fragment (5.1 kb) was inserted into the plasmid treated with AatII and PvuII and the resultant was introduced into *E. coli* DH5α. DNA was prepared from the resulting transformant, and the pBlueLAB (NAPF)Cyp3a13 plasmid (5.1 kb) was obtained.

(7.8) Construction of Basic KO Vector

The pLoxP-STneo plasmid disclosed in WO 00/10383 was digested with XhoI to obtain the Neo-resistant gene (LoxP-Neo) having loxP sequences at both ends. The both ends of LoxP-Neo were blunt-ended with the use of T4 DNA polymerase to obtain a LoxP-Neo-B fragment.

Figure 15:
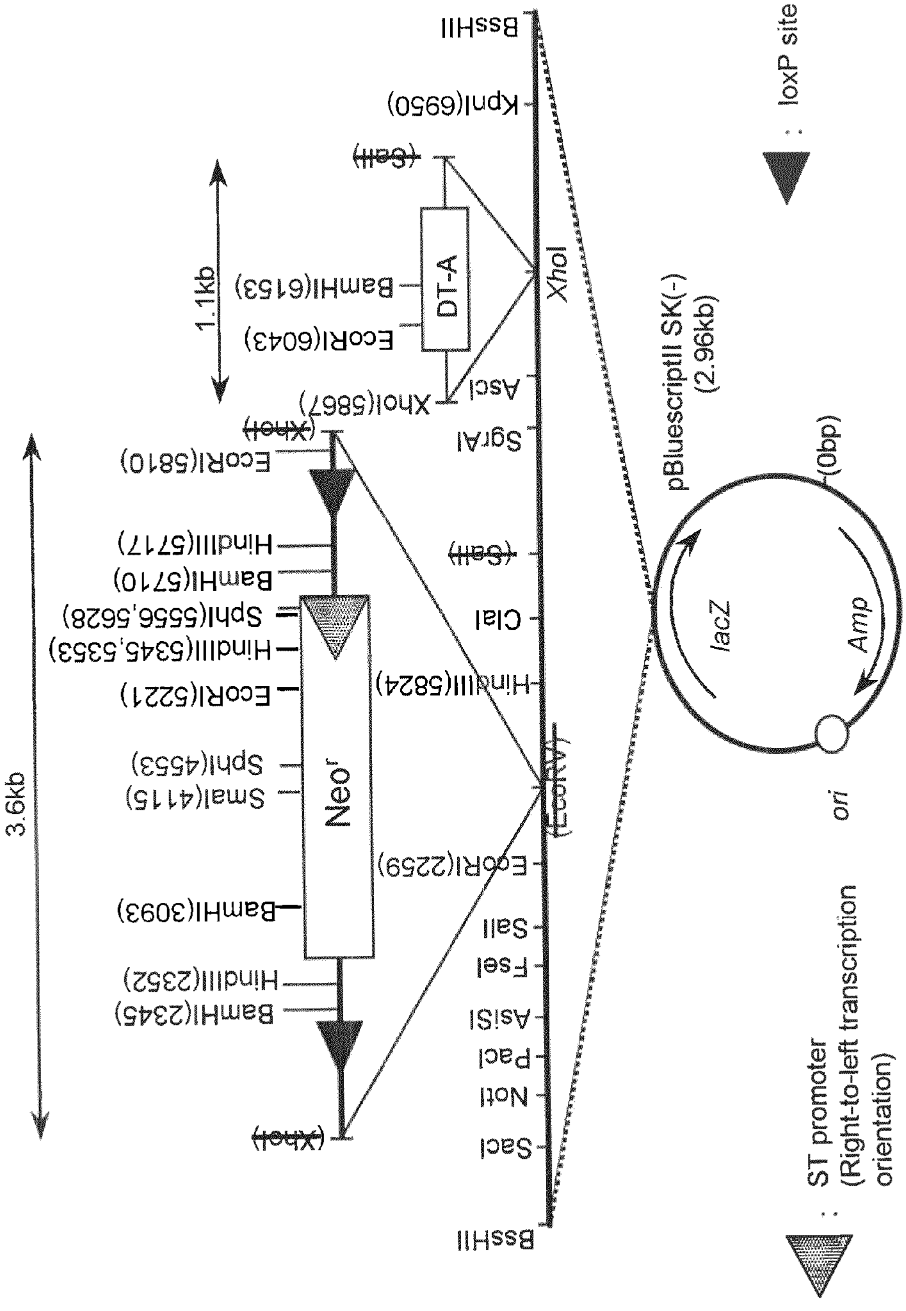
FIG. 15 shows the structure of pBlueLAB-LoxP-Neo-DT-A (R) (7602 bp).

After pBlueLAB was digested with EcoRV, the reaction solution was subjected to phenol/chloroform extraction and ethanol precipitation, the LoxP-Neo-B fragment was inserted, and the resultant was introduced into *E. coli* DH5α. Among the obtained transformants, DNA was prepared from positive clones comprising a promoter that drives the Neo-resistant gene at the ClaI site of the vector, and the pBlueLAB-LoxP-Neo (R) plasmid was obtained.

pMC1DT-A (Life Technologies Oriental, INC.) was digested with XhoI and SalI, the digestion product was applied on 0.8% agarose gel, a band of approximately 1 kb was separated and recovered, and a DT-A fragment was recovered using the QIAquick Gel Extraction Kit (QIAGEN, Germany) in accordance with the attached instructions. pBlueLAB-LoxP-Neo (R) was digested with XhoI, the reaction solution was subjected to phenol/chloroform extraction and ethanol precipitation, the DT-A fragment was inserted, and the resultant was introduced into *E. coli* DH5α. DNA was prepared from the resulting transformant, and a basic KO vector, pBlueLAB-LoxP-Neo-DT-A (R), was obtained (FIG. 15).

(7.9) Insertion of Cyp3a13-3' Genomic Fragment (Approximately 3.0 kb: AscI-XhoI) and Cyp3a13-3' Genomic Fragment (Approximately 5.2 kb: NotI-FseI) into pBlueLAB-LoxP-Neo-DT-A (R)

pBlueLAB (SAAX)cyp3a13 (2.8 kb) was treated with the AscI and XhoI restriction enzymes, and the resulting reaction solution was separated on 0.8% gel to recover a gel containing a DNA fragment of approximately 3.0 kb containing part of exon 1 and exon 2 of the Cyp3a13 gene. An AscI-XhoI DNA fragment (3.0 kb) was purified from the recovered gel using the QIAquick Gel Extraction Kit (QIAGEN, Germany) in accordance with the attached instructions. Further, pBlueLAB (NAPF)cyp3a13 (5.1 kb) was treated with the NotI and FseI restriction enzymes, and the resulting reaction solution was separated on 0.8% gel to recover a gel containing a DNA fragment of approximately 5.2 kb containing the 5' region and part of exon 1 of the Cyp3a13 gene. A NotI-FseI DNA fragment (5.2 kb) was purified from the recovered gel using the QIAquick Gel Extraction Kit (QIAGEN, Germany) in accordance with the attached instructions.

The basic KO vector, pBlueLAB-LoxP-Neo-DT-A (R) plasmid, was treated with the AscI and XhoI restriction enzymes, and the resulting reaction solution was separated on 0.8% gel to recover a gel containing a vector DNA fragment. The vector DNA fragment was purified from the recovered gel using the QIAquick Gel Extraction Kit (QIAGEN, Germany) in accordance with the attached instructions. The resulting AscI-XhoI DNA fragment (3.0 kb) was inserted into the plasmid treated with AscI and XhoI and the resultant was introduced into *E. coli* DH5α. DNA was prepared from the resulting transformant, and the pBlueLAB-LoxP-Neo-DT-A (R)+3' genome plasmid was obtained.

Figure 16:
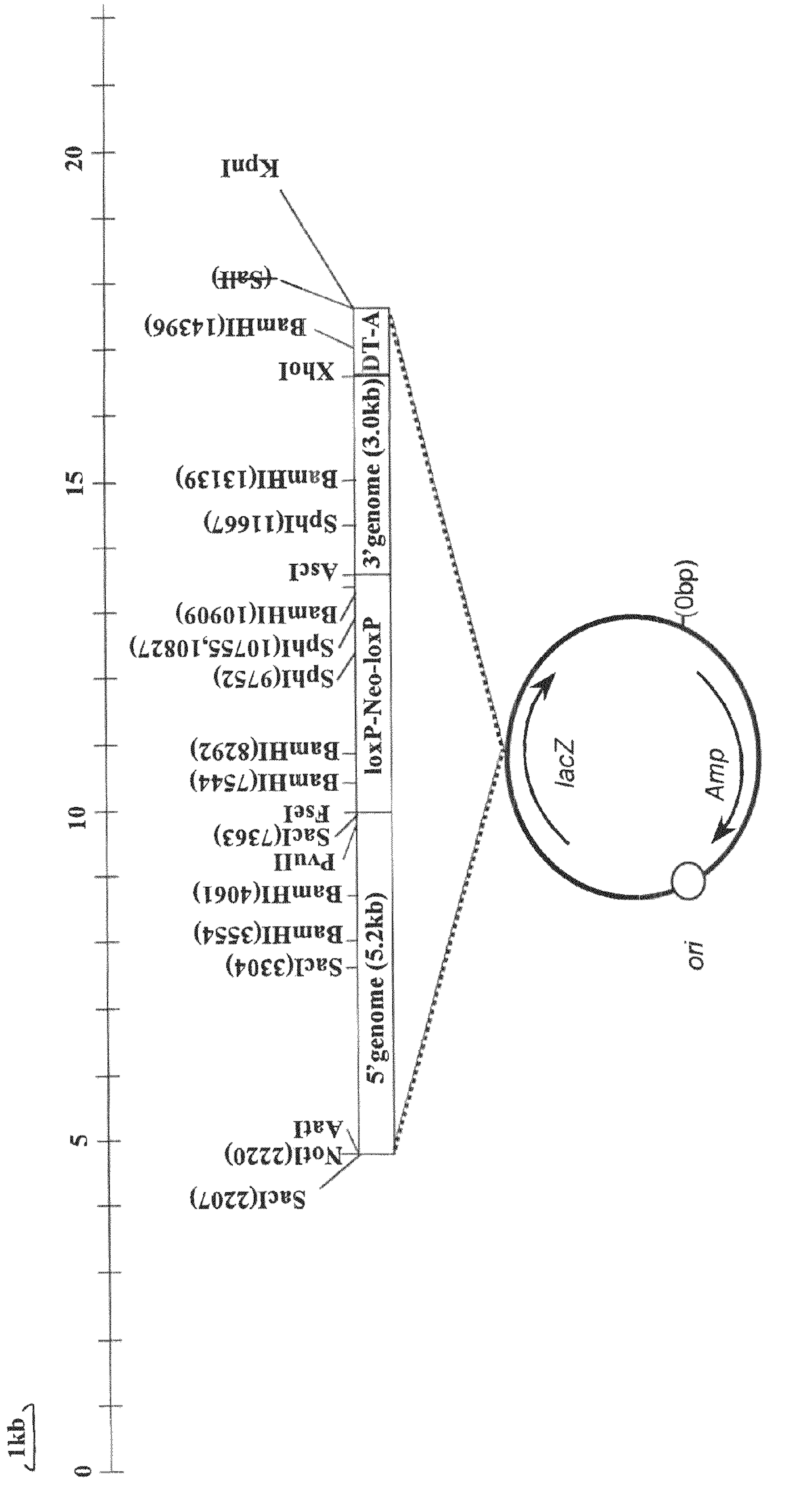
FIG. 16 shows the structure of pcyp3a13-KO (approximately 15.8 kb).

The above pBlueLAB-LoxP-Neo-DT-A (R)+3' genome plasmid was treated with the NotI and FseI restriction enzyme, and the resulting reaction solution was separated on 0.8% gel to recover a gel containing a vector DNA fragment. The vector DNA fragment was purified from the recovered gel using the QIAquick Gel Extraction Kit (QIAGEN, Germany) in accordance with the attached instructions. The resulting NotI-FseI DNA fragment (5.2 kb) was inserted into the plasmid, which had been treated with NotI and FseI, and the resultant was introduced into *E. coli* DH5α. DNA was prepared from the resulting transformant, and the pcyp3a13-KO plasmid was obtained (FIG. 16).

(7.10) Preparation of Probe Used for Genomic Southern Analysis

Based on the nucleotide sequence information of the BAC clone, RP23-425N17 (Genbank Accession Number: AC125063), the following DNAs were synthesized in order to obtain a DNA fragment of approximately 1.2 kb containing the Cyp3a13-5' genomic region.

```
3a13 5'probe6 Fw:
5'-CCCTCCTTGTCACTGATGCT-3'     (SEQ ID NO: 99)

3a13 5'probe6 Rv:
5'-TCTGGGAGGACAGAATGCTT-3'     (SEQ ID NO: 100)
```

A reaction solution was prepared with the use of KOD-plus- (Toyobo Co., Ltd., Japan) in accordance with the attached instructions, 1.5 μl each of the above two types of primers (10 μmol) and pBACcyp3a13 (#39) prepared in 7.1 above as a template were added to 50 μl of the reaction solution, the mixture was heated at 94° C. for 2 minutes, an amplification cycle of 94° C. for 15 seconds, 60° C. for 30 seconds, and 68° C. for 2 minutes was repeated 30 times, and the resulting amplified fragment of approximately 1.2 kb was separated on 0.8% gel and then recovered. The amplified fragment (a probe for 5' genomic Southern analysis: 5'KO-probe, FIG. 17) was recovered from the gel using the QIAquick Gel Extraction Kit (QIAGEN, Germany) in accordance with the attached instructions.

Based on the nucleotide sequence information of the BAC clone, RP23-425N17 (Genbank Accession Number:

AC125063), the following DNAs were synthesized in order to obtain a DNA fragment of approximately 1.2 kb containing the Cyp3a13-3' genomic region.

```
3a13 3'probe3 Fw:
5'-TCACACATCTCTAGATGACTACGG-3'     (SEQ ID NO: 101)

3a13 3'probe3 Rv2:
5'-ATAGACTGCCATGGAGGAAC-3'         (SEQ ID NO: 102)
```

A reaction solution was prepared with the use of KOD-plus- (Toyobo Co., Ltd., Japan) in accordance with the attached instructions, 1.5 μl each of the above two types of primers (10 μmol) and pBACcyp3a13 (#39) prepared in 7.1 above as a template were added to 50 μl of the reaction solution, the mixture was heated at 94° C. for 2 minutes, an amplification cycle of 94° C. for 15 seconds, 60° C. for 30 seconds, and 68° C. for 2 minutes was repeated 30 times, and the resulting amplified fragment of approximately 1.2 kb was separated on 0.8% gel and then recovered. The amplified fragment (a probe for 3' genomic Southern analysis: 3'KO-probe, FIG. 17) was recovered from the gel using the QIAquick Gel Extraction Kit (QIAGEN, Germany) in accordance with the attached instructions.

(7.11) Gene Targeting Using Cyp3a13-KO Vector

Mouse ES cells can be generally established in the following manner. Embryos 2.5 days after fertilization resulting from crossing of male and female mice were sampled, the embryos were cultured in vitro in ES cell culture medium, the embryos that had advanced to the blastocysts were separated from the cultured embryos, such the embryos were sowed and cultured in feeder cell medium, cell masses that had grown in an ES-like manner were dispersed using ES cell culture medium containing trypsin, culture was conducted using feeder cell medium, and subculture was further carried out using ES cell culture medium to isolate the grown cells.

In order to obtain ES cells of the pcyp3a13-knockout mouse via homologous recombination, pcyp3a13-KO was linearized with the NotI restriction enzyme (Takara Shuzo Co., Ltd.), and the resultant was introduced into the mouse ES cells, TT2 (Yagi et al., Analytical Biochem., 214: 70, 1993) in accordance with the established method (Bio-Manual Series 8, Gene targeting, Shinichi Aizawa, Yodosha (Japan), 1995). TT2 cells were cultured in accordance with the method (Shinichi Aizawa, ibid) using the G418-resistant primary cultured cells (purchased from Invitrogen) treated with mitomycin C (Sigma, U.S.A.) as nursing cells. At the outset, the grown TT2 cells were treated with trypsin and suspended in HBS at concentration of 3×10' cells/ml. Thereafter, 0.5 ml of a cell suspension was mixed with 10 μg of vector DNA, and electroporation was carried out using gene pulser cuvettes (electrode distance: 0.4 cm, Bio-Rad, U.S.A.) (capacitance: 960 μF; voltage: 240 V; room temperature). The cells that had been subjected to electroporation were suspended in 10 ml of ES medium and the resulting suspension was sowed on a 100-mm plastic petri dish for tissue culture (Falcon, Beckton Dickinson, U.S.A.) seeded with feeder cells. The medium was exchanged with ES medium containing neomycin (200 μg/ml, Sigma, U.S.A.) 24 hours later. The colonies generated 7 days later were picked up, grown on a 24-well plate to reach confluence, two-thirds thereof were suspended in 0.2 ml of storage medium (FBS+10% DMSO, Sigma, U.S.A.), and the suspension was stored at −80° C. The remaining one-thirds was sowed on a 12-well gelatin-coated plate, culture was conducted for 2 days, and genomic DNA was prepared from $10^6$ to $10^7$ cells using the Puregene DNA Isolation Kits (Gentra System, U.S.A.).

Figure 17:
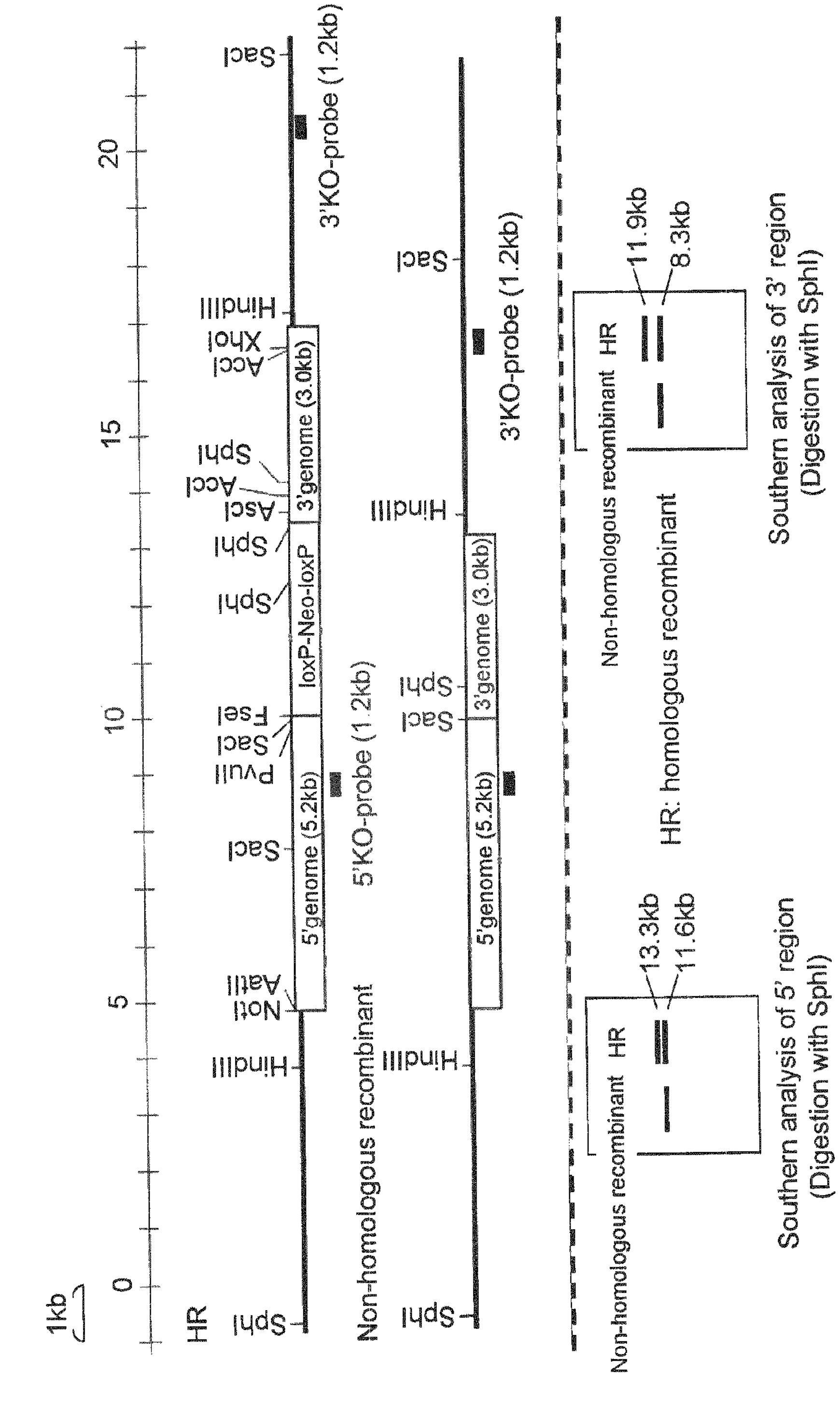
FIG. 17 schematically shows Southern analysis of the genome of the ES cell line of the homologous recombinant (HR) using the cyp3a13-KO vector.

Genomic DNA of the resulting neomycin-resistant TT2 cells was digested with the SacI restriction enzyme (Takara Shuzo Co., Ltd.) and separated on 0.8% agarose gel electrophoresis. Subsequently, Southern blot analysis was carried out to detect a homologous recombinant using a DNA fragment (3'KO-probe, FIG. 17) located downstream of the 3' homologous region of the targeting vector as a probe. A band (approximately 8.3 kb) was detected via digestion with SacI in the wild-type TT2F cell. It was deduced that two bands (approximately 8.3 kb and approximately 11.9 kb) would be detected in a homologous recombinant, and a new band of approximately 11.9 kb was observed in the neomycin-resistant strain (FIG. 17). Further, genomic DNA of the clone in which homologous recombination was observed via Southern analysis using 5'KO-probe was digested with the SphI restriction enzyme (Takara Shuzo Co., Ltd.) and separated on 0.8% agarose gel electrophoresis. Subsequently, Southern blot analysis was carried out to detect a homologous recombinant using a DNA fragment (5'KO-probe) located upstream of the 5' homologous region of the targeting vector as a probe. A band (approximately 11.6 kb) was detected via digestion with SacI in the wild-type TT2F cell. It was deduced that two bands (approximately 11.6 kb and approximately 13.3 kb) would be detected in a homologous recombinant, and a new band of approximately 13.3 kb was observed in the neomycin-resistant strain (FIG. 17). Specifically, such clone lacks a region in the vicinity of the initiation codon of exon 1 of the mouse Cyp3a13 gene and comprises the neomycin-resistant gene (comprising the restriction enzyme sites derived from the targeting vector at both ends) inserted therein. As a result of Southern blot analysis using 3' and 5'KO-probes, 5 of the 60 strains were found to be homologous recombinants when the vector prepared by linearizing pcyp3a13-KO with the NotI restriction enzyme was used.

(7.12) Construction of Chimeric Mouse Using Pcyp3a13-KO ES Cell Line

The G418-resistant mouse ES cell lines (#4, #16, #25, #36, and #42) obtained in 7.11 above were established from frozen stocks, and such cells were injected into the 8-cell stage embryos resulting from crossing of male and female MCH (ICR) mice (CLEA Japan, Inc.) in amounts of 8 to 10 cells per embryo. Culture was conducted in ES medium (Bio-Manual Series 8, Gene targeting, Shinichi Aizawa, Yodosha (Japan), 1995) overnight to develop into blastocysts, and about 10 injected embryos were transplanted to each of the uteri of the foster parent MCH (ICR) mouse (CLEA Japan, Inc.) 2.5 days after the pseudopregnancy treatment in amounts of about 10 cells per uterus. Chimeric individuals are identified based on the presence of a wild-type color (dark brown) derived from ES cells in white color derived from the host embryo. As a result of transplantation experiment, a total of 37 chimeric mice were born from 5 types of ES cell lines.

(7.13) Transmission of pcyp3a13-KO Allele from Chimeric Mouse Derived from cyp3a13-KO ES Cell Line to Progeny Among the chimeric mice derived from the pcyp3a13-KO ES cell lines (#4, #42) prepared in 7.12 above, male individuals exhibiting the percentage of chimerism of 100% (#4:9 mice; #42:1 mouse) were subjected to crossing with female C57BL/6N mice (CLEA Japan, Inc.), and whether or not progeny having the pcyp3a13-KO alleles derived from the ES cells would be born was investigated. Genomic DNA obtained from the tails of the progeny mice resulting from such crossing was subjected PCR analysis using the following primers.

3'genome2:
5'-AGTTCCAGAGGGACACCTTC-3' (SEQ ID NO: 103)

neo3-1:
5'-TTCCACACCTGGTTGCTGAC-3' (SEQ ID NO: 104)

5'down:
5'-AGATTCAAGTGGGCACACCC-3' (SEQ ID NO: 105)

Figure 18:
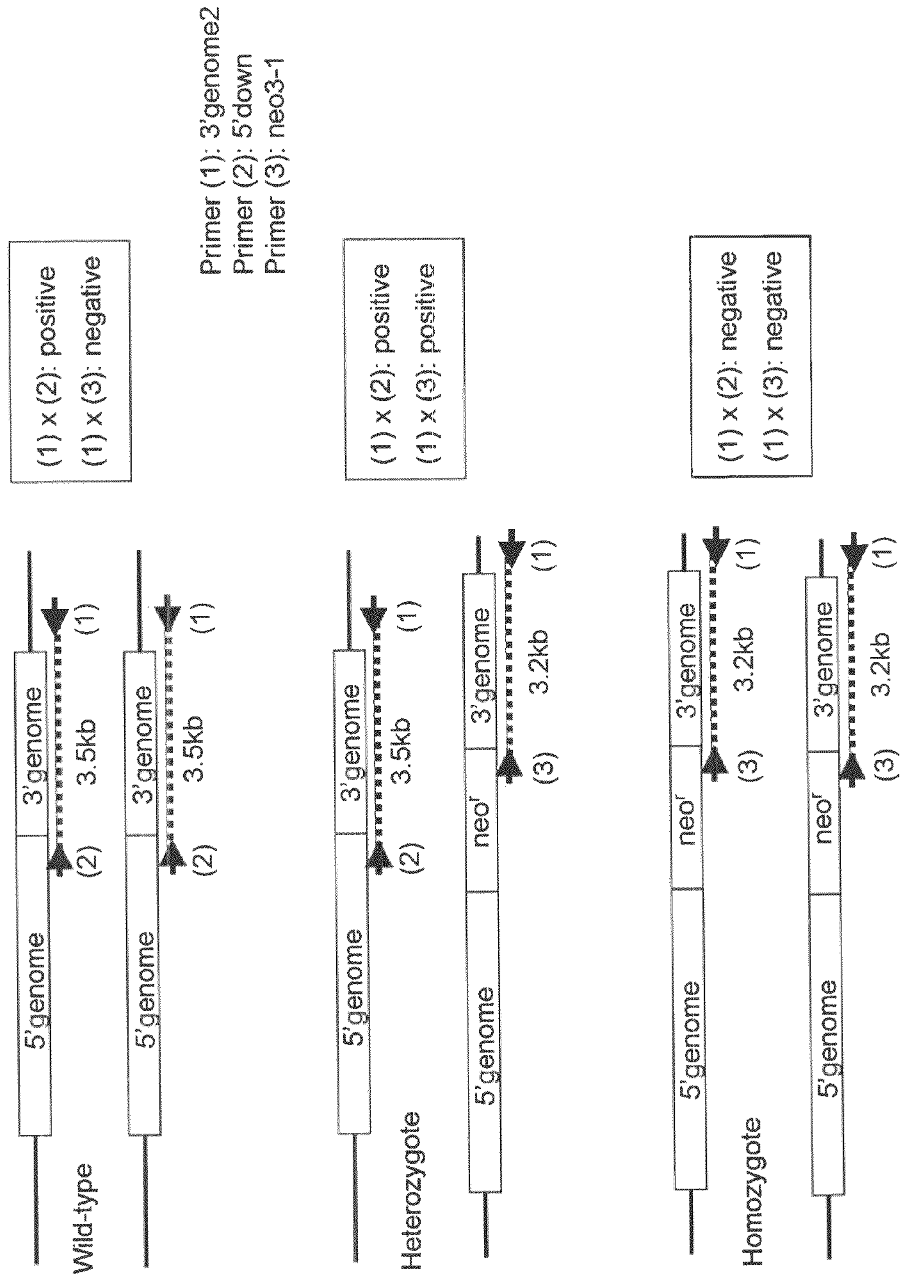
FIG. 18 schematically shows the genotype analysis of the cyp3a13-KO mouse individual.

A reaction solution (30 μl) was prepared using LA-Taq (Takara Bio, Japan) in accordance with the attached instructions, a combination of 3' genome2 and 5' down (FIG. 18, (1)×(2)) or a combination of 3' genome2 and neo3-1 (FIG. 18, (1)×(3)) was added as the primer pair, the genomic DNA of the progeny mice was added as the template, the mixture was heated at 94° for 5 minutes, and an amplification cycle of 94° for 30 seconds, 60° C. for 30 seconds, and 72° C. for 3 minutes was repeated 35 times. The reaction solution was electrophoresed on 0.8% gel to detect an amplification product. A specific product of 3.5 kb was detected regarding the wild-type Cyp3a13 allele with the use of the (1)×(2) primer combination, and a specific product of 3.2 kb was detected regarding the KO-type Cyp3a13 allele with the use of the (1)×(3) primer combination (FIG. 18). As a result of analysis of DNA obtained from the tail of the progeny mice that were born from the chimeric mice #4 and #42 derived from the ES cell lines, the existence of the cyp3a13-KO heterozygotes that were positive for both (1)×(2) and (1)×(3) primer combinations was observed (FIG. 18).

(7.14) Construction of cyp3a13/44/11/25-KO Mouse Via Crossing of cyp3a13-KO Mouse and cyp3a44/11/25-KO Mouse The method for constructing the cyp3a44/11/25-KO mouse that simultaneously lacks Cyp3a44, Cyp3a11, and Cyp3a25 of the genes of the mouse Cyp3a family is disclosed by WO 01/011951. The Cyp3a44, Cyp3a11, and Cyp3a25 genes form the cluster on mouse chromosome 5 together with other two types of genes of the Cyp3a family (3a16 and 3a41), and the distance between the Cyp3a family gene cluster and the Cyp3a13 gene is about 10 Mb.

Regarding the genomic DNA prepared from the tail of the progeny mouse resulting from crossing of the cyp3a13-KO heterozygous mouse with the cyp3a44/11/25-KO heterozygous mouse constructed in 7.12 above, PCR analysis described in 7.13 (FIG. 18) was performed in order to determine the genotype of the Cyp3a13 locus. Based on the results, the cyp3a13-KO heterozygote (FIG. 18) that was positive for both (1)×(2) and (1)×(3) primer combinations was selected. Further, the following PCR analysis was carried out in order to determine the genotype of the Cyp3a44/11/25 locus.

3a25 Fw:
5'-CATTGTTCTGGCTTTAGCGTC-3' (SEQ ID NO: 106)

3a25 Rv:
5'-CTGCAACCCTGAGGCTTTAG-3' (SEQ ID NO: 107)

Figure 19:
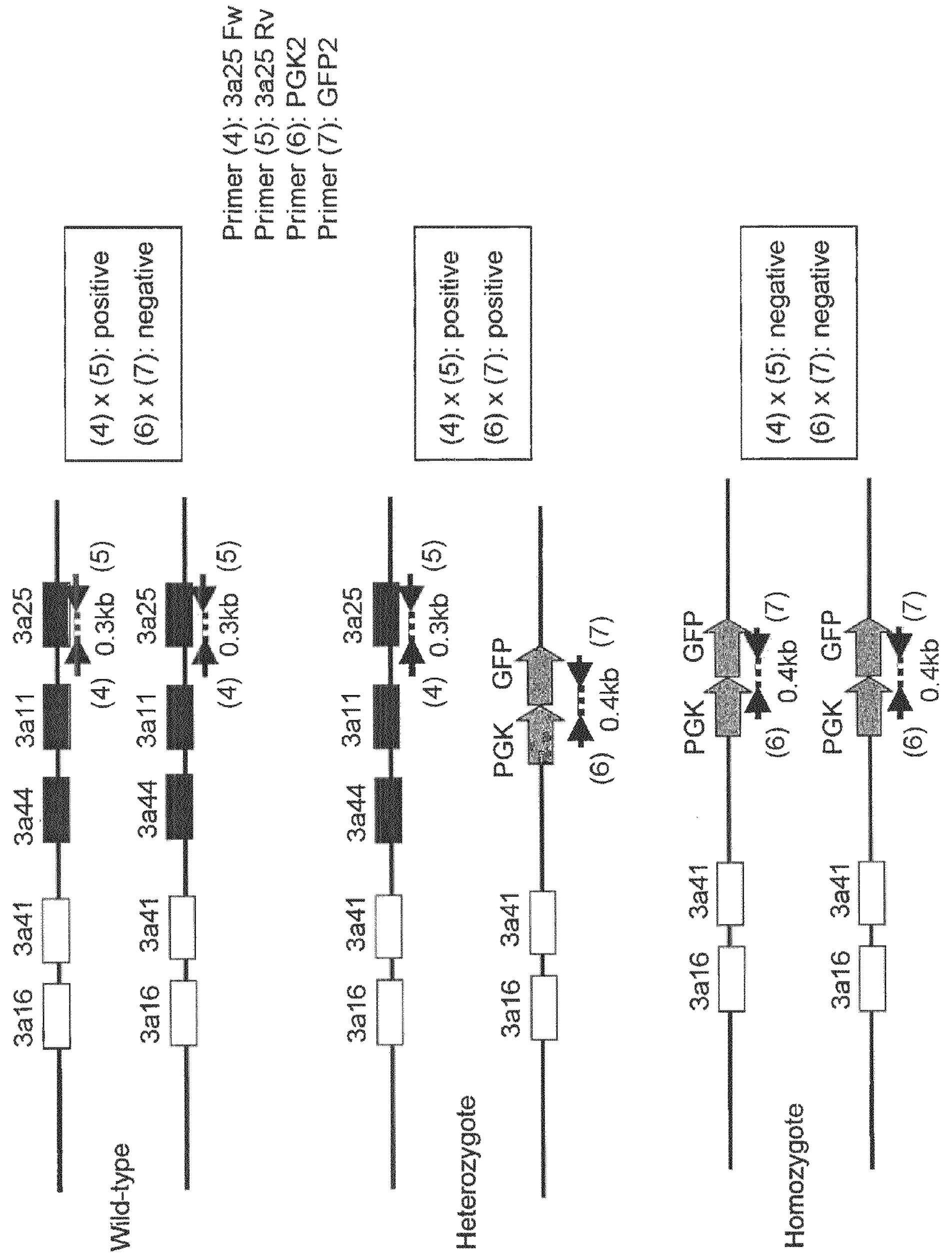
FIG. 19 schematically shows the genotype analysis of the cyp3a44/11/25-KO mouse individual.

A reaction solution (30 μl) was prepared using EX-Taq (Takara Bio, Japan) in accordance with the attached instructions, a combination of 3a25 Fw and 3a25 Rv (FIG. 19, (4)×(5)) or a combination of PGK2 and GFP2 (FIG. 19, (6)×(7)) was added as the primer pair, the genomic DNA of the progeny mice was added as a template, the mixture was heated at 85° for 3 minutes and 94° C. for 1 minute, and an amplification cycle of 94° for 10 seconds, 59° C. for 30 seconds, and 72° C. for 30 seconds was repeated 35 times. The reaction solution was electrophoresed on 2% gel to detect an amplification product. A specific product of 0.3 kb was detected regarding the wild-type Cyp3a44/11/25 allele with the use of the (4)×(5) primer combination, and a specific product of 0.4 kb was detected regarding the KO-type Cyp3a44/11/25 allele with the use of the (6)×(7) primer combination (FIG. 19). As a result of such analysis, the cyp3a44/11/25-KO heterozygote, which was heterozygous for Cyp3a13 knockout and positive for both (4)×(5) and (6)×(7) primer combinations, was obtained (FIG. 19).

In somatic cells of the double heterozygotes, which were heterozygous for both cyp3a44/11/25-KO and cyp3a13-KO, two types of KO alleles would not be present on the same chromosome. During the process of meiotic division for forming sperms or eggs, interchromosome recombination takes place, and gametes having two types of KO alleles on the same chromosome are generated with a certain probability. With the utilization of such phenomenon, an attempt had been made so as to obtain a mouse individual having the cyp3a44/11/25-KO allele and the cyp3a13-KO allele on the chromosome. The male double heterozygotes that are heterozygous for cyp3a13-KO/cyp3a44/11/25-KO obtained above were subjected to crossing with wild-type female C57BL/6N mice (CLEA Japan, Inc.), genomic DNA was prepared from the tail of the progeny mice, and the cyp3a44/11/25-KO and cyp3a13-KO genotypes described in 7.12 above were analyzed. In the somatic cells of the heterozygotes that were heterozygous for both KO alleles, two types of gene KO alleles were considered to be present on the same chromosome. As a result of the analysis, individuals that were heterozygous for both KO alleles were identified.

Further, construction of double-homozygous mice for both cyp3a44/11/25-KO and cyp3a13-KO alleles that lack three types of Cyp3a family genes was attempted via male and female crossing of double-heterozygous mice (the same chromosome) for both KO alleles obtained above. The male double heterozygotes obtained above (the same chromosome) were subjected to crossing with wild-type female C57BL/6N mice (CLEA Japan, Inc.), genomic DNA was prepared from the tail of the progeny mice, and the cyp3a44/11/25-KO and cyp3a13-KO genotypes described in 7.12 above were analyzed (FIGS. 18 and 19). As a result, individuals that were homozygous for both KO alleles that were found negative for cyp3a13-KO with the use of the (1)×(2) primer set and positive therefor with the use of the (1)×(3) primer set and that were found negative for cyp3a44/11/25-KO with the use of the (4)×(5) primer set and positive therefor with the use of the (6)×(7) primer set were obtained (FIGS. 18 and 19) (hereafter referred to as "Δcyp"). The genotypes of the Cyp3a cluster are as shown in Table 1 in relation to the primers above.

TABLE 1

| | Primer ½ | Primer ⅓ | 3z25Fw/Rv | PGK2/GFP2 |
|---|---|---|---|---|
| cyp normal | ○ | X | ○ | X |
| cyp hetero KO | ○ | ○ | ○ | ○ |
| cyp homo KO | X | ○ | X | ○ |

In Table 1, Primer 1 represents the sequence of SEQ ID NO: 103, Primer 2 represents the sequence of SEQ ID NO: 105, Primer 3 represents the sequence of SEQ ID NO: 104, 3a25Fw represents the sequence of SEQ ID NO: 106, 3a25Rv represents the sequence of SEQ ID NO: 107, PGK2 represents the sequence of SEQ ID NO: 43, and GFP2 represents the sequence of SEQ ID NO: 44.

The reproductive functions of the resulting double homozygous male and female mice were normal, and this strain was maintained via crossing of double-homozygous male and female mice.

Example 8

Construction of Mouse Strain Retaining CYP3A-HACΔ and Having Both Alleles of Endogenous Cyp3a Genes being Disrupted TC(CYP3A-HACΔ) constructed in Example 2 was back-crossed to the Δcyp strain constructed in Example 7, and the genotypes of the resulting mouse individuals were analyzed via PCR (see Examples 4 and 7). Tails of the 109 progeny mice resulting from crossing were partially cut, and genomic DNAs were prepared from the samples. The DNA samples were subjected to PCR using the primer for detecting the CYP3A gene cluster, the primer for detecting human chromosome 14, and the primers shown in Table 1 in the same manner as described above, and retention of CYP3A-HACΔ and Cyp3a gene cluster KO were investigated. As a result, 24 mice were found to be the mouse lineage retaining CYP3A-HACΔ and having one allele of the endogenous Cyp3a genes being disrupted (i.e., hetero KO). Further, such heterozygous mice that have the Cyp3a genes being disrupted and retain CYP3A-HACΔ were backcrossed to the Δcyp strain constructed in Example 7, tails of the 178 resulting progeny mice were partially cut, genomic DNAs were prepared from the samples, and the genotypes were analyzed via PCR in the same manner as above. As a result, 28 mice were found to be the mouse lineage retaining CYP3A-HACΔ and having both alleles of the endogenous Cyp3a genes being disrupted (i.e., homo KO, hereafter referred to as "TC(CYP3A-HACΔ)/Δcyp").

Example 9

Retention of CYP3A-HACΔ in Somatic Cell of TC(CYP3A-HACΔ)/Δcyp Mouse Strain (9.1) Genome PCR Analysis Genomes were obtained from the brain, the thymic gland, the heart, the lung, the liver, the kidney, the spleen, the small intestine, the muscle, and the spermary (or uterus) of a male (301) and a female (298) TC(CYP3A-HACΔ)/Δcyp mice obtained above, PCR was carried out using the obtained genomes as templates and the primer for detecting the CYP3A gene cluster and the primer for detecting human chromosome 14 in the same manner as above, and CYP3A-HACΔ was detected in all organs.

(9.2) Fluorescent In Situ Hybridization (FISH) Analysis

The brain, the thymic gland, the heart, the lung, the liver, the kidney, the spleen, the small intestine, the muscle, and the spermary (or uterus) of a male (301) and a female (298) TC(CYP3A-HACΔ)/Δcyp mice were subjected to FISH analysis using human cot-1 DNA as a probe by the method reported by Shinohara et al. (Human Molecular Genetics, 10: 1163-1175, 2001), and CYP3A-HACΔ was found to retained at the percentage of 49% to 95%. In the liver and the small intestine in which CYP3A would be mainly expressed, in particular, the percentage of chromosome retention was found to be as high as at least 84%.

Example 10

Expression of CYP3A/Cyp3a Gene Cluster in TC(CYP3A-HACΔ)/Δcyp Mouse Strain

Total RNAs were extracted from the liver of a B6 male mouse at 3-week-old (B6-6) and at 10-week-old (B6-1), the liver of a B6 female mouse at 3-week-old (B6-8) and at 10-week-old (B6-4), the liver of a Δcyp male mouse at 3-week-old (PT482) and at 10-week-old (PT449), the liver of a Δcyp female mouse at 3-week-old (PT485) and at 10-week-old (PT300), and the livers of a TC(CYP3A-HACΔ)/Δcyp male (301) mouse and female (298) mouse at 10-week-old in accordance with a commercially available protocol (QIAGEN), and cDNAs were synthesized in accordance with a commercially available protocol (Invitrogen). PCR was carried out using the cDNAs as templates to detect expression of the human CYP3A gene cluster and of the mouse Cyp3a gene cluster using the primers detecting expression of the same.

Figure 20:
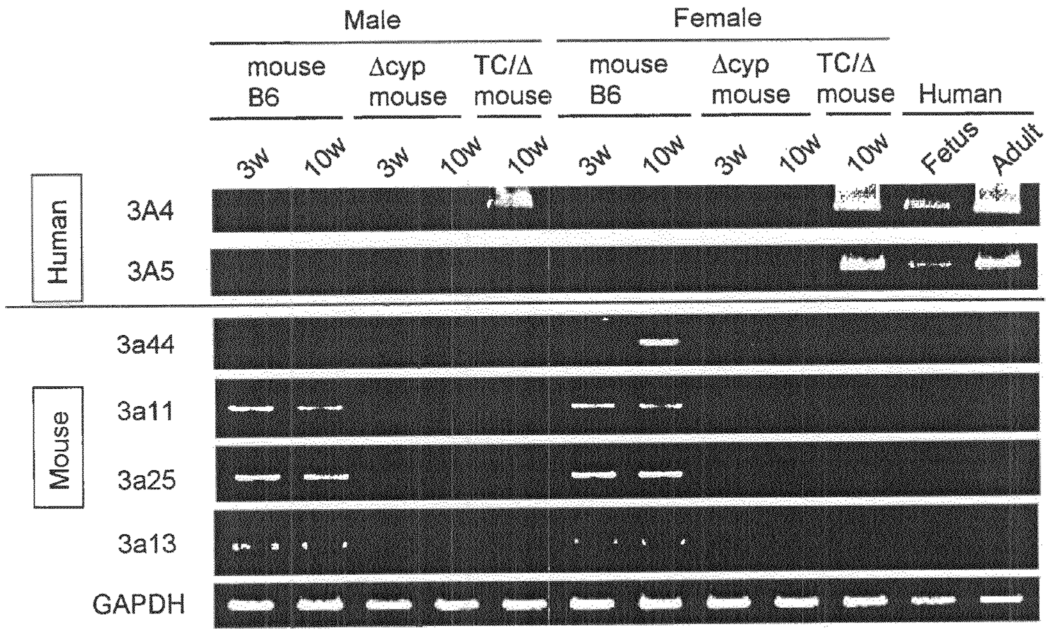
FIG. 20 shows the results of gene expression analysis in the liver of the TC (CYP3A-HACΔ)/Δcyp mouse.

As a result, it was confirmed that the mouse Cyp3a gene cluster was not expressed and the human CYP3A gene cluster was expressed in the TC(CYP3A-HACΔ)/Δcyp mouse, neither the mouse Cyp3a gene cluster nor the human CYP3A gene cluster was expressed in the Δcyp mouse, and the human CYP3A gene cluster was not expressed and the mouse Cyp3a gene cluster was expressed in the B6 normal mouse (FIG. 20).

Example 11

Induction of CYP3A Gene Cluster Expression in TC(CYP3A-HACΔ)/Δcyp Mouse Strain

In order to investigate the influence of pregnenolone 16α-carbonitrile (PCN) (Sigma), which is known as a substance inducing CYP3A/Cyp3a expression, on CYP3A/Cyp3a gene expression in TC(CYP3A-HACΔ)/Δcyp, Δcyp, and B6 normal mice, PCN was administered intraperitoneally for 4 days in amounts of 100 mg/kg per dose. A suspension of PCN in corn oil (Sigma) was prepared for administration. The liver was extracted from mice on day 5, proteins were extracted from the liver microsome fractions, and Western blot analysis was carried out in accordance with the method of Masato Okada and Kaoru Miyazaki (*Tanpakushitsu Jikken Note* (Protein Experiment Note), Yodosha (Japan), 1996) using the anti-CYP3A antibody (Dai-ichi Kagaku Yakuhin (Japan); Catalog No. 242496) and the anti-β-actin antibody (Sigma Aldrich; Catalog No. A5441).

Figure 21:
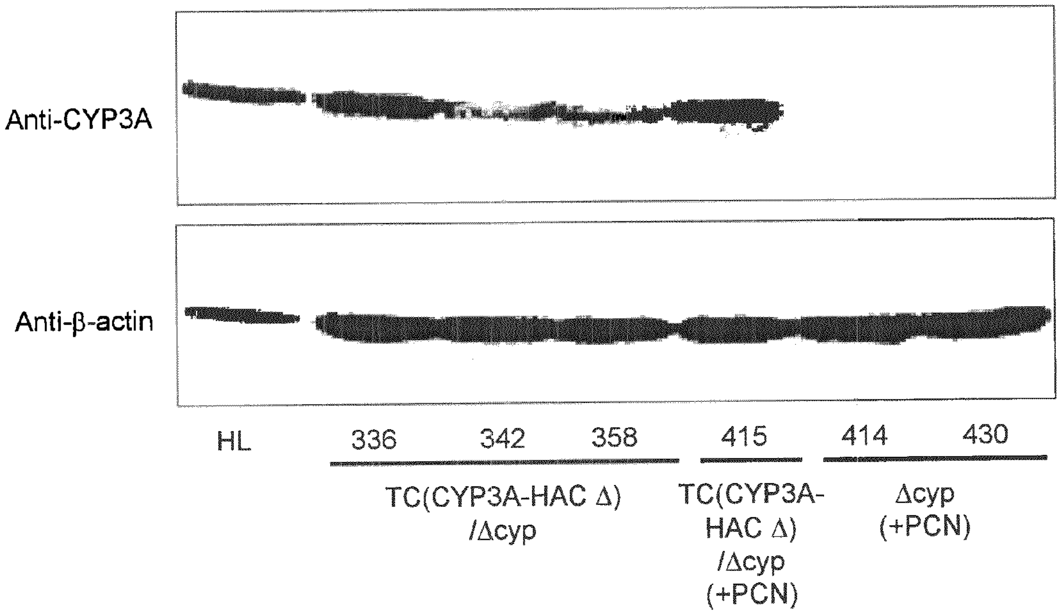
FIG. 21 shows the results of CYP3A gene expression analysis via Western blotting of the TC(CYP3A-HACΔ)/Δcyp mouse after induction of gene expression.

As a result, the CYP3A expression level was found to be elevated in the TC (CYP3A-HACΔ)/Δcyp mice and B6 normal mice to which PCN had been administered, compared with mice of the same strains to which corn oil had been administered. Such expression level was substantially the same as that of the protein extracted from human microsome fragment. Expression was not observed in Δcyp mice to which PCN had been administered. Meanwhile, β-actin expression levels (the control) were substantially the same in all mice. It was thus confirmed that expression of the human CYP3A gene on CYP3A-HACΔ of the TC(CYP3A-HACΔ)/Δcyp mouse strain was induced by a CYP3A/Cyp3a inducer (FIG. 21).

Example 12

Metabolism Analysis in TC(CYP3A-HACΔ)/Δcyp Mouse Strain

Figure 22:
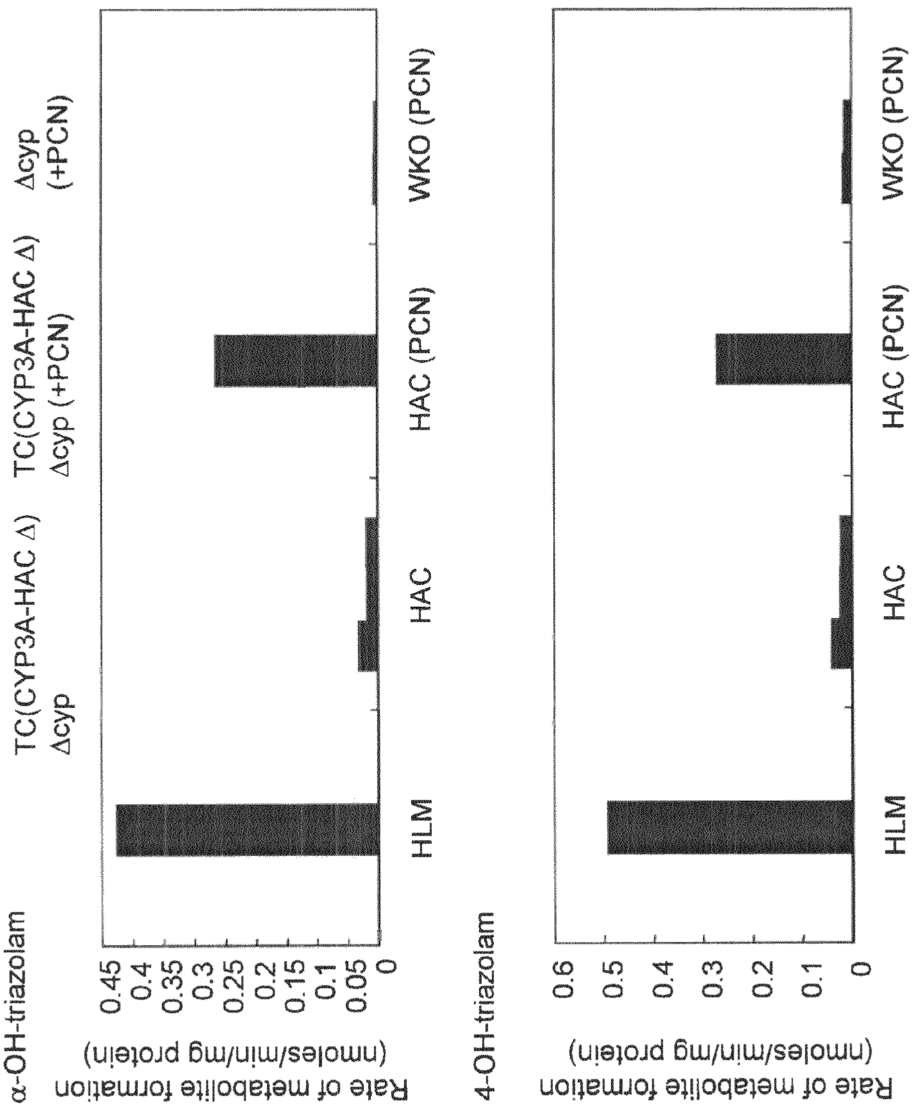
FIG. 22 shows the results of metabolism analysis of the TC(CYP3A-HACΔ)/Δcyp mouse after induction of gene expression.

The liver microsomes obtained from the TC(CYP3A-HACΔ)/Δcyp mice and the Δcyp mice to which PCN or corn oil had been administered above were mixed with 200 μM of triazolam, which is known to be metabolized by CYP3A4, in accordance with the method of Omura et al. (J. Biol. Chem., 239, 2370, 1964), and the metabolites; i.e., α-OH-triazolam and 4-OH-triazolam, were assayed. As a result, the metabolic activity of the TC (CYP3A-HACΔ)/Δcyp mice to which PCN had been administered was 10 times higher than that of the mice of the same strain to which corn oil had been administered, which was about a half that of humans (HLM: human liver microsomes). Also, substantially no activity was observed in the Δcyp mice to which PCN had been administered. A human has two homologous genes, and the TC(CYP3A-HACΔ)/Δcyp mouse is considered to have the CYP3A gene cluster, which is equivalent to a chromosome. The fact that about a half activity of humans was exhibited in the TC(CYP3A-HACΔ)/Δcyp mouse indicates a similar metabolic activity with that of a human. However, substantially no activity was observed in the Δcyp mice to which PCN had been administered. It was thus confirmed that the human CYP3A gene on CYP3A-HACΔ in the TC(CYP3A-HACΔ)/Δcyp mouse strain was functional and equivalent to that in humans (FIG. 22).

Example 13

Assay of Human-Specific Metabolite in TC(CYP3A-HACΔ)/Δcyp Mouse Strain

Figure 23:
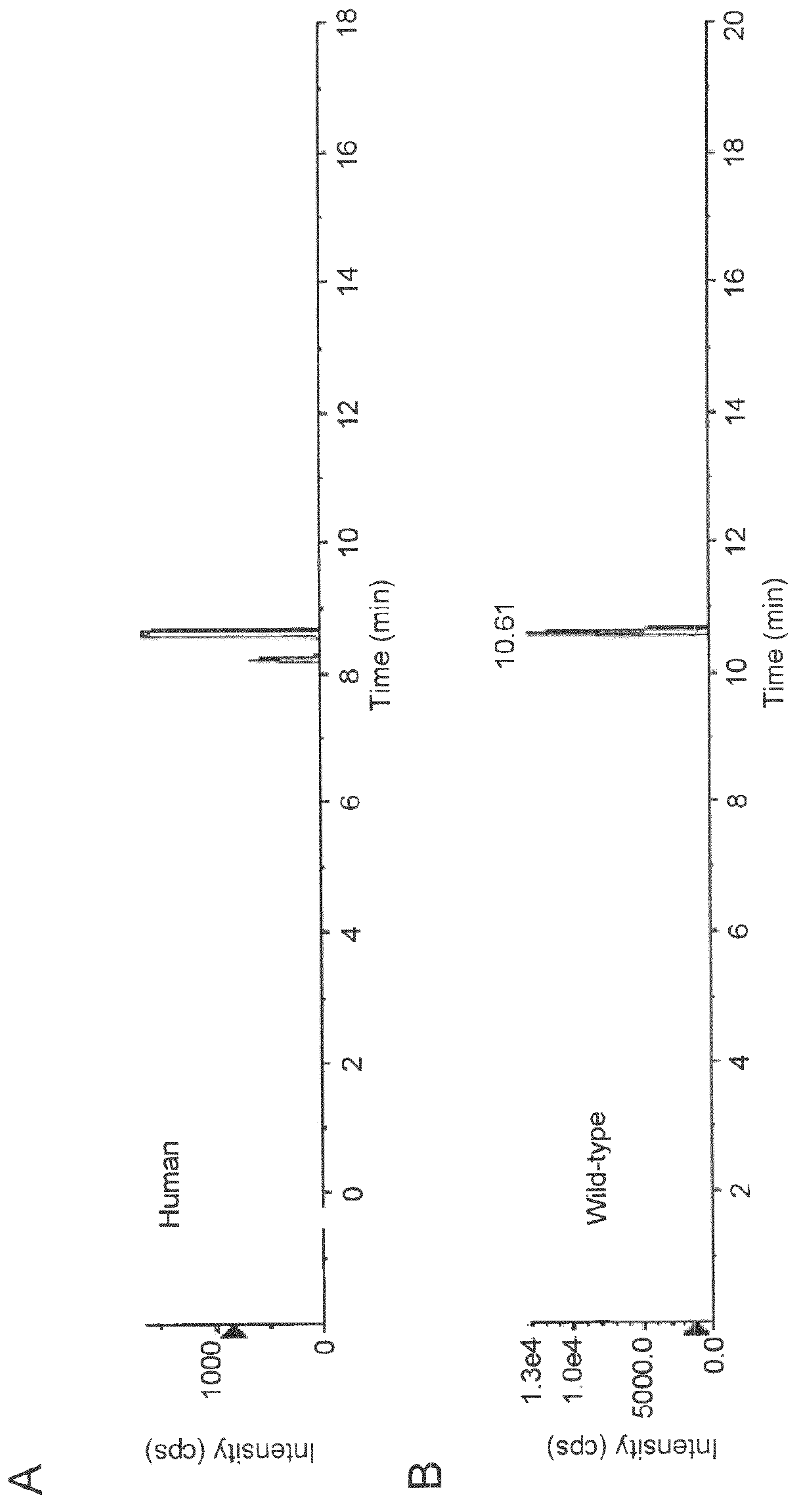
FIG. 23 shows the results of human-specific metabolites in the TC (CYP3A-HACΔ)/Δcyp mouse measured by LC-MS/MS.
Figure 23:
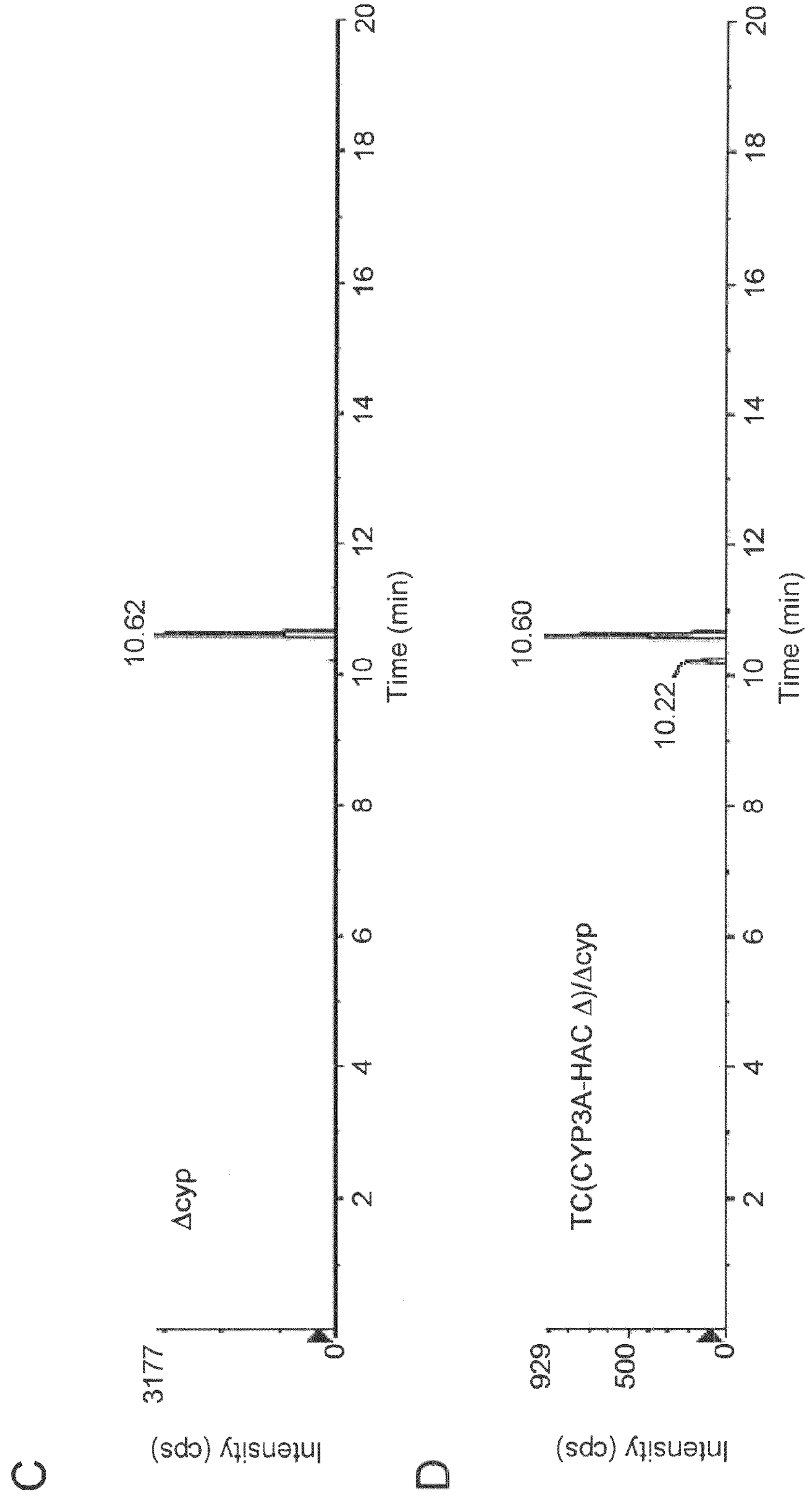

In order to investigate whether or not a human-specific metabolite of midazolam, which is known to be metabolized by CYP3A/Cyp3a, is observed in the TC (CYP3A-HACΔ)/Δcyp mouse as in the case of a human, microsomes derived from the liver of the TC(CYP3A-HACΔ)/Δcyp mouse, the Δcyp mouse, the B6 normal mouse, and the human were allowed to react with midazolam, and mass analysis was carried out via LC-MS/MS in the following manner. The reaction mixture (10 μM midazolam, 87.5 mM potassium phosphate buffer (pH 7.4), and 0.5 mg/ml hepatic microsomes) was preincubated at 37° C. for 5 minutes, the NADPH-generating system (3.3 mM β-NADP+, 80 mM glucose-6-phosphate, and 10 units/ml of glucose-6-phosphate dehydrogenase) was added, and incubation was carried out at 37° C. for 30 minutes. The reaction was terminated with the addition of acetonitrile, the mixture was centrifuged at 3,000 rpm for 5 minutes, and the supernatant was separated. The solvent was removed therefrom by distillation under a nitrogen stream at 40° C., the dried extract was redissolved in acetonitrile, and mass analysis was carried out by LC-MS/MS As a result, metabolites specific for 10.22 was detected in the microsomes of the human and of the TC(CYP3A-HACΔ)/Δcyp mouse. In contrast, the main metabolite; i.e., 10.62, was detected in all microsomes. It was thus confirmed that the human CYP3A gene on CYP3A-HACΔ in the TC(CYP3A-HACΔ)/Δcyp mouse strain was functional and equivalent to that in humans (FIG. 23).

Example 14

(14.1) Preparation of ntES Cell Derived from ΔCyp Mouse

Tail fibroblasts of the Δcyp mouse obtained in Example 7 were cultured in accordance with the method of Wakayama et al. (Science, 292: 740, 2001), and the nuclei derived from the Δcyp mouse-derived tail fibroblasts were injected into the enucleated unfertilized eggs. Three ntES cell lines were established from a male Δcyp mouse (No. 596) and from a female Δcyp mouse (No. 480) (596-1, 2, and 3 and 480-1, 2, and 4).

(14.2) Removal of Neo-Resistant Gene from ntES Cell Derived from Δcyp Mouse

It is necessary to remove the neo-resistant gene that is present in Δcyp-ntES in order to introduce CYP3A-HAC and CYP3A-HACΔ into Δcyp-ntES. Thus, the neo-resistant gene (sandwiched by two loxP sequences, see FIG. 17) used to knockout the Cyp3a13 gene was removed in the following manner. The Cre recombinase expressing vector, pBS185 (Gibco), was transfected into 6 clones of the Δcyp-ntES cell line obtained above. This can cause site-specific recombination between loxP sequences located in the mouse endogenous Cyp3a13 gene region and consequently delete the neo gene. The Δcyp-ntES cells were treated with trypsin and suspended in HBS to a concentration of $1.0\times10^7$ cells/ml, 30 μg of the pBS185 vector (Invitrogen) was added, and electroporation was carried out using the Gene Pulser at 250 V and 960 μF. Thereafter, the cells were sowed on a 100-mm petri dish. When loxP recombination occurs as expected, the neo gene in the vector would not be expressed, and detection may be made based on G418 resistance. Culture was conducted for 72 hours after the introduction of the Cre expressing vector, pBS185, cells were peeled from the dish via trypsin treatment, the cells were suspended in DMEM for ES cells, the suspension was transferred to a 15-ml tube, centrifugation was carried out at 1,000 rpm for 5 minutes, and the supernatant was suctioned. After the tube was subjected to tapping, the cells were resuspended in 10 ml of DMEM for ES cells, the suspension was sowed on a gelatin-coated 100-mm dish, and culture was conducted for about 1 hour. Thereafter, the medium was gently recovered, and centrifugation was carried out at 1,000 rpm for 5 minutes. Thereafter, the supernatant was suctioned, the cell mass was loosened via tapping, and the cells were sowed on a 60-mm dish seeded with feeder cells, so that several tens of sufficiently separated colonies would develop. One week later, 12 colonies were picked up relative to each clone on a 24-well plate seeded with feeder cells, the colonies were sowed on two 24-well plates seeded with feeder cells several days later, a G418-containing medium was added to a plate, and a G418-free medium was added to the other plate (i.e., the master plate). Since the clones that had died in the G418-containing medium were considered to be clones from which neo-resistant genes had been removed, the master plate of the clones that had been killed by G418 was grown, and the cells contained in a well of the 24-well plate were seeded in 2 wells of a 4-well plate. The cells in a well of the 4-well plate were cryopreserved at −80° C. The remaining cells in the other well were seeded and cultured on a 3.5-cm gelatin-coated dish for obtaining genomic DNA. Genomic DNA was prepared from the cells and subjected to PCR using the Primers 1/2 and Primers 1/3 described in Example 7 to confirm that the cells of interest lack the neo gene. The clones from which the neo-resistant genes had been removed were deduced to exhibit the same pattern as the normal mice shown in Table 1. PCR demonstrates that 5 among 12 clones of 480-1 lack the neo genes, 7 among 12 clones of 480-2 lack the neo genes, 8 among 12 clones of 480-4 lack the neo genes, 9 among 12 clones of 596-1 lack the neo genes, 8 among 12 clones of 596-2 lack the neo genes, and 10 among 12 clones of 596-3 lack the neo genes. Also, all of such clones were non-G418-resistant.

Thus, such clones were found to be the Δcyp-ntES (G-) cells from which all the neo genes had been removed.

Example 15

Introduction of CYP3A-HAC or CYP3A-HACΔ into Δcyp-ntES (G-) Cell

In order to construct a chimeric mouse retaining the Δcyp-ntES (G-) cells comprising CYP3A-HAC or CYP3A-HACΔ, CYP3A-HAC or CYP3A-HACΔ was transferred from the CHO cells retaining the same (obtained in Example 2) to the Δcyp-ntES (G-) obtained in Example 14 by the microcell method. In accordance with the method of Tomizuka et al. (Nature Genet. 16: 133, 1997), microcells were purified from about $10^8$ CHO cells retaining CYP3A-HAC or CYP3A-HACΔ (e.g., CHO/CYP3A-HAC4, 25, 32, and 33 or CHO/CYP3A-HACΔ4, 6, 7, and 10), and the microcells were suspended in 5 ml of DMEM. The Δcyp-ntES (G-) cells (about $10^7$ cells, such as 596-1-2 and 596-2-9) were peeled via trypsin treatment, washed three times with DMEM, suspended in 5 ml of DMEM, added to the centrifuged microcells, and centrifuged at 1,250 rpm for 10 minutes, followed by complete removal of the supernatant. The precipitate was thoroughly loosened via tapping, 0.5 ml of 1:1.4 PEG solution (a solution of 5 g of PEG1000 (Wako Pure Chemical Industries, Ltd.) and 1 ml of DMSO (Sigma) in 6 ml of DMEM) was added, and the mixture was thoroughly agitated for about 1 minute and 30 seconds. Thereafter, 10 ml of DMEM was slowly added, the mixture was centrifuged at 1,250 rpm for 10 minutes, the resultant was suspended in 30 ml of ES medium, the suspension was fractionated into three petri dishes having a diameter of 100 mm (Corning) seeded with feeder cells, and culture was conducted. The medium was exchanged with a medium containing G418 at 300 μg/ml 24 hours thereafter, and selective culture was carried out for about 1 week. As a result, 21 clones resulting from Δcyp-ntES (G-) cells (Δcyp-ntES (G-)/CYP3A-HAC) retaining CYP3A-HAC and 57 clones resulting from the Δcyp-ntES (G-) cells (Δcyp-ntES (G-)/CYP3A-HACΔ) retaining CYP3A-HACΔ were found positive via PCR using the primer for detecting the CYP3A gene cluster and the primer for detecting human chromosome 14. As a result of FISH analysis using the human COT1 DNA probe (Tomizuka et al., Nature Genet. 16: 133, 1997) regarding each clones of the Δcyp-ntES (G-)/CYP3A-HAC cells and the Δcyp-ntES (G-)/CYP3A-HACΔ cells obtained above, the presence of CYP3A-HAC detected specifically by the COT1 probe was observed in 11 of the 12 clones, and the presence of CYP3A-HACΔ was observed in 12 of the 12 clones. Among such clones, 5 clones of Δcyp-ntES (G-)/CYP3A-HAC and 9 clones of Δcyp-ntES (G-)/CYP3A-HACΔ exhibited normal mouse karyotypes. It was thus concluded that at least 5 clones were obtained from the Δcyp-ntES (G-)/CYP3A-HAC cells and at least 9 clones were obtained from the Δcyp-ntES (G-)/CYP3A-HACΔ cells.

Example 16

Construction of Chimeric Mouse from Δcyp-ntES (G-)/CYP3A-HAC or Δcyp-ntES (G-)/CYP3A-HACΔ

Chimeric mice were constructed using the clones of the ntES cells obtained in Example 15 by the method of Wakayama et al. (Science, 292: 740, 2001). As the host cells, blastocyst-stage embryos obtained via male and female crossing of MCH (ICR) mice (white, purchased from CLEA Japan, Inc.) were used. Whether or not progeny mice resulting from transplantation of the injected embryos into foster parents are chimeric mice can be determined based on hair color. As a result of transplantation of about 500 embryos into which Δcyp-ntES (G-)/CYP3A-HAC or Δcyp-ntES (G-)/CYP3A-HACΔ had been injected (e.g., Δcyp-ntES (G-)/CYP3A-HAC5, 6, 7, and 11 and Δcyp-ntES (G-)/CYP3A-HACΔ25, 63, and 67 obtained in Example 15) into foster parents, 26 chimeric mice were born from Δcyp-ntES (G-)/CYP3A-HAC, and 29 chimeric mice were born from Δcyp-ntES (G-)/CYP3A-HACΔ (black color was observed in hair). Specifically, ntES cell lines retaining the human artificial chromosome CYP3A-HAC or CYP3A-HACΔ have the capacity for chimera formation; i.e., the capacity for differentiating into mouse normal tissue.

Example 17

Retention of Artificial Chromosome in Somatic Cells of Chimeric Mice Constructed from Δcyp-ntES (G-) Cells Retaining CYP3A-HAC or CYP3A-HACΔ

(17.1) Genome PCR Analysis

Genomic DNAs were prepared from the tails of the chimeric mice (percentage of chimerism=about 50%) constructed from cyp-ntES (G-)/CYP3A-HAC clones (Δcyp-ntES (G-)/CYP3A-HAC5, 6, 7, and 11) or Δcyp-ntES (G-)/CYP3A-HACΔ (Δcyp-ntES (G-)/CYP3A-HACΔ25, 63, and 67) in Example 16 by the method of Tomizuka et al. (Nature Genet. 16: 133, 1997), PCR was carried out using the primer for detecting the CYP3A gene cluster and the primer for detecting human chromosome 14 in the same manner as above, and whether or not the chimeric mice retained CYP3A-HAC or CYP3A-HACΔ was investigated. As a result, all the investigated 10 chimeric mice were found to be positive for two types of primers and retain CYP3A-HAC or CYP3A-HACΔ in somatic cells.

(17.2) Fluorescent in Situ Hybridization (FISH) Analysis

As a result of FISH analysis using the tail fibroblasts prepared from the chimeric mice (percentage of chimerism=about 50%) constructed from Δcyp-ntES (G-)/CYP3A-HAC or Δcyp-ntES (G-)/CYP3A-HACΔ by the method of Shinohara et al. (Human Molecular Genetics, 10, 1163-1175, 2001) using the human COT1 DNA probe, the presence of CYP3A-HAC or CYP3A-HACΔ was visually observed, and CYP3A-HACΔ was found to be present independently from the mouse chromosome. Since the percentage of CYP3A-HAC or CYP3A-HACΔ retention was about 50%, CYP3A-HAC or CYP3A-HACΔ was found to be efficiently retained consistently with the percentage of chimerism.

It was thus suggested that in vitro or in vivo induction of differentiation of Δcyp-ntES (G-)/CYP3A-HAC or Δcyp-ntES (G-)/CYP3A-HACΔ that lacks the endogenous mouse Cyp3a gene cluster and retains the human CYP3A gene cluster into various types of cells enables the provision of cells that do not express the mouse Cyp3a gene cluster and express the human CYP3A gene cluster.

INDUSTRIAL APPLICABILITY

When a mammalian artificial chromosome vector retaining a given region containing the human P450 gene (the CYP3A gene cluster) on human chromosome 7 is introduced into a non-human mammalian animal, such as a mouse, according to the present invention, a non-human mammalian animal that can be stably genetically transmitted to progeny and stably retained in animal tissue, which had been impossible in the past, in addition to a satisfactory percentage of chimerism and a satisfactory percentage of chromosome retention, can be provided. That is, a progeny animal that enables human P450 gene expression can be provided.

The present invention has the following effects.

(1) A human artificial chromosome that retains the human P450 gene region, that can be efficiently transmitted to the next generation, and that can be stably maintained therein is provided.

(2) Also, an ES cell derived from a non-human animal retaining the human artificial chromosome is provided.

(3) The present invention also provides a non-human animal that stably maintains the human artificial chromosome and efficiently transmits the same to the next generation and progeny thereof.

A progeny resulting from crossing of the knockout non-human mammalian animal in which the endogenous P450 genes of the non-human mammalian animal (i.e., the homologous gene of the above) is disrupted or a progeny thereof is considered to be completely humanized regarding a given P450 molecular species. In addition to tissue-specificity of expression, the percentage of drug induction, and the percentage of expression, a non-human mammalian animal into which human P450 has been introduced, which is completely humanized regarding to a given P450 molecular species in terms of functions of metabolites, can be provided.

(4) With the use of the non-human mammalian animal into which human P450 has been introduced and which has been completely humanized regarding a given P450 molecular species, influence of a drug, such as a pharmacological effect, drug metabolism, or toxicity, on humans can be studied or predicted without actual administration of drugs to humans.

(5) Further, by culturing all the embryos of the non-human mammalian animal into which human P450 has been introduced and which has been completely humanized regarding a given P450 molecular species, metabolism, drug toxicity, malformation, or the like thereof can be evaluated.

(6) Biologically active human P450 proteins can be obtained from a non-human mammalian animal into which human P450 has been introduced and which has been completely humanized regarding a given P450 molecular species, tissues thereof, or cells thereof. Such proteins can easily provide human P450 proteins, which was difficult to obtain in the past. Further, proteins that are more similar to P450 produced in human bodies in terms of protein modification, represented by phosphorylation or modification with the use of a sugar chain, which could not be realized by the expression system involving the use of bacterial represented by *E. coli*, can be provided.

(7) When tissue or cells derived from the non-human mammalian animal are immortalized and used in a culture system, human P450 proteins can be stably supplied. Further, such tissue or cells can be used as research materials in the culture system for drug metabolism in humans.

All publications, patents, and patent applications cited herein are incorporated herein by reference in their entirety.

Sequence Listing Free Text

SEQ ID NOs: 1 to 86 and 99 to 107: primers

SEQ ID NOs: 87 to 98: oligo DNAs

The invention claimed is:

1. A human artificial chromosome vector, which retains a human chromosome 7 fragment comprising at least one human cytochrome P450 gene and is transmittable to progeny, wherein the human artificial chromosome vector is CYP3A-HACΔ retained by the chicken DT40 cell line DT40 (CYP3A-HACΔ) 214 which has been deposited under the international deposit Accession Number FERM BP-10928.

* * * * *

```
                         SEQUENCE LISTING


<160> NUMBER OF SEQ ID NOS: 107

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

ggcctagagc ctggactcat tcattcaa                                       28


<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

gacagatgtc atgccccagg taggtatg                                       28


<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

agttcttttg agggcctaga gcctggac                                       28
```

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
aaaggacaga aggagggagc aacaggat 28

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
tctgggcatc agtgtcctct ccagtaaa 28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
ttggcgacat ccaatgctag tgctattc 28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
tggagacgtt gtttagcctc tcctcctc 28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
cacagcttag aggccattcc catagtcc 28

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
ccttcattac gtcctttcgc 20

-continued

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
agtcatcact gcatcctggg 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
taggtccttt aggccatggg 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gcattttggc ctcaagtagc 20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
tgcttgttca tctgtcagtg g 21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
atcacaaggt caagcgatcg 20

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
attttgggac ttcctggc 18

```
<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

aatctgtttg cagtcttcac c                                              21


<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(22)
<223> OTHER INFORMATION: a, c, t, or g

<400> SEQUENCE: 17

gagttcaagg ttacagtaag tnatg                                          25


<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

ctcttgtctc atagtgcaaa gg                                             22


<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

gaaactctag catgtaacac tccaa                                          25


<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

gagccactgc acctgg                                                    16


<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 21
gcactacatt aaagatgtgc aacc 24

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
actctcacac ccacccagac 20

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
atgtgggaaa cagactcag 19

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
atttggatta tttagaattc cc 22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gcatcctgac cgtgtccgaa 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
gggtcagtag caggtgccag 20

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
agctcctata tgtcttcaca cag 23

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ctccattccc atacgtcc 18

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
tagggacagg cagttgatta 20

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
caattaatgt aaaaattagc ca 22

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
tgtttgaaga agggagtcgt 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
cccactccat gtcttctgtt 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
agtgagataa gcagtggatg 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
cttgtgctac tcccatcact 20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
gcaagactgt gagccagtga 20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
ggctgcatca gcatcatcta 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
accctgaaat gaagacgggc 20

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gagttaatgg tgctaactgg gg 22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
atagaagggt ctgtctggct gg 22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
tcagctgtgt gctgttgttt gc 22

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
atagcagctt tgctccttcg 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
ttctctcctg cacatagccc 20

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
tgttctcctc ttcctcatct cc 22

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
tgaaggtagt gaccagtgtt gg 22

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
tgcggtgaag gtccaaggag atagattt 28

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
tctagcagag agatggtggc aggattca 28

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
cctaacatcg tgtcccagct ca 22

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
tcctttcaga ccccttcatc ttag 24

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
ttcagcccca accaaagaca cta 23

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
gccccgaacc cctacaaata taga 24

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
gggcctccaa taagtgtccc ata 23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
ttgctgactt agttgcagca gga 23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
cccattggca agatacatgg aga 23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
agtgtggatg ctcctggatg aag 23

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
gtaaacgccc tcaaggagca agcatga 27

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
tgtgaccaaa gatttagcgc agtgcgt 27

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
gtatggaaaa gtgtggggct 20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
atacttcaag aattgggatg 20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
ccaagctatg ctcttcaccg 20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
tgaagaagtc ctcctaagct 20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
ctctgtttcc aaaagatacc 20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
tcaacatctt tcttgcaagt 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
agcttttaag atttaatcca 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 64
gagctttgtg ggtctcagag 20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 65
ctctcagaat tcaaaagact 20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 66
agaagaagtc ctccaaagcg 20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 67
tatgacacaa ctagcaccac 20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 68
agtgtctagt gttctgggat 20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 69
tcaaacgcct ctccttgctg 20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
gcttgccttt ctttgccttc 20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
ggtaaagtac ttgaggcaga 20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
agaaagggct ttatgagaga 20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
agaaacatga ggcagggatt 20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
acaaggagac atttagtgca 20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
taccccagta tttgatgcac 20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
agataactga ctgagccaca 20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
cttctacata tatgggacct 20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
accgacggtt tgtgaagact 20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
agaaagaacg ccttgcttca 20

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
ttgggcagag ttctgtca 18

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
cactggatac attggtcctg 20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
cgtgatgaca aggagaggtg 20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
agaggatcct tttgtggagg 20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
ctttggaatt attatgagaa 20

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
ccatcttcca ggagcgaga 19

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
tgtcatacca ggaaatgagc 20

<210> SEQ ID NO 87
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
tcgagtcgcg acaccggcgg gcgcgccc 28

<210> SEQ ID NO 88
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
tcgagggcgc gcccgccggt gtcgcgac 28

<210> SEQ ID NO 89
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
ggccgcttaa ttaaggccgg ccgtcgacg 29

<210> SEQ ID NO 90
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
aattcgtcga cggccggcct taattaagc 29

<210> SEQ ID NO 91
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
cggcgcgccg tatacc 16

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
tcgaggtata cggcgcgccg agct 24

<210> SEQ ID NO 93
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
gcggccgcga cgtccagctg ggccggccgg cgcgcc 36

<210> SEQ ID NO 94
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 94
ggcgcgccgg ccggcccagc tggacgtcgc ggccgc 36

<210> SEQ ID NO 95
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 95
ggcgcgccct cctggctacc agcctggtcc ttctc 35

<210> SEQ ID NO 96
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 96
gtatacttac ttaccccata ggagggattt gcataggacc 40

<210> SEQ ID NO 97
<211> LENGTH: 105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97
ctgggcaggg aagggagctc agcaggctca gccctgaaag gtgcagcaca caaaattgag 60
agtacaactt ggagagagac ttgtttaaag aaaacagcag gccgg 105

<210> SEQ ID NO 98
<211> LENGTH: 101
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98
cctgctgttt tctttaaaca agtctctctc caagttgtac tctcaatttt gtgtgctgca 60
cctttcaggg ctgagcctgc tgagctccct tccctgccca g 101

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
probe

<400> SEQUENCE: 99
ccctccttgt cactgatgct 20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
probe

<400> SEQUENCE: 100
tctgggagga cagaatgctt 20

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
probe

<400> SEQUENCE: 101
tcacacatct ctagatgact acgg 24

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
probe

<400> SEQUENCE: 102
atagactgcc atggaggaac 20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 103
agttccagag ggacaccttc 20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 104
ttccacacct ggttgctgac 20

<210> SEQ ID NO 105
<211> LENGTH: 20
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 105

agattcaagt gggcacaccc                                                20


<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106

cattgttctg gctttagcgt c                                              21


<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107

ctgcaaccct gaggctttag                                                20
```